United States Patent
Ellies et al.

(10) Patent No.: US 10,501,457 B2
(45) Date of Patent: Dec. 10, 2019

(54) COMPOUNDS FOR BONE GROWTH

(71) Applicant: OsteoQC Inc., Montreal (CA)

(72) Inventors: Debra Ellies, Parkville, MO (US); Jean-Philippe Rey, Kansas City, MO (US); F. Scott Kimball, Olathe, KS (US)

(73) Assignee: OsteoQC Inc., Montreal (CA)

( * ) Notice: Subject to any disclaimer, the term of this patent is extended or adjusted under 35 U.S.C. 154(b) by 0 days.

(21) Appl. No.: 15/365,283

(22) Filed: Nov. 30, 2016

(65) Prior Publication Data

US 2017/0298059 A1    Oct. 19, 2017

Related U.S. Application Data

(63) Continuation of application No. 14/214,037, filed on Mar. 14, 2014, now Pat. No. 9,540,365.

(60) Provisional application No. 61/785,306, filed on Mar. 14, 2013.

(51) Int. Cl.
C07D 471/04 (2006.01)
C07D 209/86 (2006.01)
C07C 53/06 (2006.01)
C07C 59/265 (2006.01)

(52) U.S. Cl.
CPC ............ C07D 471/04 (2013.01); C07C 53/06 (2013.01); C07C 59/265 (2013.01); C07D 209/86 (2013.01)

(58) Field of Classification Search
CPC ........................ C07D 471/04; C07D 209/86
USPC ......................................................... 546/81
See application file for complete search history.

(56) References Cited

U.S. PATENT DOCUMENTS

| | | | |
|---|---|---|---|
| 2,688,022 A * | 8/1954 | Burtner | C07D 471/04 544/126 |
| 2,767,179 A | 10/1956 | Cavallito et al. | |
| 2,800,474 A | 7/1957 | Voegtli | |
| 5,494,928 A | 2/1996 | Bos | |
| 6,627,637 B2 | 9/2003 | Ritzeler et al. | |
| 9,540,365 B2 * | 1/2017 | Ellies | C07D 471/04 |
| 2005/0085554 A1 | 4/2005 | Hamann et al. | |
| 2007/0054151 A1 | 3/2007 | Iwakuma et al. | |
| 2007/0060606 A1 | 3/2007 | Robertson et al. | |
| 2007/0191851 A1 | 8/2007 | Ashammakhi | |
| 2010/0063085 A1 | 3/2010 | Cohen | |
| 2010/0074939 A1 | 3/2010 | Ellies et al. | |
| 2010/0173931 A1 | 7/2010 | Ellies et al. | |
| 2012/0302755 A1 | 11/2012 | Szardenings et al. | |
| 2013/0028958 A1 | 1/2013 | Rommelspacher | |
| 2013/0131070 A1 | 5/2013 | Buolamwini | |
| 2013/0315965 A1 | 11/2013 | Ellies et al. | |

FOREIGN PATENT DOCUMENTS

| | | |
|---|---|---|
| CN | 102796124 A | 11/2012 |
| DE | 4436190 A1 | 4/1996 |
| EP | 0548553 A1 | 6/1993 |
| EP | 0705831 A2 | 4/1996 |
| EP | 0799829 A1 | 10/1997 |
| EP | 0815110 A1 | 1/1998 |
| EP | 1134221 A1 | 9/2001 |
| EP | 1209158 A1 | 5/2002 |
| FR | 2003999 A | 11/1969 |
| GB | 1268772 | 3/1972 |
| JP | 2005-530811 A | 10/2005 |
| JP | 2011-505379 A | 2/2011 |
| WO | WO-2000/002878 A1 | 1/2000 |
| WO | WO-03/099814 A1 | 12/2003 |
| WO | WO-2007/091707 A1 | 8/2007 |
| WO | WO-2009/029625 A1 | 3/2009 |
| WO | WO-2009/073620 A2 | 6/2009 |
| WO | WO-2009/073620 A9 | 6/2009 |
| WO | WO-2010/015636 A1 | 2/2010 |
| WO | WO-2010/123583 A2 | 10/2010 |

(Continued)

OTHER PUBLICATIONS

Banker G.S. 1996 pp. 451-596 (Year: 1996).*

(Continued)

*Primary Examiner* — Rita J Desai

(74) *Attorney, Agent, or Firm* — Mintz Levin Cohn Ferris Glovsky and Popeo, P.C.

(57) ABSTRACT

In one aspect, the invention provides compounds of Formula I, and salts, hydrates and isomers thereof. In another aspect, the invention provides a method of promoting bone formation in a subject in need thereof by administering to the subject a therapeutically effective amount of a compound of Formula I, Formula II, or Formula III. The present invention also provides orthopedic and periodontal devices, as well as methods for the treatment of renal disease and cancer, using a compound of Formula I, Formula II, or Formula III.

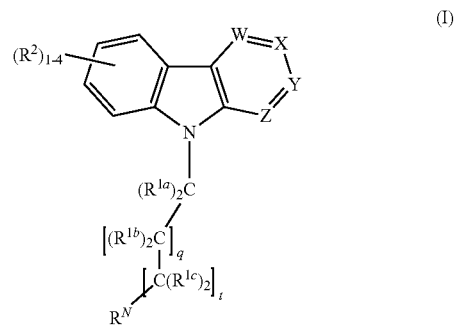

(I)

14 Claims, 1 Drawing Sheet

(56) References Cited

FOREIGN PATENT DOCUMENTS

| WO | WO-2011/079841 A1 | 7/2011 |
|---|---|---|
| WO | WO-2011/133795 A2 | 10/2011 |
| WO | WO-2011133795 A2 | 10/2011 |
| WO | WO-2011/161256 A1 | 12/2011 |
| WO | WO-2012/024433 A2 | 2/2012 |

OTHER PUBLICATIONS

Wolff Manfred 1995 pp. 975-977 (Year: 1995).*
CAPLUS, English Abstract, DN 155;674252, Francik Renata et al. 2011.
Schumacher et al., Synthesis of Didemnolines A-D, N9-Substitued Beta-Carboline Alkaloids from Marine *Ascidian didemnum* sp., 1999.
Cuny et al., "Structure-activity relationship study of beta-carboline derivatives as haspin kinase inhibitors," Bioorganic Medicinal Chemistry Letters, 2012, vol. 22, Issue 5, pp. 2015-2019.
Ellies et al., "Bone Density Ligand, Sclerostin, Directly Interacts with LRP5 but Not LRP5G171v to Modulate Wnt Acitivity," Journal of Bone and Mineral Res., 2006 vol. 21(11), pp. 1738-1749.
Galarreta et al., "The use of natural product scaffolds as leads in the search for trypanothione reductase inhibitors," Bioorganic & Medicinal Chemistry, vol. 16, Issue 14, pp. 6689-6695.
Guan et al., "Design of P-carboline Derivatives as DNA-targeting antitumor agents," 2006, European Journal of Medicinal Chemistry, 41, pp. 1167-1179.
Ishida et al., "Antitumor Agents 201.1 Cytotoxicity of Harmine and p-Carboline Analogs," 1999, Bioorganic & Medicinal Chemistry Letters, 9, pp. 3319-3324.
Jeffcoat, Journal of Oral adn Maxillofacial Implants, 2006, vol. 21, pp. 349-353.
Koretskaya et al., "Synthesis of harmine derivatives," Zhurnal Obshchei Khimii, 1957, vol. 27, pp. 542-545 (English translation "Synthesis of harmine derivatives," The Journal of General Chemistry of the U.S.S.R., Feb. 1957, vol. 27 (2), pp. 611-614).
Kular et al., "An overview of the regulation of bone remodeling at the cellular level," Clinical Biochemistry, 2012, vol. 45, pp. 863-873.
Li et al., "Sclerostin Antibody Treatment Increases Bone Formation, Bone Mass, and Bone Strength in a Rat Model of Postmenopausal Osteoporosis," J. Bone Miner Res., 2009, vol. 24 (4), pp. 578-588.
Vaccaro, Alexander R., "The Role of the Osteoconductive Scaffold in Synthetic Bone Grafth," Ortopedics, May 2002, vol. 25, No. 5/Supplement, pp. s571-s578.
Williams et al., "Medical Progress-Periodontal Disease," New England Journal of Medicine, Feb. 1990, vol. 322(6), pp. 373-382.
Yaffe et al., "Local Delivery of an Amino Bisphosphonate Prevents the Resorptive Phase of Alveolar Bone Following Mucoperiosteal Flap Surgery in Rats," Journal of Periodontology, 1997, vol. 68, pp. 884-889.
PCT application No. PCT/US2014/029582, International Search Report and Written Opinion, dated Sep. 18, 2014, 12 pages.
CAS Registry No. 1026011-30-2, entered STN on Jun. 6, 2008, 1 page.
CAS Registry No. 1028272-52-7, entered STN on Jun. 15, 2018, 1 page.
Schumacher, R.W. et al. (1995). "Didemnolines A-D, New N9-Substituted β-Carbolines from the Marine *Ascidian didemnum* sp," *Tetrahedron* 51(37):10125-10130.
Youssef, D.T. (Jun. 2001). "Alkaloids of the flowers of Hippeastrum vittatum," *J Nat Prod* 64(6):839-841.
CAS Registry 475632-16-7, published on Dec. 11, 2002, 1 page.
Kelly, T.R. et al. (Sep. 24, 1993). "Maxonine: Structure correction and synthesis," *Tetrahedron Letters* 34(39):6173-6176.
Francik, R. et al. (2011). "Antioxidant activity of β-carboline derivatives," *Acta Poloniae Pharmaceutica* 68(2):185-189.
Zhelyazkov, L. et al. (1957). "Synthesis from harmine," *Farmatsiya* (Sofia, Bulgaria) 7(1):29-33. (with English Translation).

* cited by examiner

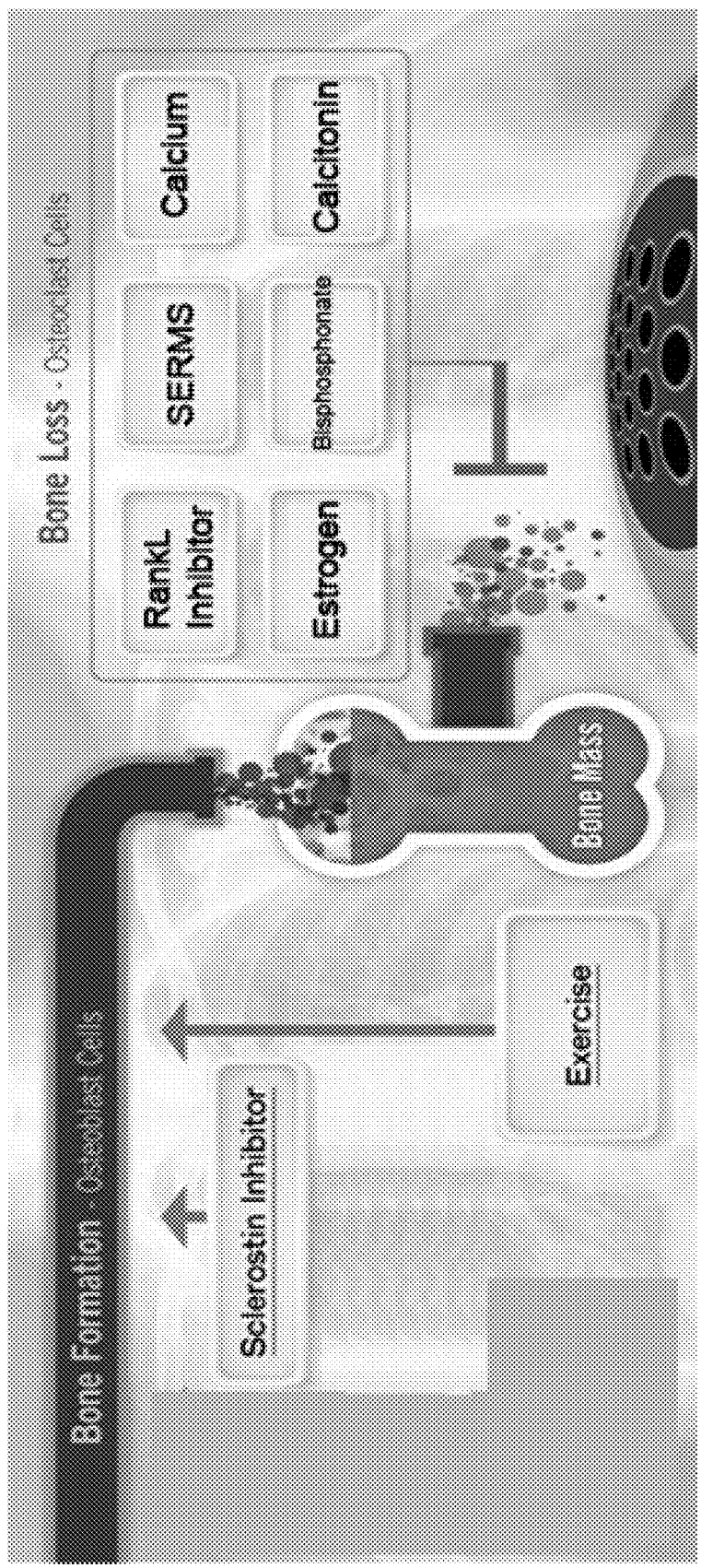

COMPOUNDS FOR BONE GROWTH

CROSS-REFERENCE TO RELATED APPLICATIONS

This application is a continuation of U.S. patent application Ser. No. 14/214,037, filed Mar. 14, 2014, which claims the benefit of U.S. Provisional Application No. 61/785,306, filed Mar. 14, 2013, the entire contents of which are incorporated herein by reference.

STATEMENT AS TO RIGHTS TO INVENTIONS MADE UNDER FEDERALLY SPONSORED RESEARCH AND DEVELOPMENT

NOT APPLICABLE

BACKGROUND OF THE INVENTION

Bone homeostasis involves the counterbalancing processes of bone formation and bone resorption. Increased bone resorption and loss of bone homeostasis is associated with a number of diseases and disorders, such as osteoporosis and Paget's disease.

It is well understood that bone formation is indicated for treatment of a wide variety of disparate disorders in mammals including simple aging, bone degeneration and osteoporosis, fracture healing, fusion or arthrodesis, osteogenesis imperfecta, etc., as well as for successful installation of various medical orthopedic and periodontal implants such as screws, rods, titanium cage for spinal fusion, hip joints, knee joint, ankle joints, shoulder joints, dental plates and rods, etc.

The use of cathepsin K inhibitors, selective estrogen receptor modulators (SERMs), bisphosphonates, and the like for treating a subject with low bone density to treat conditions which may be characterized at least in part by increased bone resorption, such as osteopenia, osteoporosis, arthritis, tumor metastases, osteogenesis imperfecta, Paget's disease, and other metabolic bone disorders, is well known in the art.

Additionally, the use of PTH, TGFβ binding proteins, and like for increasing bone mineralization to treat conditions which may be characterized in part by increased fracture risk, such as osteopenia, degenerative disk disease, bone fractures, osteoporosis, arthritis, tumor metastases, osteogenesis imperfecta, Paget's disease, and other metabolic bone disorders, is known in the art. Demineralized bone matrix is also known to be able to be conducive to small incremements of new bone growth, due the endogenous TGFβ binding proteins (BMPs) surviving the sterilization procedure of the cadaver bone. However, demineralized bone matrix is generally sourced from donor cadaver banks and carries certain risks such as disease transmission or bacterial contamination.

Thus, there remains a need in the art for new methods of treating the bone disorders and to treat bone fractures by fusing bones across a critical size gap, as described above, as well as others. The present invention meets these and other needs.

BRIEF SUMMARY OF THE INVENTION

In one aspect, the present invention provides compounds and compositions, as well as methods of using such compounds and compositions. In a first embodiment, the present invention provides compound of Formula I:

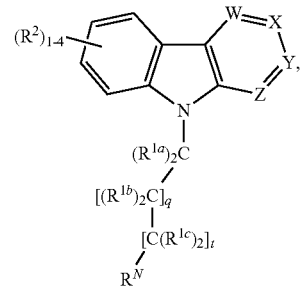

or a salt, hydrate, or isomer thereof; wherein
W is selected from $CR^{3a}$ and N, wherein N is optionally oxidized to the corresponding N-oxide;
X is selected from $CR^{3b}$ and N, wherein N is optionally oxidized to the corresponding N-oxide;
Y is selected from $CR^{3c}$ and N, wherein N is optionally oxidized to the corresponding N-oxide;
Z is selected from $CR^{3d}$ and N, wherein N is optionally oxidized to the corresponding N-oxide;
$R^N$ is selected from the group consisting of $NR^6R^7$, heterocyclyl, and heteroaryl, wherein heterocyclyl and heteroaryl comprise from about 5 to about 10 ring atoms, at least one of which is nitrogen, and wherein any N in $R^N$ is optionally oxidized to the corresponding N-oxide; each $R^{1a}$, $R^{1b}$, and $R^{1c}$ is independently selected from H, methyl, and ethyl, wherein the total number of carbon atoms in the group $-C(R^{1a})_2-[C(R^{1b})_2]_q-[C(R^{1c})_2]_t-$ does not exceed six; each $R^2$, $R^{3a}$, $R^{3b}$, $R^{3c}$ and $R^{3d}$ is independently selected from the group consisting of H, halogen, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, aryloxy, $C_{1-6}$ alkyl-OH, $-OR^4$, $-C_{0-6}$ alkyl-$NR^4R^5$, $-SR^4$, $-C(O)R^4$, $-C_{0-6}$ alkyl-$C(O)OR^4$, $-C(O)NR^4R^5$, $-N(R^4)C(O)R^5$, $-N(R^4)C(O)OR^5$, $-N(R^4)C(O)NR^4R^5$, $-OP(O)(OR^4)_2$, $-S(O)_2OR^4$, $-S(O)_2NR^4R^5$, $-CN$, cycloalkyl, heterocycloalkyl, aryl and heteroaryl; alternatively, two $R^2$ groups on adjacent atoms can be combined with the atoms to which they are attached to form a member selected from the group consisting of cycloalkyl, heterocycloalkyl, aryl and heteroaryl;
each $R^4$, $R^5$, $R^6$, and $R^7$ is independently selected from the group consisting of H, $C_{1-6}$ alkyl, and $C_{1-6}$ alkyl-OH;
the subscript q is an integer from 0 to 4; and
the subscript t is an integer from 0 to 4;
provided that no more than one of W, X, Y, and Z is N or the corresponding N-oxide;
provided that when:
a) the sum of q and t is, 1 and
b) either of $R^6$ or $R^7$, if present, is H or $C_{1-6}$ alkyl,
at least one of $R^{1a}$ and $R^{1b}$ is other than H; and
provided that when the sum of q and t is 2,
a) $R^2$ is other than H, and
b) at least one of $R^6$ and $R^7$, if present, is other than H or methyl.

In some embodiments, a compound of formula I is as described above, provided that the compound is not:
1-amino-3-(3,6-dibromo-9H-carbazol-9-yl)propan-2-ol;
1-(3,6-dibromo-9H-pyrido[3,4-b]indol-9-yl)-3-((3-methoxyphenyl)amino)propan-2-ol;
9-(2-(piperidin-1-yl)ethyl)-9H-pyrido[3,4-b]indole-3-carboxamide;
methyl 9-(4-(dimethylamino)butyl)-9H-pyrido[3,4-b]indole-3-carboxylate;

N,N-dimethyl-4-(9H-pyrido[3,4-b]indol-9-yl)butan-1-amine;
N-ethyl-N-methyl-4-(9H-pyrido[3,4-b]indol-9-yl)butan-1-amine;
2-[4-[7-hydroxy-1-(trifluoromethyl)-9H-pyrido[3,4-b]indol-9-yl]butyl]-1H-Isoindole-1,3(2H)-dione;
2-[4-[7-methoxy-1-(trifluoromethyl)-9H-pyrido[3,4-b]indol-9-yl]butyl]-1H-Isoindole-1,3(2H)-dione;
2-[4-(7-hydroxy-1-methyl-9H-pyrido[3,4-b]indol-9-yl)butyl]-1H-Isoindole-1,3(2H)-dione;
2-[3-(7-methoxy-1-methyl-9H-pyrido[3,4-b]indol-9-yl)propyl]-1H-Isoindole-1,3(2H)-dione;
9-(4-aminobutyl)-1-(trifluoromethyl)-9H-pyrido[3,4-b]indol-7-ol;
7-methoxy-N,N,1-trimethyl-9H-pyrido[3,4-b]indole-9-butanamine;
7-methoxy-N,1-dimethyl-9H-pyrido[3,4-b]indole-9-butanamine;
7-methoxy-1-(trifluoromethyl)-9H-pyrido[3,4-b]indole-9-butanamine;
9-(4-aminobutyl)-1-methyl-9H-pyrido[3,4-b]indol-7-ol;
7-methoxy-9H-pyrido[3,4-b]indole-9-butanamine;
7-methoxy-1-methyl-9H-pyrido[3,4-b]indole-9-butanamine;
7-methoxy-1-methyl-9H-pyrido[3,4-b]indole-9-propanamine;
N,N-dimethyl-N-[3-(7-methoxy-1-methyl-9H-b-carbolin-9-yl)-propyl]amine;
N,N,1,3-tetramethyl-9H-pyrido[3,4-b]indole-9-ethanamine;
N,N-diethyl-7-methoxy-1-methyl-9H-pyrido[3,4-b]indole-9-ethanamine;
7-methoxy-N,N,1-trimethyl-9H-pyrido[3,4-b]indole-9-ethanamine;
4-(7-methoxy-1-methyl-9H-pyrido[3,4-b]indol-9-yl)-N,N-dimethylbutan-1-amine;
4-(7-methoxy-1-methyl-9H-pyrido[3,4-b]indol-9-yl)-N-methylbutan-1-amine;
4-(7-methoxy-1-methyl-9H-pyrido[3,4-b]indol-9-yl)butan-1-amine;
1-(9H-carbazol-9-yl)-N,N-dimethylpropan-2-amine; or
2-(7-methoxy-1-methyl-9H-pyrido[3,4-b]indol-9-yl)-N,N-dimethyl ethanamine.

In a second embodiment, the present invention provides a compound of Formula III:

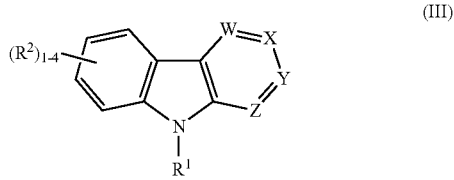

(III)

or a salt, hydrate, or isomer thereof; wherein
$R^1$ is H or $C_{1-6}$ alkyl;
W is selected from $CR^{3a}$ and N, wherein N is optionally oxidized to the corresponding N-oxide;
X is selected from $CR^{3b}$ and N, wherein N is optionally oxidized to the corresponding N-oxide;
Y is $CR^{3c}$;
Z is selected from $CR^{3d}$ and N, wherein N is optionally oxidized to the corresponding N-oxide;
each $R^2$, $R^{3a}$, $R^{3b}$, $R^{1c}$ and $R^{3d}$ is independently selected from the group consisting of H, halogen, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, aryloxy, $C_{1-6}$ alkyl-OH, —$OR^4$, —$C_{0-6}$ alkyl-$NR^4R^5$, —$SR^4$, —$C(O)R^4$, —$C_{0-6}$ alkyl-$C(O)OR^4$, —$C(O)NR^4R^5$, —$N(R^4)C(O)R^5$, —$N(R^4)C(O)OR^5$, —$N(R^4)C(O)NR^4R^5$, —$OP(O)(OR^4)_2$, —$S(O)_2OR^4$, —$S(O)_2NR^4R^5$, —CN, cycloalkyl, heterocycloalkyl, aryl and heteroaryl;
alternatively, two $R^2$ groups on adjacent atoms can be combined with the atoms to which they are attached to form a member selected from the group consisting of cycloalkyl, heterocycloalkyl, aryl and heteroaryl; and
each $R^4$, $R^5$, $R^6$, and $R^7$ is independently selected from the group consisting of H, $C_{1-6}$ alkyl, and $C_{1-6}$ alkyl-OH.

In a third embodiment, the present invention provides a method of promoting bone formation in a subject in need thereof. The method includes administering to the subject a therapeutically effective amount of a compound of Formula I, Formula IA, Formula IB, Formula IC, Formula II, or Formula III as described herein, thereby promoting bone formation in the subject. Bone formation can be systemic or local. For local bone formation, in some embodiments the compound is administered with an osteoconductive agent, e.g., an osteoconductive matrix.

In a fourth embodiment, the present invention provides a method of treating renal damage. The method includes administering to a subject in need thereof, a therapeutically effective amount of a compound of Formula I, Formula IA, Formula IB, Formula IC, Formula II, or Formula III.

In a fifth embodiment, the present invention provides a method of treating cancer. The method includes administering to a subject in need thereof, a therapeutically effective amount of a compound of Formula I, Formula IA, Formula IB, Formula IC, Formula II, or Formula III.

In a sixth embodiment, the present invention provides a medical device, e.g., an orthopedic or periodontal medical device. The device includes a structural support, wherein an implantable portion of the structural support is adapted to be permanently implanted within a subject. The implantable portion is attached to a bone, and the structural support bears at least a partial external coating including a compound of Formula I, Formula IA, Formula IB, Formula IC, Formula II, or Formula III.

In a seventh embodiment, the present invention provides compounds or compositions as described herein (e.g., a compound of composition of Formula I, Formula IA, Formula IB, Formula IC, Formula II, or Formula III) for use in the preparation of a medicament for the treatment of a disease or condition as described herein. In some embodiments, the disease or condition is injured bone, bone fracture, weakened bone, or a condition characterized by low bone mass.

BRIEF DESCRIPTION OF THE DRAWINGS

FIG. 1. Bone mass homeostasis is regulated by the coupled process of bone formation (increasing the amount of bone) and the process of bone resorption (decreasing the amount of bone). Bone formation can be positively promoted by activities and agents that act on the osteoblast bone-forming cell, such as exercise, PTH (teriparatide), or BMPs (TGFβ binding proteins), or by sclerostin inhibitors such as the compounds of the present invention. Bone resorption can be inhibited by antiresorptive agents such as RankL inhibitor, selective estrogen receptor modulator (SERM), calcium, estrogen, bisphosphonates, calcitonin, and other agents acting to stop the activity of the osteoclast cell.

DETAILED DESCRIPTION OF THE INVENTION

I. Introduction

Bone mass homeostasis and bone remodeling involve the counterbalancing processes of bone formation (bone building, an anabolic process) and bone resorption (bone loss, a catabolic process). See, FIG. 1. In bone formation, osteoblasts synthesize bone matrix and regulate mineralization, and then terminally differentiate into osteocytes or bone lining cells. In bone resorption, a different cell type—osteoclasts—remove mineralized bone matrix and break up the organic bone to release calcium in the serum. See, e.g., Kular et al., *Clinical Biochemistry* 45:863-873 (2012).

The osteoblasts (bone formation cells) and osteoclasts (bone resorption cells) are regulated by different mechanisms. Osteoclast cell differentiation is regulated or controlled by the osteoblast (Glass et al., *Dev Cell* 8:751-764 (2005)) or other hormones like PTH, calcitonin, or IL6. In contrast, osteoblast cell differentiation or activity is not regulated or controlled by osteoclast cells, but rather are controlled by different signals, like CPFA, hedgehog, and BMP/Wnt. Bone formation can occur via endochondral ossificiation or intramembranous ossification. In intramembranous ossification, bone forms directly through the stimulation of osteoblast/osteocyte bone cells. In endochondral ossification, bone formation occurs by way of a cartilage template, which increases the amount of time that it takes bone to form. BMP signaling is implicated in endochondral ossification, whereas Wnt signaling has been shown to be involved in both endochondral and intramembranous ossification.

Under normal conditions, bone remodeling (or bone homeostasis) involves the degradation of old bone (via osteoclasts) and the repair or replacement of the old bone with new bone (via osteoblasts). When this homeostasis is disrupted and bone resorption exceeds bone formation, the result is decreased bone mass (loss of trabecular bone) and greater bone fragility (less bone strength). A number of diseases and conditions are associated with increased bone resorption, including osteoporosis, osteogenesis imperfecta, Paget's disease of bone, metabolic bone disease, bone changes secondary to cancer, and other diseases characterized by low bone density.

Diseases associated with decreased bone mass and greater bone fragility are frequently treated with antiresorptive agents such as bisphosphonates, RankL inhibitors, estrogens, cathepsin K inhibitors, and selective estrogen receptor modulators. These agents function by preventing or inhibiting bone resorption, either directly or indirectly. See FIG. 1. However, these agents do not promote the formation of new bone (i.e., anabolic bone formation); in contrast, administration of one dose of an anabolic agent normally results in an annual >3% increase in bone formation in humans). Therefore, although a fragile osteoporotic bone that is treated with an antiresorptive agent will result in the fragile bone not getting more fragile, the fragile bone will not be stronger or have increased strength because the antiresorptive agent does not promote new bone growth by depositing more bone mineral to increase bone density. In contrast, an agent that promotes anabolic bone growth, for example, by stimulating the activity of osteoblasts, promotes the deposition of more bone matrix, or if proliferation were stimulated, the agent would result in more osteoblast cells, thus resulting in more bone cells to bridge a gap to fuse two bones. Thus, a fragile osteoporotic bone treated with an anabolic bone formation agent will allow the bone not to get more fragile, and also will allow the bone to have more strength due to increased bone deposition.

Without being bound to a particular theory, it is believed that compounds of the present invention are SOST (Sclerostin) and/or WISE antagonists that promote anabolic bone formation by modulating the Wnt and BMP signaling pathways. SOST and WISE are proteins that are believed to modulate bone formation by either binding to the Wnt co-receptor LRP, thereby inhibiting the Wnt signaling pathway, or by binding to BMP and inhibiting BMP activity, via different amino acid sequences or domains. By neutralizing the inhibitory effects of SOST and/or WISE proteins on the Wnt pathway, the compounds and compositions of the present invention restore Wnt signaling and promote bone growth. Thus, in one aspect, the present invention provides compounds, compositions, and methods for promoting bone formation in a subject. The bone formation can be systemic or local. The compounds and compositions of the present invention can be administered locally and/or systemically and optionally can be administered sequentially or in combination with one or more other therapeutic agents. In another aspect, the present invention provides implantable devices as structural scaffolds for allowing osteoblast/osteocytes to migrate into the scaffold and deposit bone mineral and also for delivering the compounds and compositions of the present invention, e.g., for promoting bone formation at the site of implantation. In another aspect, the compounds and compositions of the present invention can be used to treat renal damage and cancer.

II. Definitions

As used herein, the term "pharmaceutically acceptable excipient" refers to a substance that aids the administration of an active agent to and absorption by a subject. Pharmaceutically acceptable excipients useful in the present invention include, but are not limited to, binders, fillers, disintegrants, lubricants, coatings, sweeteners, flavors and colors. One of skill in the art will recognize that other pharmaceutical excipients are useful in the present invention.

As used herein, the term "alkyl" refers to a straight or branched, saturated, aliphatic radical having the number of carbon atoms indicated. For example, $C_1$-$C_6$ alkyl includes, but is not limited to, methyl, ethyl, propyl, butyl, pentyl, hexyl, iso-propyl, iso-butyl, sec-butyl, tert-butyl, etc.

Alkylene represents either straight chain or branched alkylene of 1 to 7 carbon atoms, i.e. a divalent hydrocarbon radical of 1 to 7 carbon atoms; for instance, straight chain alkylene being the bivalent radical of Formula —$(CH_2)_n$—, where n is 1, 2, 3, 4, 5, 6 or 7. Preferably alkylene represents straight chain alkylene of 1 to 4 carbon atoms, e.g. a methylene, ethylene, propylene or butylene chain, or the methylene, ethylene, propylene or butylene chain mono-substituted by $C_1$-$C_3$-alkyl (preferably methyl) or disubstituted on the same or different carbon atoms by $C_1$-$C_3$-alkyl (preferably methyl), the total number of carbon atoms being up to and including 7. One of skill in the art will appreciate that a single carbon of the alkylene can be divalent, such as in —$CH((CH_2)_nCH_3)$—, wherein n=0-5.

As used herein, the term "alkoxy" refers to alkyl with the inclusion of an oxygen atom, for example, methoxy, ethoxy, etc. "Haloalkoxy" is as defined for alkoxy where some or all of the hydrogen atoms are substituted with halogen atoms. For example, halo-substituted-alkoxy includes trifluoromethoxy, etc.

As used herein, the term "alkenyl" refers to either a straight chain or branched hydrocarbon of 2 to 6 carbon atoms, having at least one double bond. Examples of alkenyl groups include, but are not limited to, vinyl, propenyl, isopropenyl, butenyl, isobutenyl, butadienyl, pentenyl or hexadienyl.

As used herein, the term "alkynyl" refers to either a straight chain or branched hydrocarbon of 2 to 6 carbon atoms, having at least one triple bond. Examples of alkynyl groups include, but are not limited to, acetylenyl, propynyl or butynyl.

As used herein, the term "halogen" refers to fluorine, chlorine, bromine and iodine.

As used herein, the term "haloalkyl" refers to alkyl as defined above where some or all of the hydrogen atoms are substituted with halogen atoms. Halogen (halo) preferably represents chloro or fluoro, but may also be bromo or iodo. For example, haloalkyl includes trifluoromethyl, fluoromethyl, etc. The term "perfluoro" defines a compound or radical which has at least two available hydrogens substituted with fluorine. For example, perfluoromethane refers to 1,1,1-trifluoromethyl, and perfluoromethoxy refers to 1,1,1-trifluoromethoxy.

As used herein, the term "heteroalkyl" refers to an alkyl group having from 1 to 3 heteroatoms such as N, O and S. Additional heteroatoms can also be useful, including, but not limited to, B, Al, Si and P. The heteroatoms can also be oxidized, such as, but not limited to, —S(O)— and —S(O)$_2$—. For example, heteroalkyl can include ethers, thioethers and alkyl-amines.

As used herein, the term "cycloalkyl" refers to a saturated or partially unsaturated, monocyclic, fused bicyclic or bridged polycyclic ring assembly containing from 3 to 12 ring atoms, or the number of atoms indicated For example, C$_{3-8}$cycloalkyl includes cyclopropyl, cyclobutyl, cyclopentyl, cyclohexyl, and up to cyclooctyl.

As used herein, the terms "heterocycle" and "heterocycloalkyl" refer to a ring system having from 3 ring members to about 20 ring members and from 1 to about 5 heteroatoms such as N, O and S. Additional heteroatoms can also be useful, including, but not limited to, B, Al, Si and P. The heteroatoms can also be oxidized, such as, but not limited to, —S(O)— and —S(O)$_2$—. For example, heterocycle includes, but is not limited to, tetrahydrofuranyl, tetrahydrothiophenyl, morpholino, pyrrolidinyl, pyrrolinyl, imidazolidinyl, imidazolinyl, pyrazolidinyl, pyrazolinyl, piperazinyl, piperidinyl, indolinyl, quinuclidinyl and 1,4-dioxa-8-aza-spiro[4.5]dec-8-yl.

As used herein, a group "linked via a carbon atom" refers to a linkage between a carbon atom of the referenced group and the rest of the molecule. A group "linked via a nitrogen atom" refers to a linkage between a nitrogen atom of the referenced group and the rest of the molecule. By way of example only, a heterocyclyl group linked via a carbon atom may be:

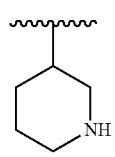

where the wavy line indicates the point of attachment to the rest of the molecule. By way of example only, a heterocyclyl group linked via a carbon atom may be:

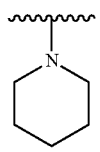

where the wavy line indicates the point of attachment to the rest of the molecule.

As used herein, where a referenced compound is an N-oxide, it comprises an N—O bond with three additional bonds to the nitrogen, i.e., an N-oxide refers to a group R$_3$N$^+$—O$^-$. By way of example only, N-oxides may include:

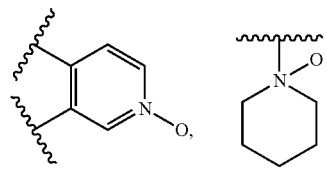

and the like.

As used herein, the term "aryl" refers to a monocyclic or fused bicyclic, tricyclic or greater, aromatic ring assembly containing 6 to 16 ring carbon atoms. For example, aryl may be phenyl, benzyl or naphthyl, preferably phenyl. "Arylene" means a divalent radical derived from an aryl group. Aryl groups can be mono-, di- or tri-substituted by one, two or three radicals selected from alkyl, alkoxy, aryl, hydroxy, halogen, cyano, amino, amino-alkyl, trifluoromethyl, alkylenedioxy and oxy-C$_2$-C$_3$-alkylene; all of which are optionally further substituted, for instance as hereinbefore defined; or 1- or 2-naphthyl; or 1- or 2-phenanthrenyl. Alkylenedioxy is a divalent substitute attached to two adjacent carbon atoms of phenyl, e.g. methylenedioxy or ethylenedioxy. Oxy-C$_2$-C$_3$-alkylene is also a divalent substituent attached to two adjacent carbon atoms of phenyl, e.g. oxyethylene or oxypropylene. An example for oxy-C$_2$-C$_3$-alkylene-phenyl is 2,3-dihydrobenzofuran-5-yl.

Preferred as aryl is naphthyl, phenyl or phenyl mono- or disubstituted by alkoxy, phenyl, halogen, alkyl or trifluoromethyl, especially phenyl or phenyl-mono- or disubstituted by alkoxy, halogen or trifluoromethyl, and in particular phenyl.

Examples of substituted phenyl groups as R are, e.g. 4-chlorophen-1-yl, 3,4-dichlorophen-1-yl, 4-methoxyphen-1-yl, 4-methylphen-1-yl, 4-aminomethylphen-1-yl, 4-methoxyethylaminomethylphen-1-yl, 4-hydroxyethylaminomethylphen-1-yl, 4-hydroxyethyl-(methyl)-aminomethylphen-1-yl, 3-aminomethylphen-1-yl, 4-N-acetylaminomethylphen-1-yl, 4-aminophen-1-yl, 3-aminophen-1-yl, 2-aminophen-1-yl, 4-phenyl-phen-1-yl, 4-(imidazol-1-yl)-phen-yl, 4-(imidazol-1-ylmethyl)-phen-1-yl, 4-(morpholin-1-yl)-phen-1-yl, 4-(morpholin-1-ylmethyl)-phen-1-yl, 4-(2-methoxyethylaminomethyl)-phen-1-yl and 4-(pyrrolidin-1-ylmethyl)-phen-1-yl, 4-(thiophenyl)-phen-1-yl, 4-(3-thiophenyl)-phen-1-yl, 4-(4-methylpiperazin-1-yl)-phen-1-yl, and 4-(piperidinyl)-phenyl and 4-(pyridinyl)-phenyl optionally substituted in the heterocyclic ring.

As used herein, the term "heteroaryl" refers to a monocyclic or fused bicyclic or tricyclic aromatic ring assembly containing 5 to 16 ring atoms, where from 1 to 4 of the ring atoms are a heteroatom each N, O or S. For example, heteroaryl includes pyridyl, indolyl, indazolyl, quinoxalinyl, quinolinyl, isoquinolinyl, benzothienyl, benzofuranyl, furanyl, pyrrolyl, thiazolyl, benzothiazolyl, oxazolyl, isoxazolyl, triazolyl, tetrazolyl, pyrazolyl, imidazolyl, thienyl, or any other radicals substituted, especially mono- or di-substituted, by e.g. alkyl, nitro or halogen. Pyridyl represents 2-, 3- or 4-pyridyl, advantageously 2- or 3-pyridyl. Thienyl represents 2- or 3-thienyl. Quinolinyl represents preferably 2-, 3- or 4-quinolinyl. Isoquinolinyl represents preferably 1-, 3- or 4-isoquinolinyl. Benzopyranyl, benzothiopyranyl represents preferably 3-benzopyranyl or 3-benzothiopyranyl, respectively. Thiazolyl represents preferably 2- or 4-thiazolyl, and most preferred, 4-thiazolyl. Triazolyl is preferably 1-, 2- or 5-(1,2,4-triazolyl). Tetrazolyl is preferably 5-tetrazolyl.

Preferably, heteroaryl is pyridyl, indolyl, quinolinyl, pyrrolyl, thiazolyl, isoxazolyl, triazolyl, tetrazolyl, pyrazolyl, imidazolyl, thienyl, furanyl, benzothiazolyl, benzofuranyl, isoquinolinyl, benzothienyl, oxazolyl, indazolyl, or any of the radicals substituted, especially mono- or di-substituted.

Substituents for the aryl and heteroaryl groups are varied and are selected from: -halogen, —OR', —OC(O)R', —NR'R—SR', —R', —CN, —NO$_2$, —CONR'R", —C(O)R', —OC(O)NR'R", —NR"C(O)R', —NR"C(O)$_2$R', —NR'—C(O)NR"R''', —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro(C$_1$-C$_4$)alkoxy, and perfluoro(C$_1$-C$_4$)alkyl, in a number ranging from zero to the total number of open valences on the aromatic ring system; and where R', R" and R''' are independently selected from hydrogen, (C$_1$-C$_8$)alkyl and heteroalkyl, unsubstituted aryl and heteroaryl, (unsubstituted aryl)-(C$_1$-C$_4$)alkyl, and (unsubstituted aryl)oxy-(C$_1$-C$_4$)alkyl.

As used herein, the term "salt" refers to acid or base salts of the compounds used in the methods of the present invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

Pharmaceutically acceptable salts of the acidic compounds of the present invention are salts formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymethyl)-methyl-ammonium salts.

Similarly, acid addition salts, such as of mineral acids, organic carboxylic and organic sulfonic acids, e.g., hydrochloric acid, methanesulfonic acid, maleic acid, are also possible provided a basic group, such as pyridyl, constitutes part of the structure.

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

As used herein, the term "calcium salt" refers to salts containing calcium. Examples of calcium salts include, but are not limited to, calcium acetate, calcium aluminates, calcium aluminosilicate, calcium arsenate, calcium borate, calcium bromide, calcium carbide, calcium carbonate, calcium chlorate, calcium chloride, calcium citrate, calcium citrate malate, calcium cyanamide, calcium dihydrogen phosphate, calcium fluoride, calcium formate, calcium glubionate, calcium glucoheptonate, calcium gluconate, calcium glycerylphosphate, calcium hexaboride, calcium hydride, calcium hydroxide, calcium hypochlorite, calcium inosinate, calcium iodate, calcium iodide, calcium lactate, calcium lactate gluconate, calcium magnesium acetate, calcium malate, calcium nitrate, calcium nitride, calcium oxalate, calcium oxide, calcium pangamate, calcium peroxide, calcium phosphate, calcium phosphide, calcium propionate, calcium pyrophosphate, calcium silicate, calcium silicide, calcium sorbate, calcium stearate, calcium sulfate, calcium sulfide, calcium tartrate, calcium(I) chloride, dicalcium citrate, dicalcium phosphate, dodecacalcium heptaaluminate, tricalcium aluminate, tricalcium phosphate and triple superphosphate. One of skill in the art will appreciate that other calcium salts are useful in the present invention.

As used herein, the term "hydrate" refers to a compound that is complexed to at least one water molecule. The compounds of the present invention can be complexed with from 1 to 10 water molecules.

Certain compounds of the present invention possess asymmetric carbon atoms (optical centers) or double bonds; the racemates, diastereomers, geometric isomers and individual isomers are all intended to be encompassed within the scope of the present invention.

As used herein, the term "subject" refers to animals such as mammals, including, but not limited to, primates (e.g., humans), cows, sheep, goats, horses, dogs, cats, rabbits, rats, mice and the like. In certain embodiments, the subject is a human.

As used herein, the terms "therapeutically effective amount or dose" or "therapeutically sufficient amount or dose" or "effective or sufficient amount or dose" refer to a dose that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins). In sensitized cells, the therapeutically effective dose can often be lower than the conventional therapeutically effective dose for non-sensitized cells.

As used herein, the term "site of injury or localized condition" refers to a specific location in the subject's body that is in need of treatment by the method of the present invention. For example, the injury can be a fracture and the localized condition can be a disease state (such as osteoporosis, etc.) that is limited to a particular location in the subject's body, such as a particular bone, joint, digit, hand, foot, limb, spine, head, torso, etc. In some embodiments, the site of injury or localized condition is a surgical implantation site.

As used herein, the term "promoting bone formation" refers to stimulating new bone formation, growing bone across a joint or gap, enhancing or hastening bone formation, and/or increasing bone density or bone mineral content. In some embodiments, a compound promotes bone formation if it increases the amount of bone in a sample by at least 5%, 6%, 7%, 8%, 9%, 10%, 15%, or more relative to a control sample (e.g., a sample that has not been contacted with the compound).

As used herein, the term "arthrodesis" refers to the artificial induction of joint ossification between two bones and/or across a joint, often via surgery. Arthrodesis can be accomplished via bone graft, metal implants or the use of synthetic bone substitutes, among others.

As used herein, the term "bone autograft" refers to the grafting of a subject's own bone.

As used herein, the term "bone allograft" refers to the grafting of bone from one person to another person.

As used herein, the term "antiresorptive drug" refers to drugs that slow or block the resorption of bone and/or that act on the osteoclast cell.

As used herein, the term "bone related disease characterized by low bone mass" refers to bone having a T-score less than −0.5. Other methods of determining low bone mass are known by one of skill in the art.

As used herein, the term "bone fracture" refers to bone that has been cracked or broken.

As used herein, the term "spinal fusion" refers to a surgical technique for combining two or more vertebrae.

As used herein, the term "structural support" refers to a segment of a device that can be implanted in a subject (implantable portion). The structural support can be prepared from a variety of different materials, including metals, ceramics, polymers and inorganic materials, such as described below. The structural support can be coated with a variety of materials that promote bone growth. In some embodiments, the entire device comprises an implantable structural support. For example, in some embodiments, an entire device as described herein can be implanted at a surgical site and the surgical site can be closed over the device.

As used herein, the term "external coating" refers to a coating of the structural support that can cover only a portion of the structural support (partial external coating) or cover the entire structural support. For example, the partial external coating can completely cover only the implantable portion of the structural support.

As used herein, the term "weakened bone" refers to bone that has a T score of less than −0.5 (less than 0.9 g/cm2).

As used herein, the term "demineralized bone" refers to bone from which the inorganic mineral have been removed. The remaining organic collagen material may contain the osteoinductive growth factors. These growth factors include bone morphogenetic proteins that induce cartilage which then ossify via endochondral ossification to generate new bone formation. Demineralized bone often comes in the form of "demineralized bone matrix (DBM)." DBM can be made by fresh frozen or freeze dried bulk bone allograft, or can be made from mild acid extraction of cadaveric bone that removes the mineral phase, leaving collagen, growth factors, and noncollagenous proteins that offer the intrinsic properties of osteoconduction. DBM can also be processed in a variety of ways, ultimately resulting in a powder that is mixed with a carrier to provide the optimum handling characteristics desired by a surgeon. DBM is clinically available in gels, pastes, putty, and fabrics that have been tailored to meet the needs of the surgical procedure. Some DBM are mixed with antibiotics prior to the surgical procedure.

As used herein, the term "renal damage" refers to the inability of the kidneys to excrete waste and to help maintain the electrolyte balance of the body. Renal damage is characterized by some of the following: high blood pressure, accumulation of urea and formation of uremic frost, accumulation of potassium in the blood, decrease in erythropoietin synthesis, increase in fluid volume, hyperphosphatemia, and metabolic acidosis, among others.

As used herein, the term "osteoconductive matrix" refers to a material that can act as an osteoconductive substrate (i.e., permits bone growth) and has a scaffolding structure on which infiltrating cells can attach, proliferate, and participate in the process of producing osteoid, the organic phase of bone, culminating in osteoneogenesis, or new bone formation. The terms "matrix" and "scaffold" interchangeably refer to a structural component or substrate intrinsically having a 3 dimensional form upon which the specific cellular events involved in bone formation will occur. The osteoconductive matrix allows for the ingrowth of host capillaries, perivascular tissue and osteoprogenitor cells. In some embodiments, an osteoconductive matrix includes an "osteoinductive agent" for providing osteogenic potential. An osteoinductive agent, as used herein, is an agent that stimulates the host to multiply bone cells, thus producing more bone osteoid.

As used herein, the terms "treat," "treating," and "treatment" refers to any indicia of success in the treatment or amelioration of an injury, pathology, condition, or symptom (e.g., pain), including any objective or subjective parameter such as abatement; remission; diminishing of symptoms or making the symptom, injury, pathology or condition more tolerable to the patient; decreasing the frequency or duration of the symptom or condition; or, in some situations, preventing the onset of the symptom or condition. The treatment or amelioration of symptoms can be based on any objective or subjective parameter; including, e.g., the result of a physical examination.

As used herein, the term "RankL inhibitor" refers to compounds or agents that inhibit the activity of RankL. RankL (Receptor Activator for Nuclear Factor κ B Ligand), is important in bone metabolism by activating osteoclasts. RankL inhibitors include, but are not limited to, the human monoclonal antibody denosumab. One of skill in the art will appreciate that other RankL inhibitors are useful in the present invention.

III. Compounds and Compositions

The compounds useful in the methods of the present invention include harmine and harmine derivatives. Accordingly, some embodiments of the invention provide a compound according to Formula I:

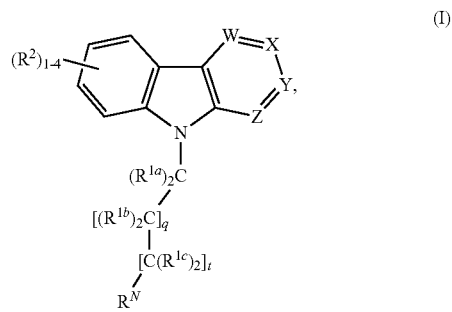

or a salt, hydrate, or isomer thereof; wherein:
W is selected from $CR^{3a}$ and N, wherein N is optionally oxidized to the corresponding N-oxide;

X is selected from $CR^{3b}$ and N, wherein N is optionally oxidized to the corresponding N-oxide;
Y is selected from $CR^{3c}$ and N, wherein N is optionally oxidized to the corresponding N-oxide;
Z is selected from $CR^{3d}$ and N, wherein N is optionally oxidized to the corresponding N-oxide;
$R^N$ is selected from the group consisting of $NR^6R^7$, heterocyclyl, and heteroaryl, wherein heterocyclyl and heteroaryl comprise from about 5 to about 10 ring atoms, at least one of which is nitrogen, and wherein any N in $R^N$ is optionally oxidized to the corresponding N-oxide;
each $R^{1a}$, $R^{1b}$, and $R^{1c}$ is independently selected from H, methyl, and ethyl, wherein the total number of carbon atoms in the group —$C(R^{1a})_2$—$[C(R^{1b})_2]_q$—$[C(R^{1c})_2]_t$— does not exceed six; each $R^2$, $R^{3a}$, $R^{3b}$, $R^{1c}$ and $R^{3d}$ is independently selected from the group consisting of H, halogen, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$haloalkoxy, aryloxy, $C_{1-6}$ alkyl-OH, —$OR^4$, —$C_{0-6}$ alkyl-$NR^4R^5$, —$SR^4$, —$C(O)R^4$, —$C_{0-6}$ alkyl-$C(O)OR^4$, —$C(O)NR^4R^5$, —$N(R^4)C(O)R^5$, —$N(R^4)C(O)OR^5$, —$N(R^4)C(O)NR^4R^5$, —$OP(O)(OR^4)_2$, —$S(O)_2OR^4$, —$S(O)_2NR^4R^5$, —CN, cycloalkyl, heterocycloalkyl, aryl and heteroaryl;
alternatively, two $R^2$ groups on adjacent atoms can be combined with the atoms to which they are attached to form a member selected from the group consisting of cycloalkyl, heterocycloalkyl, aryl and heteroaryl;
each $R^4$, $R^5$, $R^6$, and $R^7$ is independently selected from the group consisting of H, $C_{1-6}$ alkyl, and $C_{1-6}$ alkyl-OH;
the subscript q is an integer from 0 to 4; and
the subscript t is an integer from 0 to 4;
provided that no more than one of W, X, Y, and Z is N or the corresponding N-oxide;
provided that when:
a) the sum of q and t is 1, and
b) either of $R^6$ or $R^7$, if present, is H or $C_{1-6}$ alkyl,
at least one of $R^{1a}$ and $R^{1b}$ is other than H; and
provided that when the sum of q and t is 2,
a) $R^2$ is other than H, and
b) at least one of $R^6$ and $R^7$, if present, is other than H or methyl.

In some embodiments, the invention provides a compound according to Formula I:

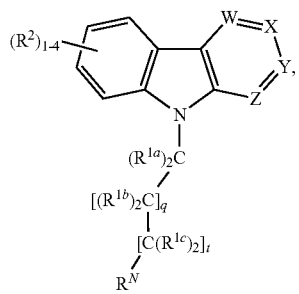

(I)

or a salt, hydrate, or isomer thereof; wherein:
W is selected from $CR^{3a}$ and N, wherein N is optionally oxidized to the corresponding N-oxide;
X is selected from $CR^{3b}$ and N, wherein N is optionally oxidized to the corresponding N-oxide;
Y is selected from $CR^{3c}$ and N, wherein N is optionally oxidized to the corresponding N-oxide;
Z is selected from $CR^{3d}$ and N, wherein N is optionally oxidized to the corresponding N-oxide;

$R^N$ is selected from the group consisting of $NR^6R^7$, heterocyclyl, and heteroaryl, wherein heterocyclyl and heteroaryl comprise from about 5 to about 10 ring atoms, at least one of which is nitrogen, and wherein any N in $R^N$ is optionally oxidized to the corresponding N-oxide;
each $R^{1a}$, $R^{1b}$, and $R^{1c}$ is independently selected from H, methyl, and ethyl, wherein the total number of carbon atoms in the group —$C(R^{1a})_2$—$[C(R^{1b})_2]_q$—$[C(R^{1c})_2]_t$— does not exceed six; each $R^2$, $R^{3a}$, $R^{3b}$, $R^{1c}$ and $R^{3d}$ is independently selected from the group consisting of H, halogen, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, aryloxy, $C_{1-6}$ alkyl-OH, —$OR^4$, —$C_{0-6}$ alkyl-$NR^4R^5$, —$SR^4$, —$C(O)R^4$, —$C_{0-6}$ alkyl-$C(O)OR^4$, —$C(O)NR^4R^5$, —$N(R^4)C(O)R^5$, —$N(R^4)C(O)OR^5$, —$N(R^4)C(O)NR^4R^5$, —$OP(O)(OR^4)_2$, —$S(O)_2OR^4$, —$S(O)_2NR^4R^5$, —CN, cycloalkyl, heterocycloalkyl, aryl and heteroaryl;
alternatively, two $R^2$ groups on adjacent atoms can be combined with the atoms to which they are attached to form a member selected from the group consisting of cycloalkyl, heterocycloalkyl, aryl and heteroaryl;
each $R^4$, $R^5$, $R^6$, and $R^7$ is independently selected from the group consisting of H, $C_{1-6}$ alkyl, $C_{1-6}$ alkyl-OH, and $C_{1-6}$ alkyl-O—$C_{1-6}$ alkyl;
the subscript q is an integer from 0 to 4; and
the subscript t is an integer from 0 to 4;
provided that no more than one of W, X, Y, and Z is N or the corresponding N-oxide;
provided that when:
a) the sum of q and t is 1, and
b) either of $R^6$ or $R^7$, if present, is H or $C_{1-6}$ alkyl,
at least one of $R^{1a}$ and $R^{1b}$ is other than H; and
provided that when:
a) the sum of q and t is 1, and
b) $R^N$ is heterocyclyl,
at least one $R^2$ is other than H; and
provided that when the sum of q and t is 2,
a) at least one $R^2$ is other than H,
b) $R^N$ is not phthalimido, and
c) at least one of $R^6$ and $R^7$, if present, is other than H or methyl; and
provided that when:
a) the sum of q and t is 3, and
b) each of $R^{1a}$, $R^{1b}$, and $R^{1c}$ is H,
$R^N$ is not phthalimido and at least one of $R^6$ and $R^7$, if present, is other than H, methyl, and ethyl.

In certain embodiments, the invention provides compounds of formula I as described above, provided that the compound is not:
1-amino-3-(3,6-dibromo-9H-carbazol-9-yl)propan-2-ol;
1-(3,6-dibromo-9H-pyrido[3,4-b]indol-9-yl)-3-((3-methoxyphenyl)amino)propan-2-ol;
9-(2-(piperidin-1-yl)ethyl)-9H-pyrido[3,4-b]indole-3-carboxamide;
methyl 9-(4-(dimethylamino)butyl)-9H-pyrido[3,4-b]indole-3-carboxylate;
N,N-dimethyl-4-(9H-pyrido[3,4-b]indol-9-yl)butan-1-amine;
N-ethyl-N-methyl-4-(9H-pyrido[3,4-b]indol-9-yl)butan-1-amine;
2-[4-[7-hydroxy-1-(trifluoromethyl)-9H-pyrido[3,4-b]indol-9-yl]butyl]-1H-Isoindole-1,3(2H)-dione;
2-[4-[7-methoxy-1-(trifluoromethyl)-9H-pyrido[3,4-b]indol-9-yl]butyl]-1H-Isoindole-1,3(2H)-dione;
2-[4-(7-hydroxy-1-methyl-9H-pyrido[3,4-b]indol-9-yl)butyl]-1H-Isoindole-1,3(2H)-dione;
2-[3-(7-methoxy-1-methyl-9H-pyrido[3,4-b]indol-9-yl)propyl]-1H-Isoindole-1,3(2H)-dione;

9-(4-aminobutyl)-1-(trifluoromethyl)-9H-pyrido[3,4-b]indol-7-ol;
7-methoxy-N,N,1-trimethyl-9H-pyrido[3,4-b]indole-9-butanamine;
7-methoxy-N,1-dimethyl-9H-pyrido[3,4-b]indole-9-butanamine;
7-methoxy-1-(trifluoromethyl)-9H-pyrido[3,4-b]indole-9-butanamine;
9-(4-aminobutyl)-1-methyl-9H-pyrido[3,4-b]indol-7-ol;
7-methoxy-9H-pyrido[3,4-b]indole-9-butanamine;
7-methoxy-1-methyl-9H-pyrido[3,4-b]indole-9-butanamine;
7-methoxy-1-methyl-9H-pyrido[3,4-b]indole-9-propanamine;
N,N-dimethyl-N-[3-(7-methoxy-1-methyl-9H-b-carbolin-9-yl)-propyl]amine;
N,N,1,3-tetramethyl-9H-pyrido[3,4-b]indole-9-ethanamine;
N,N-diethyl-7-methoxy-1-methyl-9H-pyrido[3,4-b]indole-9-ethanamine;
7-methoxy-N,N,1-trimethyl-9H-pyrido[3,4-b]indole-9-ethanamine;
4-(7-methoxy-1-methyl-9H-pyrido[3,4-b]indol-9-yl)-N,N-dimethylbutan-1-amine;
4-(7-methoxy-1-methyl-9H-pyrido[3,4-b]indol-9-yl)-N-methylbutan-1-amine;
4-(7-methoxy-1-methyl-9H-pyrido[3,4-b]indol-9-yl)butan-1-amine;
1-(9H-carbazol-9-yl)-N,N-dimethylpropan-2-amine; or
2-(7-methoxy-1-methyl-9H-pyrido[3,4-b]indol-9-yl)-N,N-dimethyl ethanamine.

In certain embodiments, the compound is not a dihydro beta-carboline derivative or a tetrahydro gamma-carboline derivative.

Some additional embodiments of the invention provide a compound according to Formula IA:

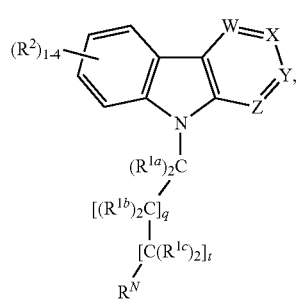

(IA)

or a salt, hydrate, or isomer thereof; wherein:
W is selected from $CR^{3a}$ and N, wherein N is optionally oxidized to the corresponding N-oxide;
X is selected from $CR^{3b}$ and N, wherein N is optionally oxidized to the corresponding N-oxide;
Y is selected from $CR^{3c}$ and N, wherein N is optionally oxidized to the corresponding N-oxide;
Z is selected from $CR^{3d}$ and N, wherein N is optionally oxidized to the corresponding N-oxide;
$R^N$ is selected from the group consisting of $NR^6R^7$, heterocyclyl, and heteroaryl, wherein heterocyclyl and heteroaryl comprise from about 5 to about 10 ring atoms, at least one of which is nitrogen, and wherein any N in $R^N$ is optionally oxidized to the corresponding N-oxide;
each $R^{1a}$, $R^{1b}$, and $R^{1c}$ is independently selected from H, methyl, and ethyl, wherein the total number of carbon atoms in the group $—C(R^{1a})_2—[C(R^{1b})_2]_q—[C(R^{1c})_2]_t—$ does not exceed six; each $R^2$, $R^{3a}$, $R^{3b}$, $R^{1c}$ and $R^{3d}$ is independently selected from the group consisting of H, halogen, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$haloalkoxy, aryloxy, $C_{1-6}$ alkyl-OH, $—OR^4$, $—C_{0-6}$ alkyl-$NR^4R^5$, $—SR^4$, $—C(O)R^4$, $—C_{0-6}$ alkyl-$C(O)OR^4$, $—C(O)NR^4R^5$, $—N(R^4)C(O)R^5$, $—N(R^4)C(O)OR^5$, $—N(R^4)C(O)NR^4R^5$, $—OP(O)(OR^4)_2$, $—S(O)_2OR^4$, $—S(O)_2NR^4R^5$, $—CN$, cycloalkyl, heterocycloalkyl, aryl and heteroaryl;
alternatively, two $R^2$ groups on adjacent atoms can be combined with the atoms to which they are attached to form a member selected from the group consisting of cycloalkyl, heterocycloalkyl, aryl and heteroaryl;
each $R^4$, $R^5$, $R^6$, and $R^7$ is independently selected from the group consisting of H, $C_{1-6}$ alkyl, and $C_{1-6}$ alkyl-OH;
the subscript q is an integer from 0 to 4; and
the subscript t is an integer from 0 to 4; and
provided that no more than one of W, X, Y, and Z is N or the corresponding N-oxide.

In some embodiments, the invention provides a compound of Formula I having the structure

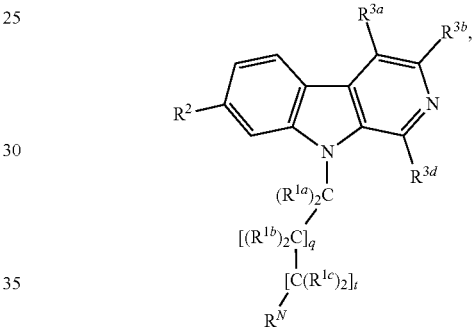

or a salt, hydrate, or isomer thereof; wherein:
$R^2$ is selected from the group consisting of H, $C_{1-6}$ alkoxy, $—OH$, and $C_{1-6}$ alkyl-OH;
$R^{3a}$ and $R^{3b}$ are independently selected from the group consisting of H, halo, $C_{1-6}$ alkoxy, $—OH$, and
$R^{3d}$ is selected from the group consisting of H, $C_{1-6}$ alkyl and $C_{1-6}$ haloalkyl.

In some embodiments, the invention provides a compound of Formula I having the structure

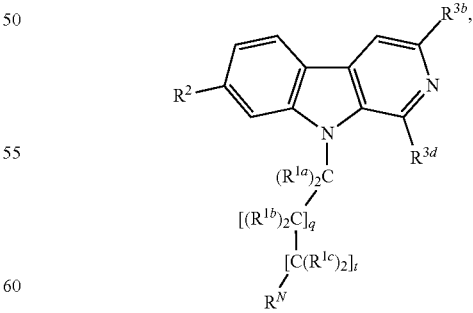

or a salt, hydrate, or isomer thereof; wherein:
$R^2$ is selected from the group consisting of H, $C_{1-6}$ alkoxy, $—OH$, and $C_{1-6}$ alkyl-OH;
$R^{3b}$ is selected from the group consisting of H, halo, $C_{1-6}$ alkoxy, $—OH$, and $R^{3d}$ is selected from the group consisting of H, $C_{1-6}$ alkyl and $C_{1-6}$ haloalkyl.

In some embodiments, a compound of formula (I) is one of the following compounds:

(A) In some embodiments, the invention provides a compound wherein:

$R^2$ is selected from the group consisting of OH and methoxy; and $R^{3a}$, $R^{3b}$, and $R^{3d}$ are H;

or a salt, hydrate, or isomer thereof.

(B) In some embodiments, the invention provides a compound wherein:

$R^2$ is selected from the group consisting of methoxy and —OH;

$R^{3a}$ and $R^{3b}$ are H; and $R^{3d}$ is selected from the group consisting of methyl, methoxy and trifluoromethyl; preferably $R^{3d}$ is methyl or trifluoromethyl;

or a salt, hydrate, or isomer thereof.

(C) In some embodiments, the invention provides a compound wherein:

$R^2$ is selected from the group consisting of methoxy and —OH;

$R^{3a}$ and $R^{3d}$ are H; and $R^{3b}$ is selected from the group consisting of F, Cl, Br and I; preferably $R^{3b}$ is F;

or a salt, hydrate, or isomer thereof.

(D) In some embodiments, the invention provides a compound wherein:

$R^2$ is selected from the group consisting of methoxy and —OH;

$R^{3a}$ is H;

and $R^{3b}$ is selected from the group consisting of F, —OH, and methoxy;

or a salt, hydrate, or isomer thereof.

(E) In some embodiments, the invention provides a compound wherein $R^2$ is selected from the group consisting of methoxy and —OH; and $R^{3a}$ and $R^{3b}$ are H; or a salt, hydrate, or isomer thereof.

(F) In some embodiments, the invention provides a compound wherein:

$R^2$ is selected from the group consisting of H and methoxy; and $R^{3a}$ is H;

$R^{3b}$ is F, Cl, Br or I; preferably, $R^{3b}$ is F; and $R^{3d}$ is methyl;

or a salt, hydrate, or isomer thereof.

For any of the embodiments (A), (B), (C), (D), (E) or (F) described above, in one group of embodiments, $R^2$ is OH and $R^{3a}$, $R^{3b}$ and $R^{3d}$ are as described above. For any of the embodiments (A), (B), (C), (D), (E) or (F) described above, in a second group of embodiments, $R^2$ is methoxy and $R^{3a}$, $R^{3b}$ and $R^{3d}$ are as described above. For any of the embodiments (A), (B), (C), (D), (E) or (F) described above, in one group of embodiments, the nitrogen at the Z position is oxidized to an N-oxide.

In one group of embodiments are compounds of formula (I) having a structure selected from the following:

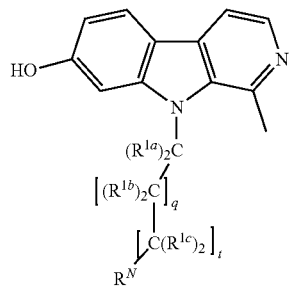

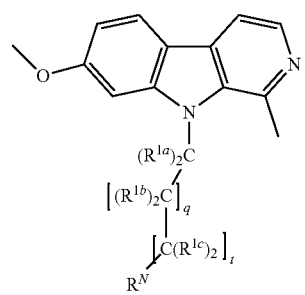

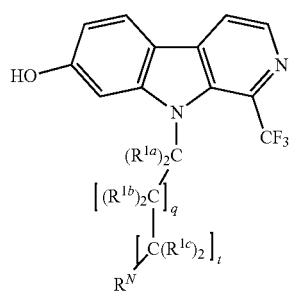

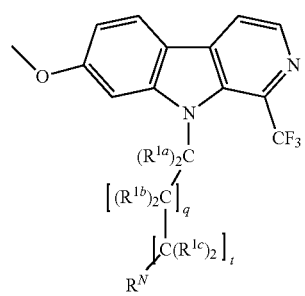

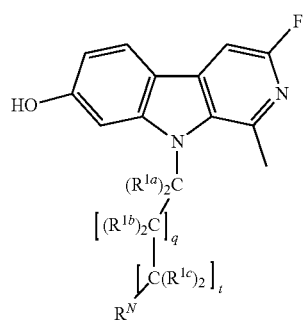

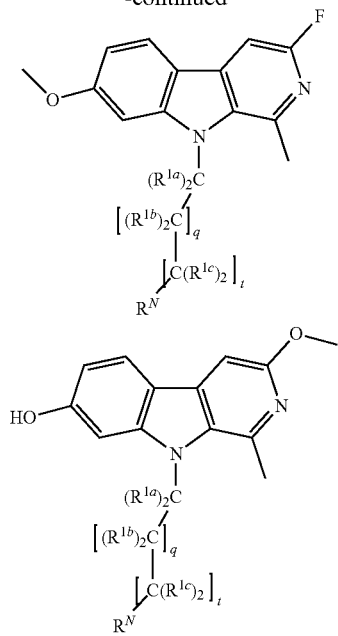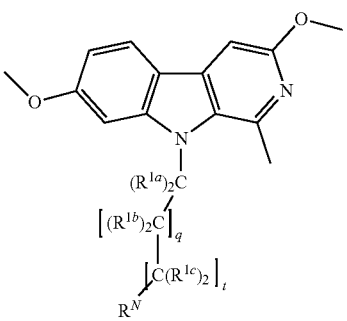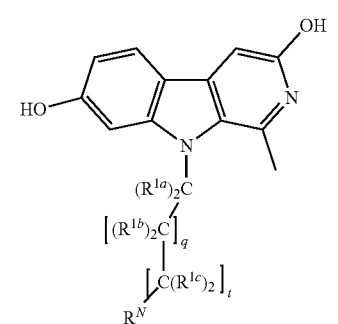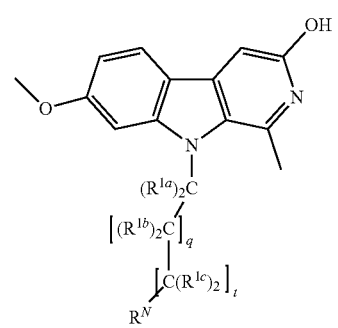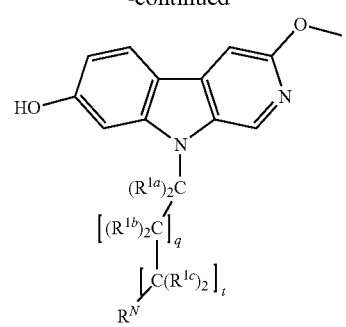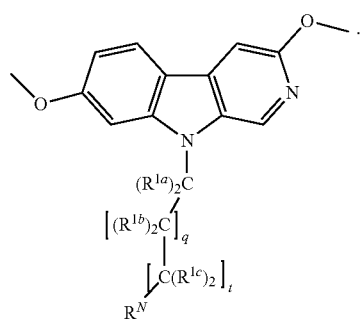
For each structure described above, in one group of embodiments,
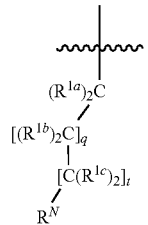
is selected from the following:
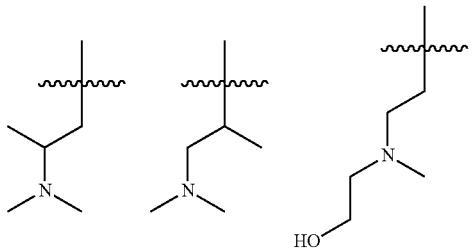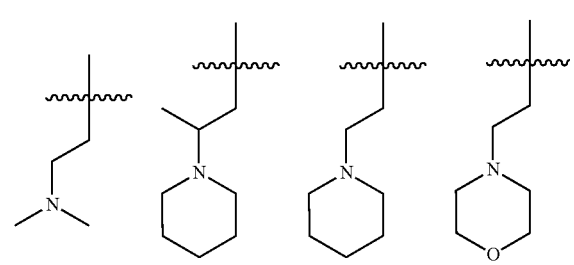

-continued

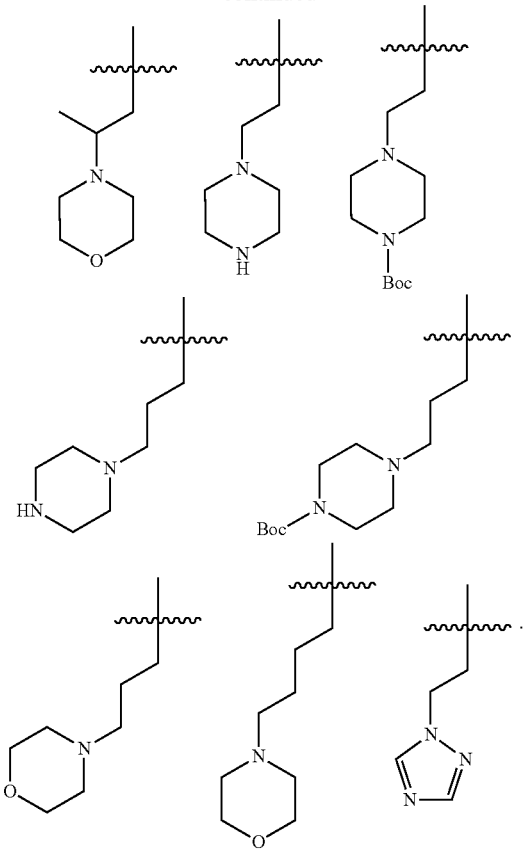

In some embodiments, the invention provides a compound wherein the N at the Z position is oxidized to the corresponding N-oxide; or a salt, hydrate, or isomer thereof.

In some embodiments, the invention provides a compound wherein:
$R^{3a}$ is selected from the group consisting of F and —OH; and $R^{3b}$ is H;
or a salt, hydrate, or isomer thereof.

In some embodiments, the invention provides a compound having the structure:

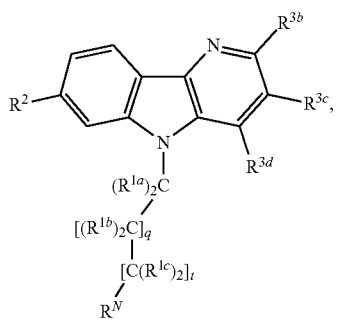

or a salt, hydrate, or isomer thereof; wherein:
$R^2$ is selected from the group consisting of H, $C_{1-6}$ alkoxy, —OH, and $C_{1-6}$ alkyl-OH;
$R^{3b}$ and $R^{1c}$ are independently selected from the group consisting of H, halo, $C_{1-6}$ alkoxy, —OH, and
$R^{3d}$ is selected from the group consisting of H, $C_{1-6}$ alkyl and $C_{1-6}$ haloalkyl.

In some embodiments, the invention provides a compound wherein:
$R^2$ is methoxy;
$R^{3d}$ is methyl; and
$R^{3b}$ and $R^{1c}$ are H;
or a salt, hydrate, or isomer thereof.

In some embodiments, the invention provides a compound having the structure:

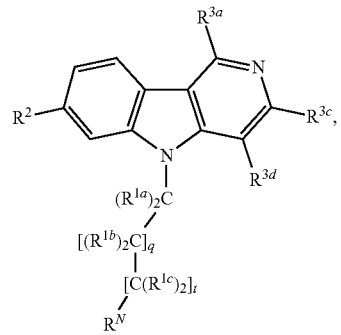

or a salt, hydrate, or isomer thereof; wherein:
$R^2$ is selected from the group consisting of H, $C_{1-6}$ alkoxy, —OH, and $C_{1-6}$ alkyl-OH;
$R^{3a}$ and $R^{1c}$ are independently selected from the group consisting of H, halo, $C_{1-6}$ alkoxy, —OH, and
$R^{3d}$ is selected from the group consisting of H, $C_{1-6}$ alkyl and $C_{1-6}$ haloalkyl.

In some embodiments, the invention provides a compound wherein:
$R^2$ is methoxy;
$R^{3d}$ is methyl; and
$R^{3a}$ and $R^{1c}$ are H;
or a salt, hydrate, or isomer thereof.

In some embodiments, the invention provides a compound having the structure:

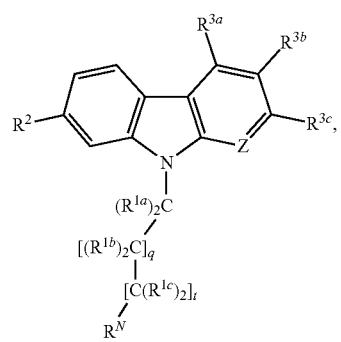

or a salt, hydrate, or isomer thereof; wherein:
Z is selected from C—H and N;
$R^2$ is selected from the group consisting of H and methoxy; and
$R^{3a}$, $R^{3b}$, and $R^{3c}$ are H;
or a salt, hydrate, or isomer thereof.

In some embodiments, the invention provides a compound wherein Z is N and $R^2$ is H, or a salt, hydrate, or isomer thereof.

In some embodiments, the invention provides a compound of structure:

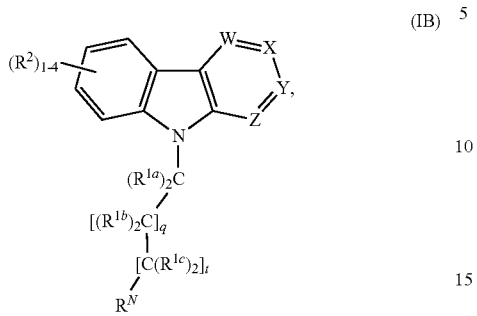

(IB)

or a salt, hydrate, or isomer thereof; wherein:
W is selected from $CR^{3a}$ and N, wherein N is optionally oxidized to the corresponding N-oxide;
X is selected from $CR^{3b}$ and N, wherein N is optionally oxidized to the corresponding N-oxide;
Y is selected from $CR^{3c}$ and N, wherein N is optionally oxidized to the corresponding N-oxide;
Z is selected from $CR^{3d}$ and N, wherein N is optionally oxidized to the corresponding N-oxide;
$R^N$ is selected from the group consisting of heterocyclyl, and heteroaryl, wherein heterocyclyl and heteroaryl comprise from about 5 to about 10 ring atoms, at least one of which is nitrogen, and wherein any N in $R^N$ is optionally oxidized to the corresponding N-oxide;
each $R^{1a}$, $R^{1b}$, and $R^{1c}$ is independently selected from H, methyl, and ethyl, wherein the total number of carbon atoms in the group —$C(R^{1a})_2$—$[C(R^{1b})_2]_q$—$[C(R^{1c})_2]_t$— does not exceed six; each $R^2$, $R^{3a}$, $R^{3b}$, $R^{1c}$ and $R^{3d}$ is independently selected from the group consisting of H, halogen, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$haloalkoxy, aryloxy, $C_{1-6}$ alkyl-OH, —$OR^4$, —$C_{0-6}$alkyl-$NR^4R^5$, —$SR^4$, —$C(O)R^4$, —$C_{0-6}$ alkyl-$C(O)OR^4$, —$C(O)NR^4R^5$, —$N(R^4)C(O)R^5$, —$N(R^4)C(O)OR^5$, —$N(R^4)C(O)NR^4R^5$, —$OP(O)(OR^4)_2$, —$S(O)_2OR^4$, —$S(O)_2NR^4R^5$, —CN, cycloalkyl, heterocycloalkyl, aryl and heteroaryl;
alternatively, two $R^2$ groups on adjacent atoms can be combined with the atoms to which they are attached to form a member selected from the group consisting of cycloalkyl, heterocycloalkyl, aryl and heteroaryl;
each $R^4$, $R^5$, $R^6$, and $R^7$ is independently selected from the group consisting of H, $C_{1-6}$ alkyl, and $C_{1-6}$ alkyl-OH;
the subscript q is an integer from 0 to 4;
the subscript t is an integer from 0 to 4; and
provided that no more than one of W, X, Y, and Z is N or the corresponding N-oxide.

In one group of embodiments, $R^N$ is a heterocyclyl group. In another group of embodiments, $R^N$ is a heteroaryl group. In an additional set of embodiments, $R^N$ is a piperidinyl, homopiperidinyl, piperazinyl, homopiperazinyl, morpholinyl, pyrrolidinyl or azetidinyl group. In further embodiments, $R^N$ is a triazolyl, tetrazolyl, imdidazolyl or pyridinyl group.

In some embodiments, the invention provides a compound having the structure:

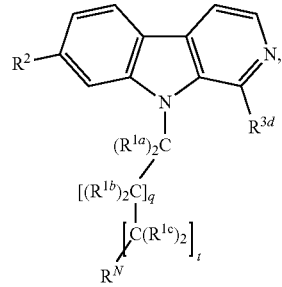

or a salt, hydrate, or isomer thereof; wherein:
$R^2$ is selected from the group consisting of —OH, $C_{1-6}$ alkoxy, and aryloxy; and
$R^{3d}$ is selected from the group consisting of $C_{1-6}$ alkyl, aryl, and heteroaryl.

In some embodiments, the invention provides a compound wherein:
$R^2$ is selected from —OH and methoxy; and
$R^{3d}$ is selected from the group consisting of 4-methoxyphenyl; 1,2,3-triazolyl; 1,2,4-oxadizaolyl; and 1,3,4-oxadiazolyl;
or a salt, hydrate, or isomer thereof.

In some embodiments, the invention provides a compound wherein:
$R^2$ is selected from the group consisting of phenoxy, (4-methyl)phenoxy, (4-methoxy)phenoxy, (4-chloro)phenoxy, and (3,4-dichloro)phenoxy; and
$R^{3d}$ is methyl;
or a salt, hydrate, or isomer thereof.

In some embodiments, the invention provides a compound of structure:

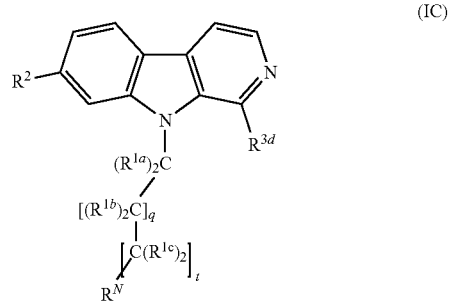

(IC)

wherein:
$R^2$ is selected from H, halogen, —OH and $C_{1-6}$alkoxy;
$R^{3d}$ is selected from H, halogen, $C_{1-6}$ alkyl, $C_{1-6}$ haloalkyl, $C_{1-6}$ alkoxy, $C_{1-6}$ haloalkoxy, and $C_{1-6}$ alkyl-OH;
$R^N$ is selected from the group consisting of heterocyclyl, and heteroaryl, wherein heterocyclyl and heteroaryl comprise from about 5 to about 10 ring atoms, at least one of which is nitrogen, and wherein any N in $R^N$ is optionally oxidized to the corresponding N-oxide;
each $R^{1a}$, $R^{1b}$, and $R^{1c}$ is independently selected from H, methyl, and ethyl, wherein the total number of carbon atoms in the group —$C(R^{1a})_2$—$[C(R^{1b})_2]_q$—$[C(R^{1c})_2]_t$— does not exceed six;
the subscript q is an integer from 0 to 4; and
the subscript t is an integer from 0 to 4;
or a salt, hydrate, or isomer thereof.

In one group of embodiments for compounds of formula (IC), $R^2$ is selected from fluoro, —OH, methoxy, ethoxy, isopropoxy, or isobutoxy. In one group of embodiments for compounds of formula (IC), $R^{3d}$ is selected from fluoro, chloro, methoxy, ethoxy, methyl, ethyl, or trifluoromethyl.

In some embodiments, the invention provides compounds of Formula ID:

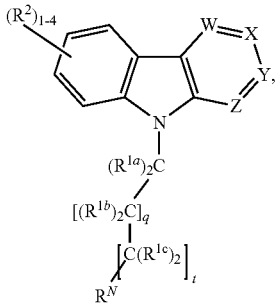

or a salt, hydrate, or isomer thereof; wherein:

W is selected from $CR^{3a}$ and N, wherein N is optionally oxidized to the corresponding N-oxide;

X is selected from $CR^{3b}$ and N, wherein N is optionally oxidized to the corresponding N-oxide;

Y is selected from $CR^{3c}$ and N, wherein N is optionally oxidized to the corresponding N-oxide;

Z is selected from $CR^{3d}$ and N, wherein N is optionally oxidized to the corresponding N-oxide;

$R^N$ is selected from the group consisting of $NR^6R^7$, heterocyclyl, and heteroaryl, wherein heterocyclyl and heteroaryl comprise from about 5 to about 10 ring atoms, at least one of which is nitrogen, and wherein any N in $R^N$ is optionally oxidized to the corresponding N-oxide;

each $R^{1a}$, $R^{1b}$, and $R^{1c}$ is independently selected from H, methyl, and ethyl, wherein the total number of carbon atoms in the group —$C(R^{1a})_2$—$[C(R^{1b})_2]_q$—$[C(R^{1c})_2]_t$— does not exceed six;

each $R^2$, $R^{3a}$, $R^{3b}$, $R^{3c}$ and $R^{3d}$ is independently selected from the group consisting of H, halogen, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, aryloxy, $C_{1-6}$ alkyl-OH, —$OR^4$, —$C_{0-6}$ alkyl-$NR^4R^5$, —$SR^4$, —$C(O)R^4$, —$C_{0-6}$ alkyl-$C(O)OR^4$, —$C(O)NR^4R^5$, —$N(R^4)C(O)R^5$, —$N(R^4)C(O)OR^5$, —$N(R^4)C(O)NR^4R^5$, —$OP(O)(OR^4)_2$, —$S(O)_2OR^4$, —$S(O)_2NR^4R^5$, —CN, cycloalkyl, heterocycloalkyl, aryl and heteroaryl;

alternatively, two $R^2$ groups on adjacent atoms can be combined with the atoms to which they are attached to form a member selected from the group consisting of cycloalkyl, heterocycloalkyl, aryl and heteroaryl;

each $R^4$, $R^5$, $R^6$, and $R^7$ is independently selected from the group consisting of H, $C_{1-6}$ alkyl, $C_{1-6}$ alkyl-OH, and $C_{1-6}$ alkyl-O—$C_{1-6}$ alkyl;

the subscript q is an integer from 0 to 4; and the subscript t is an integer from 0 to 4;

provided that no more than one of W, X, Y, and Z is N or the corresponding N-oxide.

In some embodiments, the invention provides compounds of formula ID wherein when
  a) the sum of q and t is 1, and
  b) both of $R^6$ and $R^7$, if present, are H or $C_{1-6}$ alkyl,
at least one of $R^{1a}$ and $R^{1b}$ is other than H;
and wherein
  when the sum of q and t is 2,
  a) $R^2$ is other than H, and
  b) at least one of $R^6$ and $R^7$, if present, is other than H or methyl.

In some embodiments, the invention provides compounds of formula ID wherein when
  a) the sum of q and t is 1, and
  b) both of $R^6$ and $R^7$, if present, are H or $C_{1-6}$ alkyl,
at least one of $R^{1a}$ and $R^{1b}$ is other than H;
and wherein when
  a) the sum of q and t is 1, and
  b) $R^N$ is heterocyclyl,
at least one $R^2$ is other than H;
and wherein when the sum of q and t is 2,
  a) at least one $R^2$ is other than H,
  b) $R^N$ is not phthalimido, and
  c) at least one of $R^6$ and $R^7$, if present, is other than H or methyl;
and wherein when:
  a) the sum of q and t is 3, and
  b) each of $R^{1a}$, $R^{1b}$ and $R^{1c}$ is H,
$R^N$ is not phthalimido and at least one of $R^6$ and $R^7$, if present, is other than H, methyl, and ethyl.

In certain embodiments, the invention provides compounds of formula ID as described above, provided that the compound is not:

1-amino-3-(3,6-dibromo-9H-carbazol-9-yl)propan-2-ol;
1-(3,6-dibromo-9H-pyrido[3,4-b]indol-9-yl)-3-((3-methoxyphenyl)amino)propan-2-ol;
9-(2-(piperidin-1-yl)ethyl)-9H-pyrido[3,4-b]indole-3-carboxamide;
methyl 9-(4-(dimethylamino)butyl)-9H-pyrido[3,4-b]indole-3-carboxylate;
N,N-dimethyl-4-(9H-pyrido[3,4-b]indol-9-yl)butan-1-amine;
N-ethyl-N-methyl-4-(9H-pyrido[3,4-b]indol-9-yl)butan-1-amine;
2-[4-[7-hydroxy-1-(trifluoromethyl)-9H-pyrido[3,4-b]indol-9-yl]butyl]-1H-Isoindole-1,3(2H)-dione;
2-[4-[7-methoxy-1-(trifluoromethyl)-9H-pyrido[3,4-b]indol-9-yl]butyl]-1H-Isoindole-1,3(2H)-dione;
2-[4-(7-hydroxy-1-methyl-9H-pyrido[3,4-b]indol-9-yl)butyl]-1H-Isoindole-1,3(2H)-dione;
2-[3-(7-methoxy-1-methyl-9H-pyrido[3,4-b]indol-9-yl)propyl]-1H-Isoindole-1,3(2H)-dione;
9-(4-aminobutyl)-1-(trifluoromethyl)-9H-pyrido[3,4-b]indol-7-ol;
7-methoxy-N,N,1-trimethyl-9H-pyrido[3,4-b]indole-9-butanamine;
7-methoxy-N,1-dimethyl-9H-pyrido[3,4-b]indole-9-butanamine;
7-methoxy-1-(trifluoromethyl)-9H-pyrido[3,4-b]indole-9-butanamine;
9-(4-aminobutyl)-1-methyl-9H-pyrido[3,4-b]indol-7-ol;
7-methoxy-9H-pyrido[3,4-b]indole-9-butanamine;
7-methoxy-1-methyl-9H-pyrido[3,4-b]indole-9-butanamine;
7-methoxy-1-methyl-9H-pyrido[3,4-b]indole-9-propanamine;
N,N-dimethyl-N-[3-(7-methoxy-1-methyl-9H-b-carbolin-9-yl)-propyl]amine;
N,N,1,3-tetramethyl-9H-pyrido[3,4-b]indole-9-ethanamine;
N,N-diethyl-7-methoxy-1-methyl-9H-pyrido[3,4-b]indole-9-ethanamine;
7-methoxy-N,N,1-trimethyl-9H-pyrido[3,4-b]indole-9-ethanamine;
4-(7-methoxy-1-methyl-9H-pyrido[3,4-b]indol-9-yl)-N,N-dimethylbutan-1-amine;

4-(7-methoxy-1-methyl-9H-pyrido[3,4-b]indol-9-yl)-N-methylbutan-1-amine;

4-(7-methoxy-1-methyl-9H-pyrido[3,4-b]indol-9-yl)butan-1-amine;

1-(9H-carbazol-9-yl)-N,N-dimethylpropan-2-amine; or 2-(7-methoxy-1-methyl-9H-pyrido[3,4-b]indol-9-yl)-N,N-dimethyl ethanamine.

In some embodiments, the invention provides a compound of structure

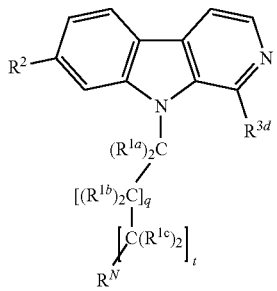

wherein:

R² is selected from —OH and methoxy;

R³ᵈ is selected from methyl or trifluoromethyl; and

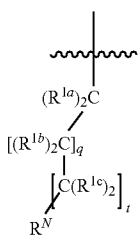

is selected from the following:

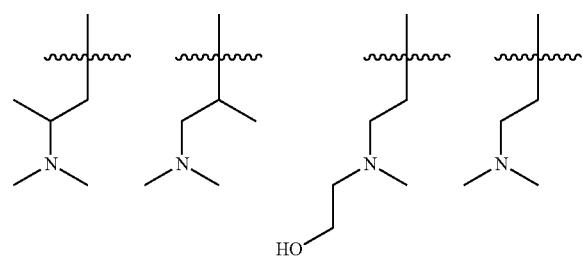

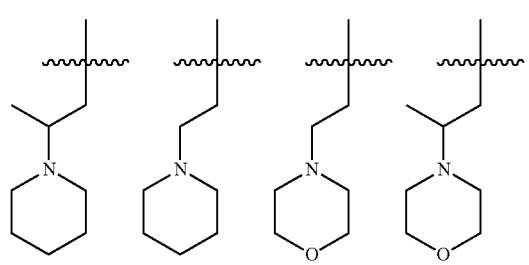

-continued

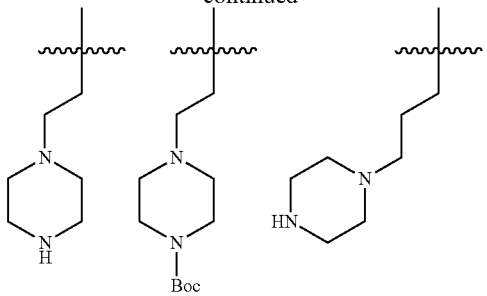

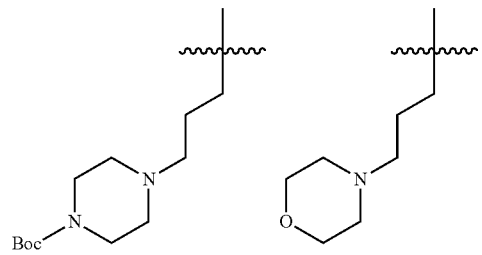

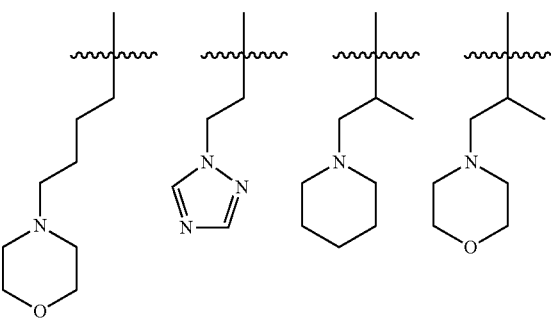

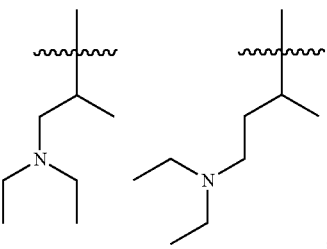

;

or a salt, hydrate, or isomer thereof.

In some embodiments, the invention provides a compound of structure

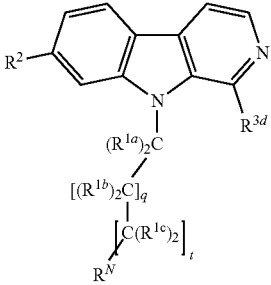

wherein:

$R^2$ is selected from —OH and methoxy;

$R^{3d}$ is selected from methyl or trifluoromethyl; and

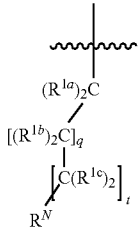

is selected from the following:

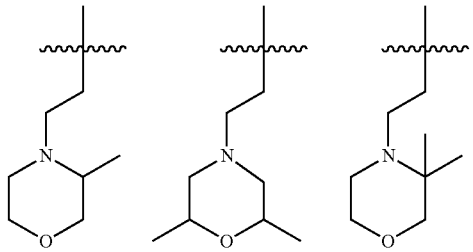

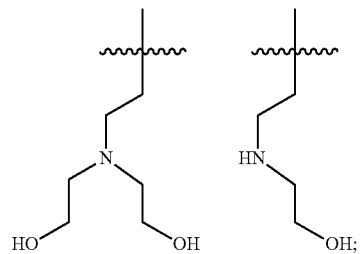

or a salt, hydrate, or isomer thereof.

In some embodiments, the invention provides a compound of structure

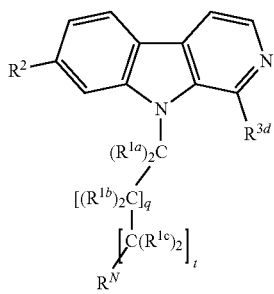

wherein:

$R^2$ is selected from —OH and methoxy;

$R^{3d}$ is selected from methyl or trifluoromethyl; and

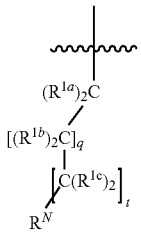

is selected from the following:

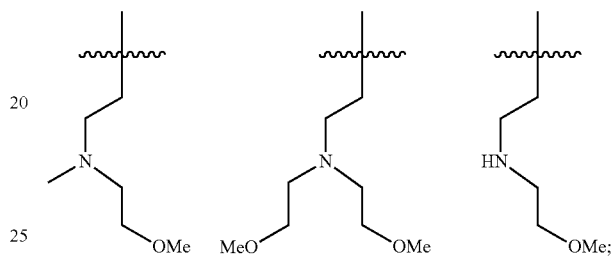

or a salt, hydrate, or isomer thereof.

For any of the embodiments described above, in one instance, the nitrogen at the Z position is oxidized to an N-oxide.

In some embodiments, the invention provides a compound wherein the subscript q and the subscript t are 0.

In some embodiments, the invention provides a compound wherein the subscript q is 0 and the subscript t is 1.

In some embodiments, the invention provides a compound wherein the subscript q is 1 and the subscript t is 0.

In some embodiments, the invention provides a compound wherein the subscript q and the subscript t are 1.

In some embodiments of the compounds provided herein, the group —$C(R^{1a})_2$—$[C(R^{1b})_2]_q$—$[C(R^{1c})_2]_t$— is a straight chain alkyl group. In other embodiments, the group —$C(R^{1a})_2$—$[C(R^{1b})_2]_q$—$[C(R^{1c})_2]_t$— is a branched chain alkyl group. In some embodiments, the group $R^N$ is a dialkylamino group where the alkyl is a straight chain alkyl or a branched alkyl group. In additional embodiments, the alkyl position in the dialkylamino portion is optionally substituted with a hydroxyl group. In further embodiments, the group $R^N$ is a heterocyclyl or heteroaryl group. Where $R^N$ is a heterocyclyl or heteroaryl group, $R^N$ is attached to the rest of the molecule either via a carbon atom, or via a nitrogen atom. In further embodiments, where $R^N$ is a heterocyclyl or heteroaryl group, $R^N$ is attached to the rest of the molecule either via a carbon atom, or via a nitrogen atom and further, a nitrogen atom in $R^N$ is optionally oxidized to the corresponding N-oxide.

In some embodiments, the invention provides a compound wherein the group —$C(R^{1a})_2$—$[C(R^{1b})_2]_q$—$[C(R^{1c})_2]_t$— is selected from the group consisting of:

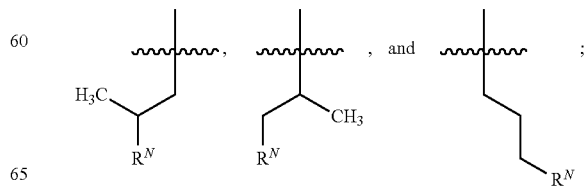

or a salt, hydrate, or isomer thereof.

In some embodiments, the invention provides a compound wherein the group —C(R$^{1a}$)$_2$—[C(R$^{1b}$)$_2$]$_q$—[C(R$^{1c}$)$_2$]$_t$— is selected from the group consisting of:

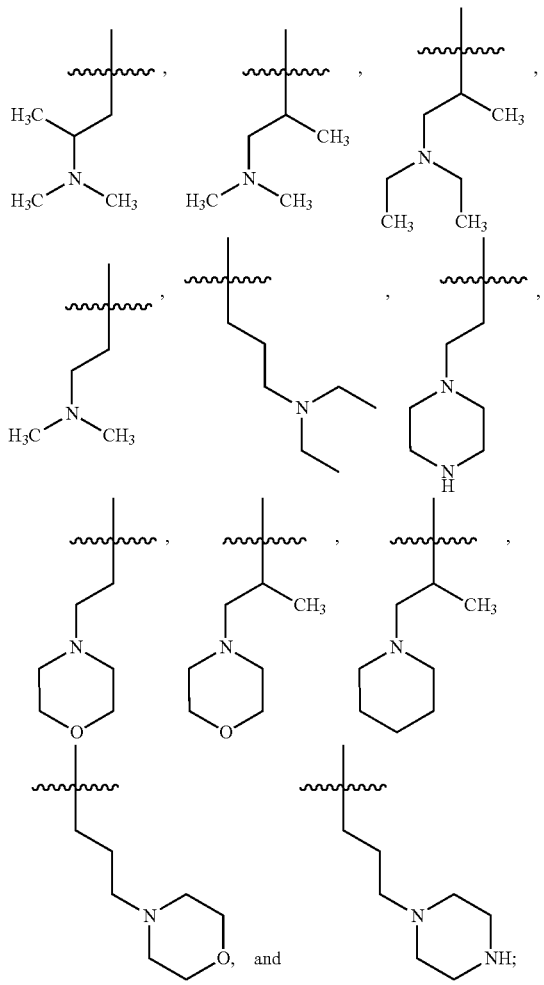

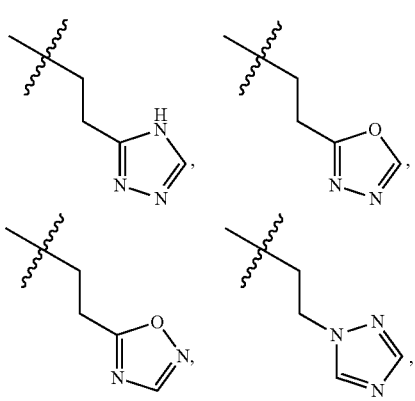

or a salt, hydrate, or isomer thereof.

In some embodiments, the invention provides a compound wherein the group —C(R$^{1a}$)$_2$—[C(R$^{1b}$)$_2$]$_q$—[C(R$^{1c}$)$_2$]$_t$— is selected from the group consisting of:

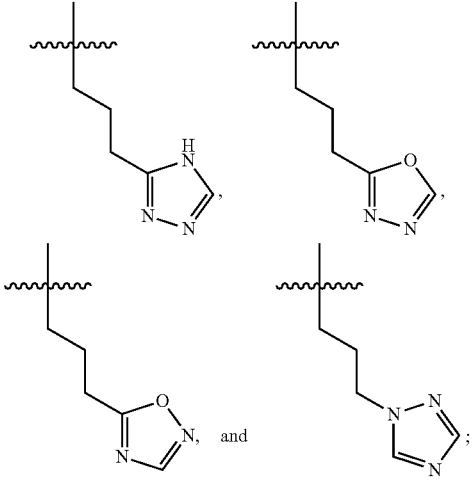

or a salt, hydrate, or isomer thereof.

In some embodiments, the invention provides a compound selected from the group consisting of:

9-(2-(dimethylamino)propyl)-9H-pyrido[3,4-b]indol-7-ol;
9-(2-(dimethylamino)propyl)-1-methyl-9H-pyrido[3,4-b]indol-7-ol;
N,N-dimethyl-1-(9H-pyrido[3,4-b]indol-9-yl)propan-2-amine;
1-(7-methoxy-9H-pyrido[3,4-b]indol-9-yl)-N,N-dimethylpropan-2-amine;
1-(2-methoxy-9H-carbazol-9-yl)-N,N-dimethylpropan-2-amine;
4-(3-(7-methoxy-1-methyl-9H-pyrido[3,4-b]indol-9-yl)propyl)morpholine;
N,N-diethyl-3-(7-methoxy-1-methyl-9H-pyrido[3,4-b]indol-9-yl)propan-1-amine;
7-methoxy-1-methyl-9-(3-(piperazin-1-yl)propyl)-9H-pyrido[3,4-b]indole;
2-(7-methoxy-1-methyl-9H-pyrido[3,4-b]indol-9-yl)-N,N-dimethylpropan-1-amine;
N,N-diethyl-2-(7-methoxy-1-methyl-9H-pyrido[3,4-b]indol-9-yl)propan-1-amine;
7-methoxy-1-methyl-9-(2-(piperazin-1-yl)ethyl)-9H-pyrido[3,4-b]indole;
4-(2-(7-methoxy-1-methyl-9H-pyrido[3,4-b]indol-9-yl)ethyl)morpholine;
4-(2-(7-methoxy-1-methyl-9H-pyrido[3,4-b]indol-9-yl)propyl)morpholine;
7-methoxy-1-methyl-9-(1-(piperidin-1-yl)propan-2-yl)-9H-pyrido[3,4-b]indole;
9-(2-(4H-1,2,4-triazol-3-yl)ethyl)-7-methoxy-1-methyl-9H-pyrido[3,4-b]indole;
2-(2-(7-methoxy-1-methyl-9H-pyrido[3,4-b]indol-9-yl)ethyl)-1,3,4-oxadiazole;
5-(2-(7-methoxy-1-methyl-9H-pyrido[3,4-b]indol-9-yl)ethyl)-1,2,4-oxadiazole;
9-(2-(1H-1,2,4-triazol-1-yl)ethyl)-7-methoxy-1-methyl-9H-pyrido[3,4-b]indole;
9-(3-(4H-1,2,4-triazol-3-yl)propyl)-7-methoxy-1-methyl-9H-pyrido[3,4-b]indole;
2-(3-(7-methoxy-1-methyl-9H-pyrido[3,4-b]indol-9-yl)propyl)-1,3,4-oxadiazole;
5-(3-(7-methoxy-1-methyl-9H-pyrido[3,4-b]indol-9-yl)propyl)-1,2,4-oxadiazole; and
9-(3-(1H-1,2,4-triazol-1-yl)propyl)-7-methoxy-1-methyl-9H-pyrido[3,4-b]indole;

or salts, hydrate, or isomers thereof.

In some embodiments, the invention provides a compound of Formula I or Formula II selected from the group consisting of:
1-(7-methoxy-1-methyl-9H-pyrido[3,4-b]indol-9-yl)-N,N-dimethylpropan-2-aminium formate;
N,N-dimethyl-1-(9H-pyrido[2,3-b]indol-9-yl)propan-2-amine;
1-(9H-carbazol-9-yl)-N,N-dimethylpropan-2-amine; and
9-(2-(dimethylamino)propyl)-1-methyl-9H-pyrido[3,4-b]indol-7-ol.

In some embodiments, the invention provides a compound selected from the group consisting of:
7-methoxy-1-methyl-9H-pyrido[3,4-b]indol-3-ol;
1-methyl-9H-pyrido[3,4-b]indole-3,7-diol;
7-methoxy-1-(trifluoromethyl)-9H-pyrido[3,4-b]indole;
3-fluoro-7-methoxy-1-methyl-9H-pyrido[3,4-b]indole; and
3,7-dimethoxy-1-methyl-9H-pyrido[3,4-b]indole.

In some embodiments, the invention provides a compound of Formula III selected from the group consisting of:
7-methoxy-4-methyl-5H-pyrido[3,2-b]indole; and
7-methoxy-4-methyl-5H-pyrido[4,3-b]indole.

In additional embodiments, the invention provides compounds having any of the following structures:

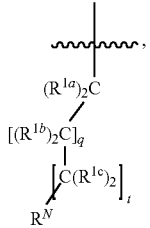

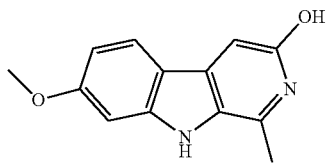

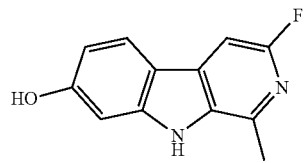

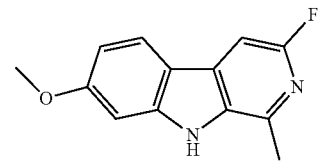

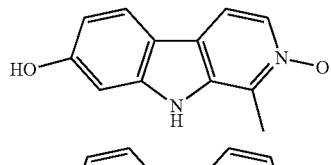

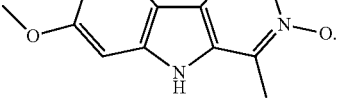

In further embodiments, the compounds described above are further modified to attach the group

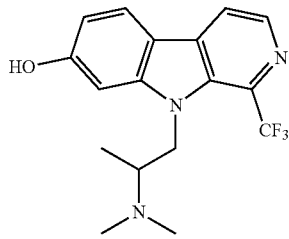

which is described above, using the procedures described herein.

Accordingly, further provided herein are the following compounds:

9-(2-(dimethylamino)propyl)-1-(trifluoromethyl)-9H-pyrido[3,4-b]indol-7-ol;

35

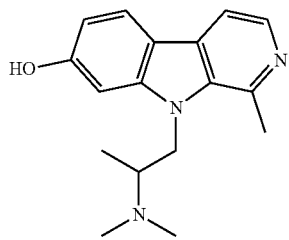 [SMILES: Cc1nccc2c3ccc(O)cc3n(CC(C)N(C)C)c12]

9-(2-(dimethylamino)propyl)-1-methyl-9H-pyrido[3,4-b]indol-7-ol;

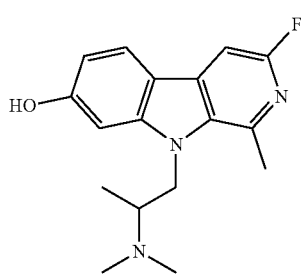 [SMILES: Cc1nc(F)cc2c3ccc(O)cc3n(CC(C)N(C)C)c12]

9-(2-(dimethylamino)propyl)-3-fluoro-1-methyl-9H-pyrido[3,4-b]indol-7-ol;

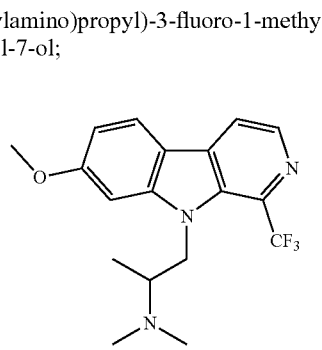

1-(7-methoxy-1-(trifluoromethyl)-9H-pyrido[3,4-b]indol-9-yl)-N,N-dimethylpropan-2-amine;

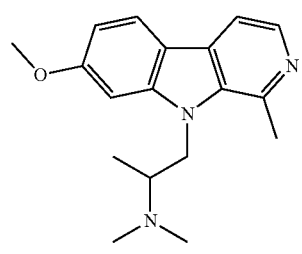 [SMILES: COc1ccc2c3ccnc(C)c3n(CC(C)N(C)C)c2c1]

36

1-(7-methoxy-1-methyl-9H-pyrido[3,4-b]indol-9-yl)-N,N-dimethylpropan-2-amine;

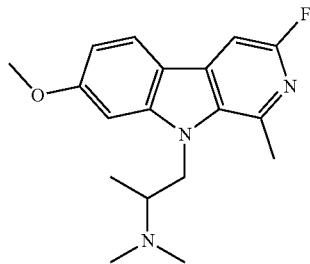 [SMILES: COc1ccc2c3cc(F)nc(C)c3n(CC(C)N(C)C)c2c1]

1-(3-fluoro-7-methoxy-1-methyl-9H-pyrido[3,4-b]indol-9-yl)-N,N-dimethylpropan-2-amine;

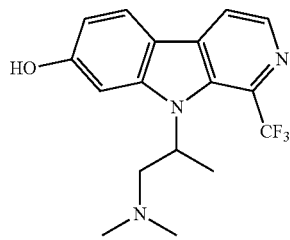

9-(1-(dimethylamino)propan-2-yl)-1-(trifluoromethyl)-9H-pyrido[3,4-b]indol-7-ol;

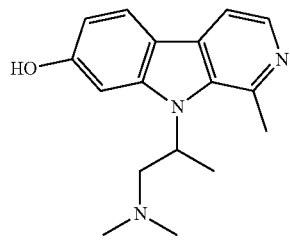 [SMILES: Cc1nccc2c3ccc(O)cc3n(C(C)CN(C)C)c12]

9-(1-(dimethylamino)propan-2-yl)-1-methyl-9H-pyrido[3,4-b]indol-7-ol;

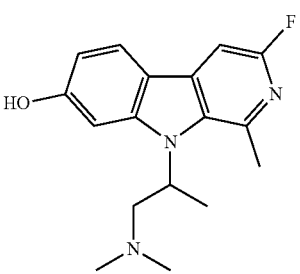 [SMILES: Cc1nc(F)cc2c3ccc(O)cc3n(C(C)CN(C)C)c12]

9-(1-(dimethylamino)propan-2-yl)-3-fluoro-1-methyl-9H-pyrido[3,4-b]indol-7-ol;

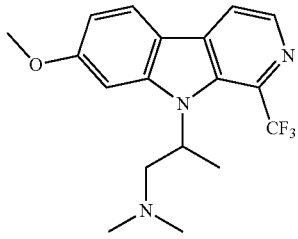 [SMILES: COc1ccc2c3ccnc(C)c3n(C(C)CN(C)C)c2c1]

2-(7-methoxy-1-(trifluoromethyl)-9H-pyrido[3,4-b]indol-9-yl)-N,N-dimethylpropan-1-amine;

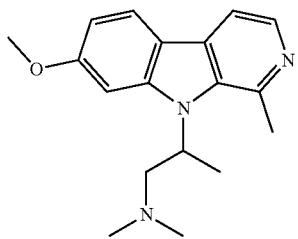

2-(7-methoxy-1-methyl-9H-pyrido[3,4-b]indol-9-yl)-N,N-dimethylpropan-1-amine;

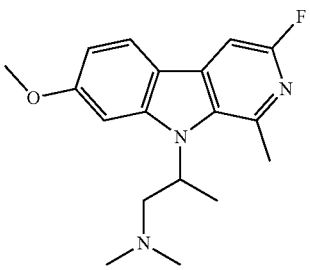 [SMILES: COc1ccc2c3cc(F)nc(C)c3n(C(C)CN(C)C)c2c1]

2-(3-fluoro-7-methoxy-1-methyl-9H-pyrido[3,4-b]indol-9-yl)-N,N-dimethylpropan-1-amine;

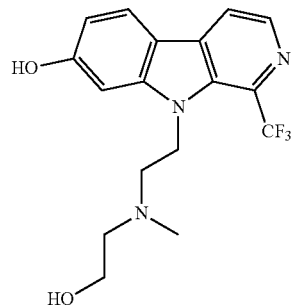

9-(2-((2-hydroxyethyl)(methyl)amino)ethyl)-1-(trifluoromethyl)-9H-pyrido[3,4-b]indol-7-ol;

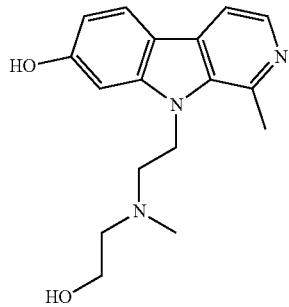 [SMILES: Cc1nccc2c3ccc(O)cc3n(CCN(C)CCO)c12]

9-(2-((2-hydroxyethyl)(methyl)amino)ethyl)-1-methyl-9H-pyrido[3,4-b]indol-7-ol;

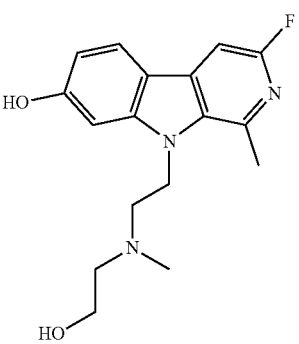 [SMILES: Cc1nc(F)cc2c3ccc(O)cc3n(CCN(C)CCO)c12]

3-fluoro-9-(2-((2-hydroxyethyl)(methyl)amino)ethyl)-1-methyl-9H-pyrido[3,4-b]indol-7-ol;

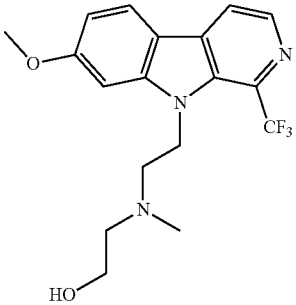 [SMILES: COc1ccc2c3ccnc(C(F)(F)F)c3n(CCN(C)CCO)c2c1]

2-((2-(7-methoxy-1-(trifluoromethyl)-9H-pyrido[3,4-b]indol-9-yl)ethyl)(methyl)amino)ethanol;

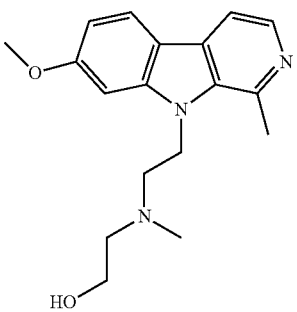 [SMILES: COc1ccc2c3ccnc(C)c3n(CCN(C)CCO)c2c1]

2-((2-(7-methoxy-1-methyl-9H-pyrido[3,4-b]indol-9-yl)ethyl)(methyl)amino)ethanol;

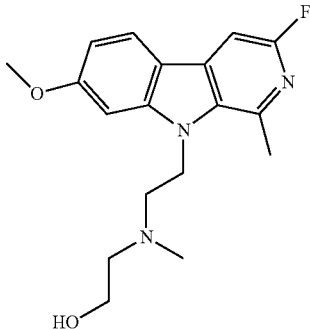 [SMILES: COc1ccc2c3cc(F)nc(C)c3n(CCN(C)CCO)c2c1]

2-((2-(3-fluoro-7-methoxy-1-methyl-9H-pyrido[3,4-b]indol-9-yl)ethyl)(methyl)amino)ethanol;

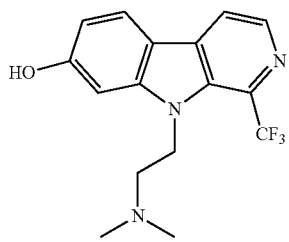 [SMILES: CN(C)CCn1c2cc(O)ccc2c2ccnc(C(F)(F)F)c21]

9-(2-(dimethylamino)ethyl)-1-(trifluoromethyl)-9H-pyrido[3,4-b]indol-7-ol;

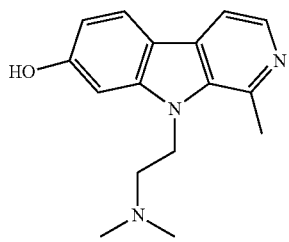 [SMILES: Cc1nccc2c3ccc(O)cc3n(CCN(C)C)c12]

9-(2-(dimethylamino)ethyl)-1-methyl-9H-pyrido[3,4-b]indol-7-ol;

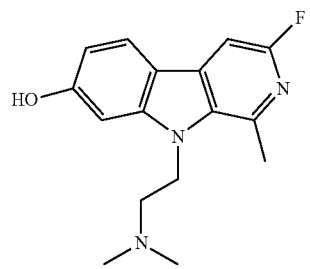 [SMILES: Cc1nc(F)cc2c3ccc(O)cc3n(CCN(C)C)c12]

9-(2-(dimethylamino)ethyl)-3-fluoro-1-methyl-9H-pyrido[3,4-b]indol-7-ol;

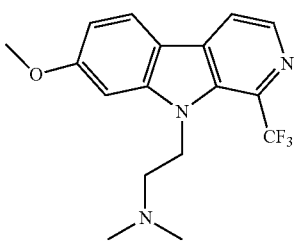 [SMILES: COc1ccc2c3ccnc(C(F)(F)F)c3n(CCN(C)C)c2c1]

2-(7-methoxy-1-(trifluoromethyl)-9H-pyrido[3,4-b]indol-9-yl)-N,N-dimethylethanamine;

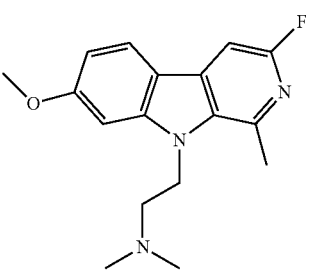 [SMILES: COc1ccc2c3cc(F)nc(C)c3n(CCN(C)C)c2c1]

2-(7-methoxy-1-methyl-9H-pyrido[3,4-b]indol-9-yl)-N,N-dimethylethanamine;

2-(3-fluoro-7-methoxy-1-methyl-9H-pyrido[3,4-b]indol-9-yl)-N,N-dimethylethanamine;

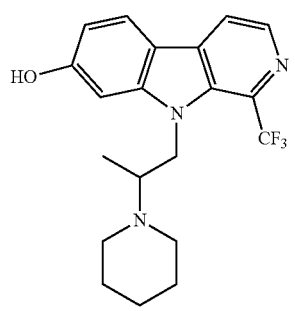 [SMILES: CC(Cn1c2cc(O)ccc2c2ccnc(C(F)(F)F)c21)N1CCCCC1]

9-(2-(piperidin-1-yl)propyl)-1-(trifluoromethyl)-9H-pyrido[3,4-b]indol-7-ol;

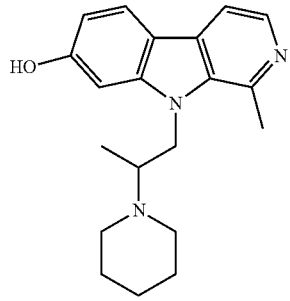 [SMILES: Cc1nccc2c3ccc(O)cc3n(CC(C)N3CCCCC3)c12]

1-methyl-9-(2-(piperidin-1-yl)propyl)-9H-pyrido[3,4-b]indol-7-ol;

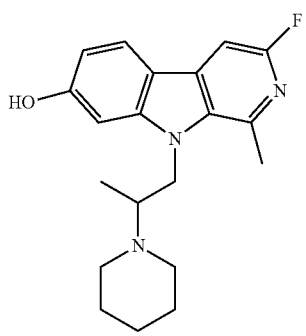 [SMILES: Cc1nc(F)cc2c3ccc(O)cc3n(CC(C)N3CCCCC3)c12]

3-fluoro-1-methyl-9-(2-(piperidin-1-yl)propyl)-9H-pyrido[3,4-b]indol-7-ol;

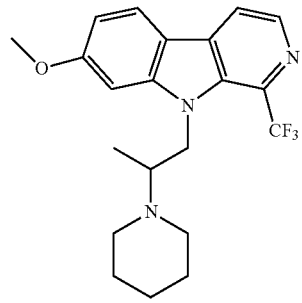 [SMILES: COc1ccc2c3ccnc(C(F)(F)F)c3n(CC(C)N3CCCCC3)c2c1]

7-methoxy-9-(2-(piperidin-1-yl)propyl)-1-(trifluoromethyl)-9H-pyrido[3,4-b]indole;

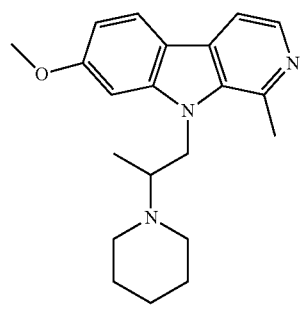 [SMILES: COc1ccc2c3ccnc(C)c3n(CC(C)N3CCCCC3)c2c1]

7-methoxy-1-methyl-9-(2-(piperidin-1-yl)propyl)-9H-pyrido[3,4-b]indole;

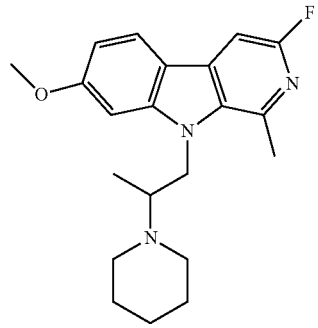 [SMILES: COc1ccc2c3cc(F)nc(C)c3n(CC(C)N3CCCCC3)c2c1]

3-fluoro-7-methoxy-1-methyl-9-(2-(piperidin-1-yl)propyl)-9H-pyrido[3,4-b]indole;

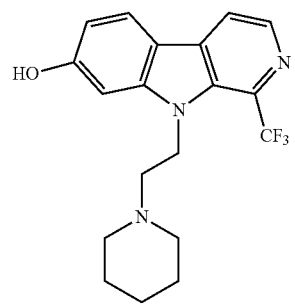 [SMILES: Oc1ccc2c3ccnc(C(F)(F)F)c3n(CCN3CCCCC3)c2c1]

9-(2-(piperidin-1-yl)ethyl)-1-(trifluoromethyl)-9H-pyrido[3,4-b]indol-7-ol;

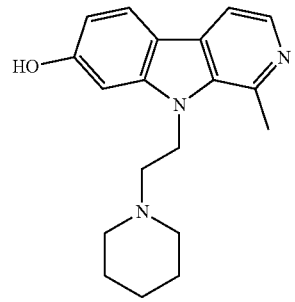 [SMILES: Cc1nccc2c3ccc(O)cc3n(CCN3CCCCC3)c12]

1-methyl-9-(2-(piperidin-1-yl)ethyl)-9H-pyrido[3,4-b]indol-7-ol;

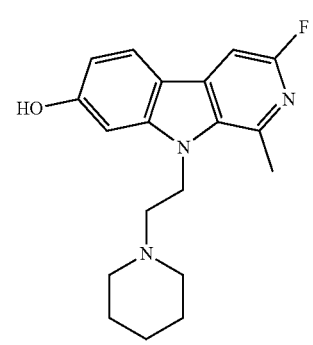 [SMILES: Cc1nc(F)cc2c3ccc(O)cc3n(CCN3CCCCC3)c12]

3-fluoro-1-methyl-9-(2-(piperidin-1-yl)ethyl)-9H-pyrido[3,4-b]indol-7-ol;

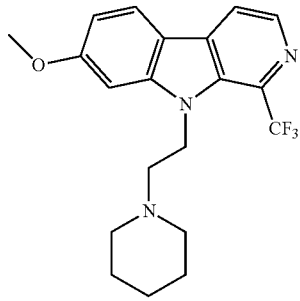 [SMILES: COc1ccc2c3ccnc(C(F)(F)F)c3n(CCN3CCCCC3)c2c1]

7-methoxy-9-(2-(piperidin-1-yl)ethyl)-1-(trifluoromethyl)-9H-pyrido[3,4-b]indole;

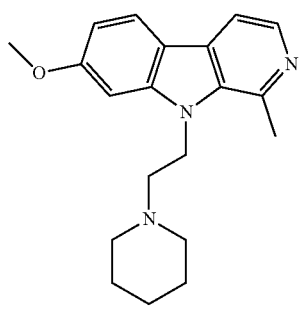 [SMILES: COc1ccc2c3ccnc(C)c3n(CCN3CCCCC3)c2c1]

7-methoxy-1-methyl-9-(2-(piperidin-1-yl)ethyl)-9H-pyrido[3,4-b]indole;

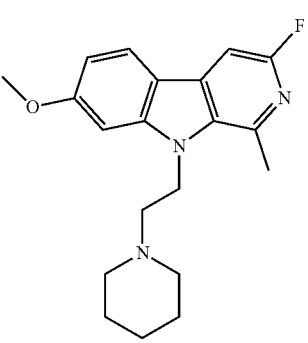 [SMILES: COc1ccc2c3cc(F)nc(C)c3n(CCN3CCCCC3)c2c1]

3-fluoro-7-methoxy-1-methyl-9-(2-(piperidin-1-yl)ethyl)-9H-pyrido[3,4-b]indole;

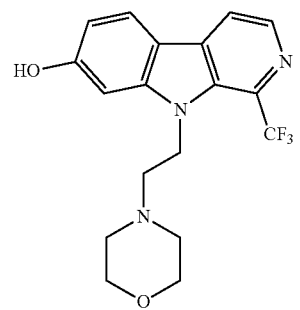

9-(2-morpholinoethyl)-1-(trifluoromethyl)-9H-pyrido[3,4-b]indol-7-ol;

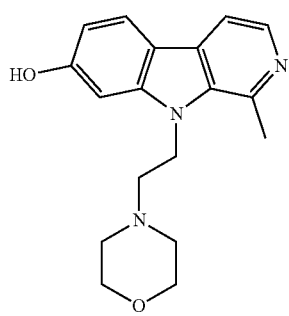 [SMILES: Cc1nccc2c3ccc(O)cc3n(CCN3CCOCC3)c12]

1-methyl-9-(2-morpholinoethyl)-9H-pyrido[3,4-b]indol-7-ol;

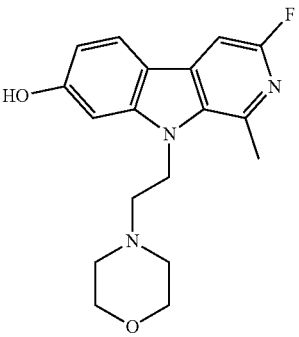 [SMILES: Cc1nc(F)cc2c3ccc(O)cc3n(CCN3CCOCC3)c12]

3-fluoro-1-methyl-9-(2-morpholinoethyl)-9H-pyrido[3,4-b]indol-7-ol;

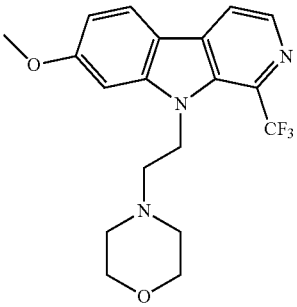 [SMILES: COc1ccc2c3ccnc(C(F)(F)F)c3n(CCN3CCOCC3)c2c1]

4-(2-(7-methoxy-1-(trifluoromethyl)-9H-pyrido[3,4-b]indol-9-yl)ethyl)morpholine;

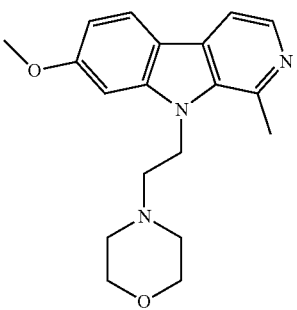 [SMILES: COc1ccc2c3ccnc(C)c3n(CCN3CCOCC3)c2c1]

4-(2-(7-methoxy-1-methyl-9H-pyrido[3,4-b]indol-9-yl)ethyl)morpholine;

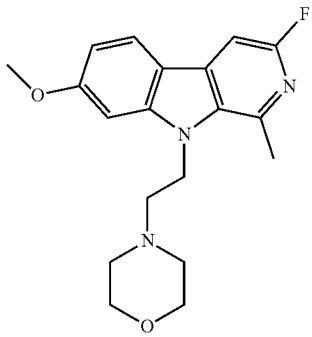 [SMILES: COc1ccc2c3cc(F)nc(C)c3n(CCN3CCOCC3)c2c1]

4-(2-(3-fluoro-7-methoxy-1-methyl-9H-pyrido[3,4-b]indol-9-yl)ethyl)morpholine;

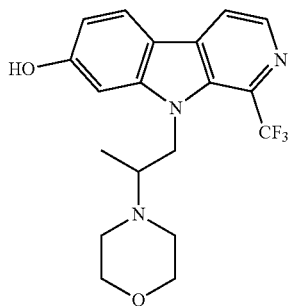

9-(2-morpholinopropyl)-1-(trifluoromethyl)-9H-pyrido[3,4-b]indol-7-ol;

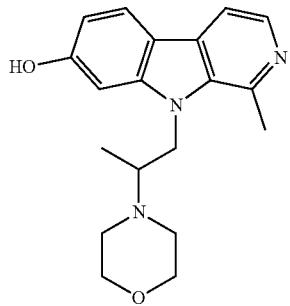 [SMILES: Cc1nccc2c3ccc(O)cc3n(CC(C)N3CCOCC3)c12]

1-methyl-9-(2-morpholinopropyl)-9H-pyrido[3,4-b]indol-7-ol;

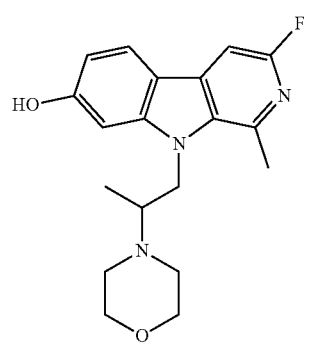 [SMILES: Cc1nc(F)cc2c3ccc(O)cc3n(CC(C)N3CCOCC3)c12]

3-fluoro-1-methyl-9-(2-morpholinopropyl)-9H-pyrido[3,4-b]indol-7-ol;

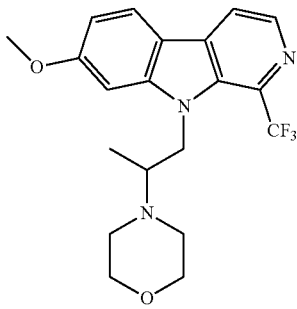 [SMILES: COc1ccc2c3ccnc(C(F)(F)F)c3n(CC(C)N3CCOCC3)c2c1]

4-(1-(7-methoxy-1-(trifluoromethyl)-9H-pyrido[3,4-b]indol-9-yl)propan-2-yl)morpholine;

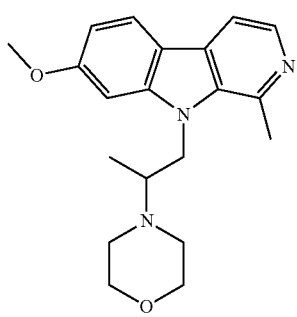 [SMILES: COc1ccc2c3ccnc(C)c3n(CC(C)N3CCOCC3)c2c1]

4-(1-(7-methoxy-1-methyl-9H-pyrido[3,4-b]indol-9-yl)propan-2-yl)morpholine;

4-(1-(3-fluoro-7-methoxy-1-methyl-9H-pyrido[3,4-b]indol-9-yl)propan-2-yl)morpholine;

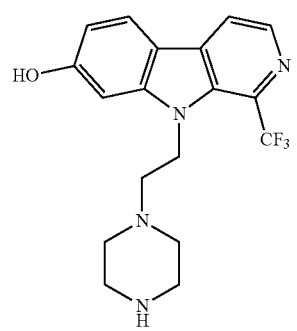 [SMILES: Oc1ccc2c3ccnc(C(F)(F)F)c3n(CCN3CCNCC3)c2c1]

9-(2-(piperazin-1-yl)ethyl)-1-(trifluoromethyl)-9H-pyrido[3,4-b]indol-7-ol;

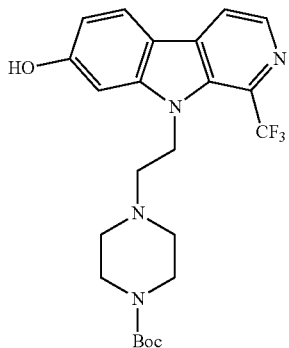 [SMILES: CC(C)(C)OC(=O)N1CCN(CCn2c3cc(O)ccc3c3ccnc(C(F)(F)F)c32)CC1]

tert-butyl 4-(2-(7-hydroxy-1-(trifluoromethyl)-9H-pyrido[3,4-b]indol-9-yl)ethyl)piperazine-1-carboxylate;

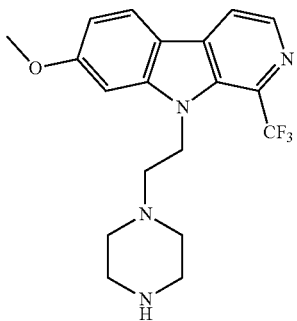

7-methoxy-9-(2-(piperazin-1-yl)ethyl)-1-(trifluoromethyl)-9H-pyrido[3,4-b]indole;

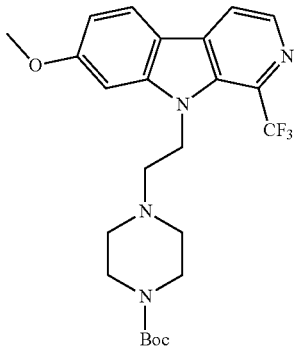 [SMILES: COc1ccc2c3ccnc(C(F)(F)F)c3n(CCN3CCN(C(=O)OC(C)(C)C)CC3)c2c1]

tert-butyl 4-(2-(7-methoxy-1-(trifluoromethyl)-9H-pyrido[3,4-b]indol-9-yl)ethyl)piperazine-1-carboxylate;

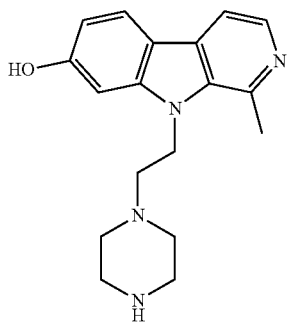 [SMILES: Cc1nccc2c3ccc(O)cc3n(CCN3CCNCC3)c12]

1-methyl-9-(2-(piperazin-1-yl)ethyl)-9H-pyrido[3,4-b]indol-7-ol;

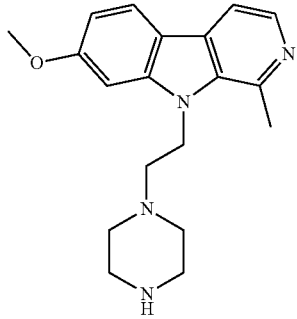 [SMILES: COc1ccc2c3ccnc(C)c3n(CCN3CCNCC3)c2c1]

7-methoxy-1-methyl-9-(2-(piperazin-1-yl)ethyl)-9H-pyrido[3,4-b]indole;

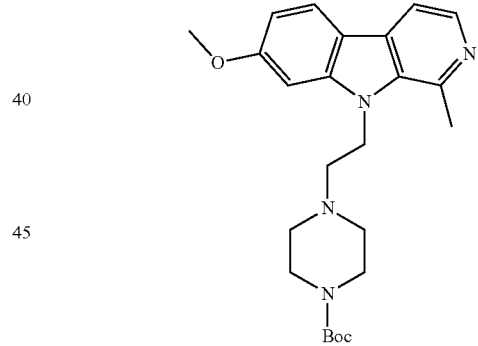

tert-butyl 4-(2-(7-hydroxy-1-methyl-9H-pyrido[3,4-b]indol-9-yl)ethyl)piperazine-1-carboxylate;

tert-butyl 4-(2-(7-methoxy-1-methyl-9H-pyrido[3,4-b]indol-9-yl)ethyl)piperazine-1-carboxylate;

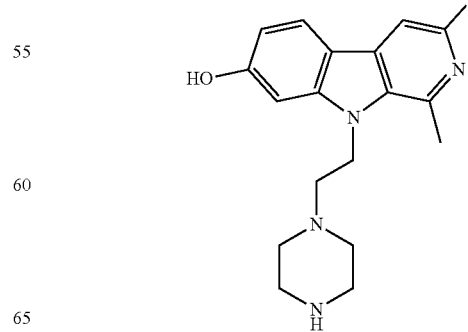

3-fluoro-1-methyl-9-(2-(piperazin-1-yl)ethyl)-9H-pyrido[3,4-b]indol-7-ol;

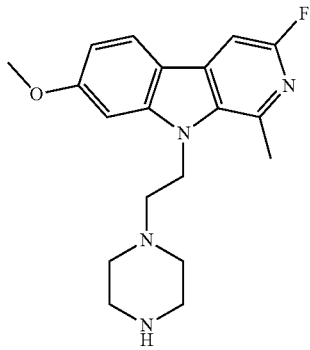 [SMILES: COc1ccc2c3cc(F)nc(C)c3n(CCN3CCNCC3)c2c1]

3-fluoro-7-methoxy-1-methyl-9-(2-(piperazin-1-yl)ethyl)-9H-pyrido[3,4-b]indole;

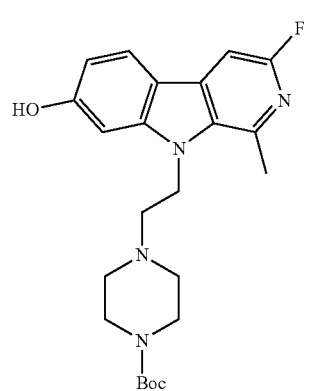 [SMILES: Cc1nc(F)cc2c3ccc(O)cc3n(CCN3CCN(C(=O)OC(C)(C)C)CC3)c12]

tert-butyl 4-(2-(3-fluoro-7-hydroxy-1-methyl-9H-pyrido[3,4-b]indol-9-yl)ethyl)piperazine-1-carboxylate;

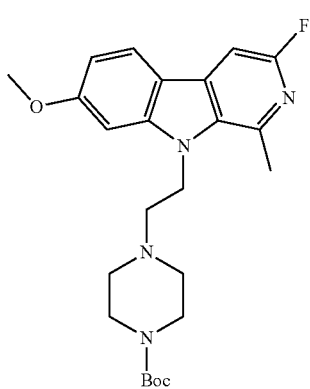 [SMILES: COc1ccc2c3cc(F)nc(C)c3n(CCN3CCN(C(=O)OC(C)(C)C)CC3)c2c1]

tert-butyl 4-(2-(3-fluoro-7-methoxy-1-methyl-9H-pyrido[3,4-b]indol-9-yl)ethyl)piperazine-1-carboxylate;

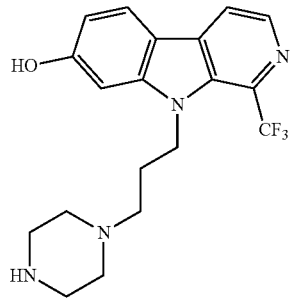 [SMILES: Oc1ccc2c3ccnc(C(F)(F)F)c3n(CCCN3CCNCC3)c2c1]

9-(3-(piperazin-1-yl)propyl)-1-(trifluoromethyl)-9H-pyrido[3,4-b]indol-7-ol;

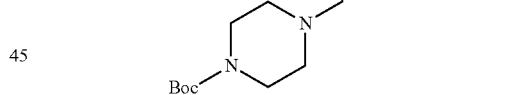

7-methoxy-9-(3-(piperazin-1-yl)propyl)-1-(trifluoromethyl)-9H-pyrido[3,4-b]indole;

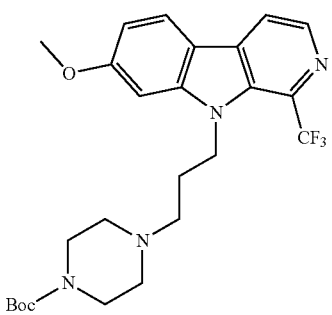 [SMILES: COc1ccc2c3ccnc(C(F)(F)F)c3n(CCCN3CCN(C(=O)OC(C)(C)C)CC3)c2c1]

tert-butyl 4-(3-(7-hydroxy-1-(trifluoromethyl)-9H-pyrido[3,4-b]indol-9-yl)propyl)piperazine-1-carboxylate;

tert-butyl 4-(3-(7-methoxy-1-(trifluoromethyl)-9H-pyrido[3,4-b]indol-9-yl)propyl)piperazine-1-carboxylate;

51

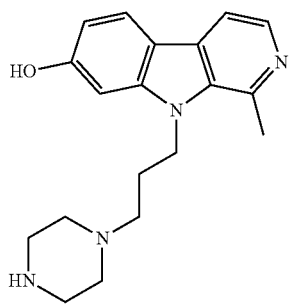 [SMILES: Cc1nccc2c3ccc(O)cc3n(CCCN3CCNCC3)c12]

1-methyl-9-(3-(piperazin-1-yl)propyl)-9H-pyrido[3,4-b]indol-7-ol;

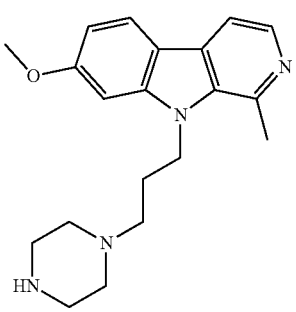 [SMILES: COc1ccc2c3ccnc(C)c3n(CCCN3CCNCC3)c2c1]

7-methoxy-1-methyl-9-(3-(piperazin-1-yl)propyl)-9H-pyrido[3,4-b]indole;

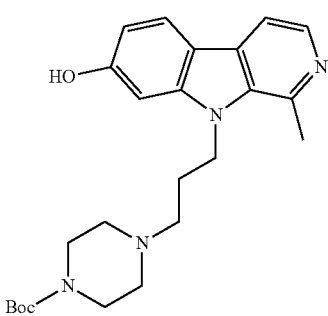 [SMILES: Cc1nccc2c3ccc(O)cc3n(CCCN3CCN(C(=O)OC(C)(C)C)CC3)c12]

tert-butyl 4-(3-(7-hydroxy-1-methyl-9H-pyrido[3,4-b]indol-9-yl)propyl)piperazine-1-carboxylate;

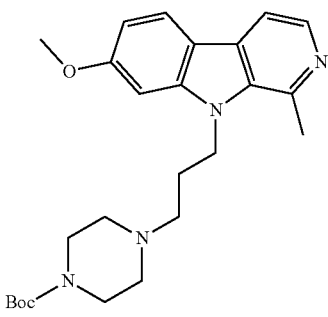 [SMILES: COc1ccc2c3ccnc(C)c3n(CCCN3CCN(C(=O)OC(C)(C)C)CC3)c2c1]

tert-butyl 4-(3-(7-methoxy-1-methyl-9H-pyrido[3,4-b]indol-9-yl)propyl)piperazine-1-carboxylate;

52

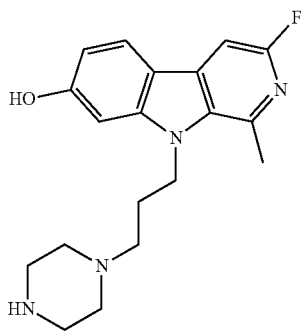 [SMILES: Cc1nc(F)cc2c3ccc(O)cc3n(CCCN3CCNCC3)c12]

3-fluoro-1-methyl-9-(3-(piperazin-1-yl)propyl)-9H-pyrido[3,4-b]indol-7-ol;

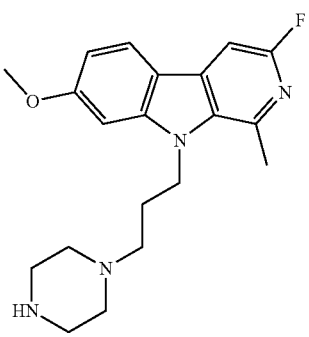 [SMILES: COc1ccc2c3cc(F)nc(C)c3n(CCCN3CCNCC3)c2c1]

3-fluoro-7-methoxy-1-methyl-9-(3-(piperazin-1-yl)propyl)-9H-pyrido[3,4-b]indole;

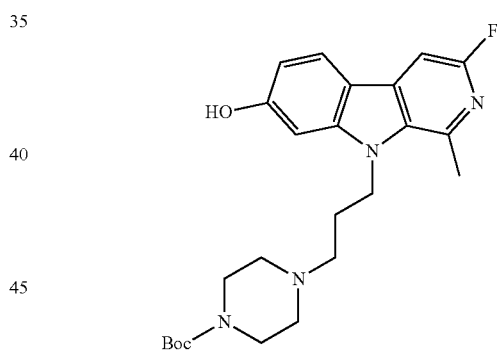

tert-butyl 4-(3-(3-fluoro-7-hydroxy-1-methyl-9H-pyrido[3,4-b]indol-9-yl)propyl)piperazine-1-carboxylate;

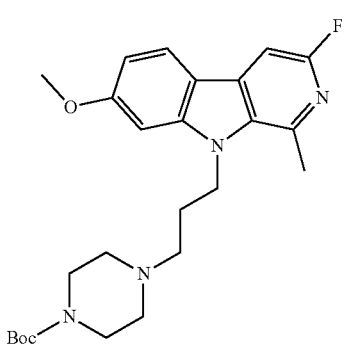 [SMILES: COc1ccc2c3cc(F)nc(C)c3n(CCCN3CCN(C(=O)OC(C)(C)C)CC3)c2c1]

tert-butyl 4-(3-(3-fluoro-7-methoxy-1-methyl-9H-pyrido[3,4-b]indol-9-yl)propyl)piperazine-1-carboxylate;

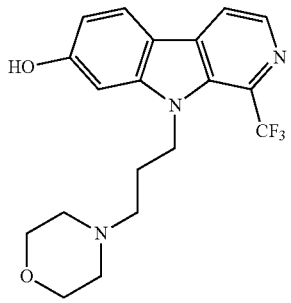 [SMILES: Oc1ccc2c3ccnc(C(F)(F)F)c3n(CCCN3CCOCC3)c2c1]

l>9-(3-morpholinopropyl)-1-(trifluoromethyl)-9H-pyrido[3,4-b]indol-7-ol;

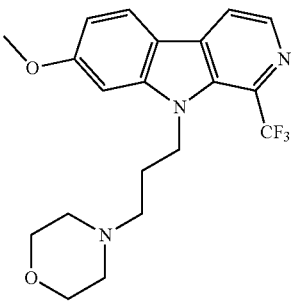 [SMILES: COc1ccc2c3ccnc(C(F)(F)F)c3n(CCCN3CCOCC3)c2c1]

4-(3-(7-methoxy-1-(trifluoromethyl)-9H-pyrido[3,4-b]indol-9-yl)propyl)morpholine;

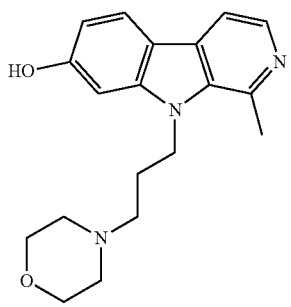 [SMILES: Cc1nccc2c3ccc(O)cc3n(CCCN3CCOCC3)c12]

1-methyl-9-(3-morpholinopropyl)-9H-pyrido[3,4-b]indol-7-ol;

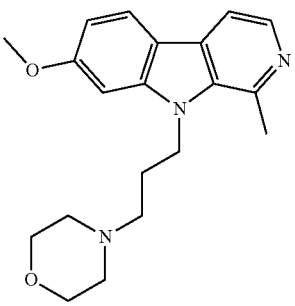 [SMILES: COc1ccc2c3ccnc(C)c3n(CCCN3CCOCC3)c2c1]

4-(3-(7-methoxy-1-methyl-9H-pyrido[3,4-b]indol-9-yl)propyl)morpholine;

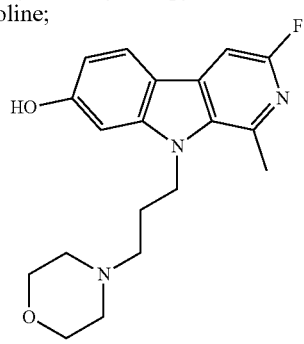

3-fluoro-1-methyl-9-(3-morpholinopropyl)-9H-pyrido[3,4-b]indol-7-ol;

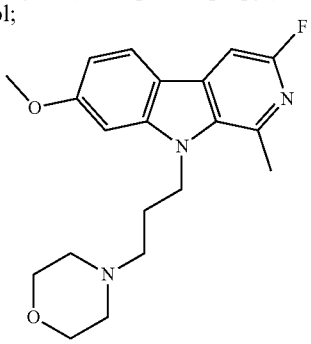

4-(3-(3-fluoro-7-methoxy-1-methyl-9H-pyrido[3,4-b]indol-9-yl)propyl)morpholine;

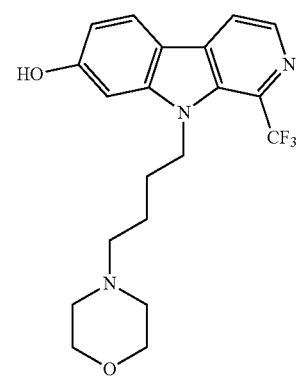

9-(4-morpholinobutyl)-1-(trifluoromethyl)-9H-pyrido[3,4-b]indol-7-ol;

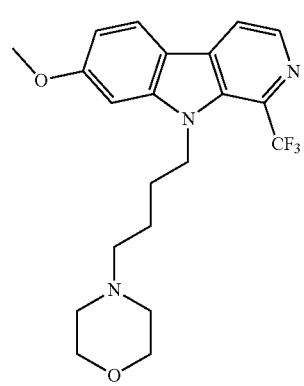

4-(4-(7-methoxy-1-(trifluoromethyl)-9H-pyrido[3,4-b]indol-9-yl)butyl)morpholine;

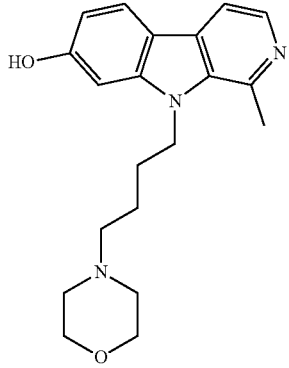 [SMILES: Cc1nccc2c3ccc(O)cc3n(CCCCN3CCOCC3)c12]

1-methyl-9-(4-morpholinobutyl)-9H-pyrido[3,4-b]indol-7-ol;

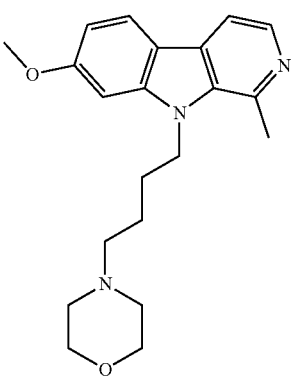 [SMILES: COc1ccc2c3ccnc(C)c3n(CCCCN3CCOCC3)c2c1]

4-(4-(7-methoxy-1-methyl-9H-pyrido[3,4-b]indol-9-yl)butyl)morpholine;

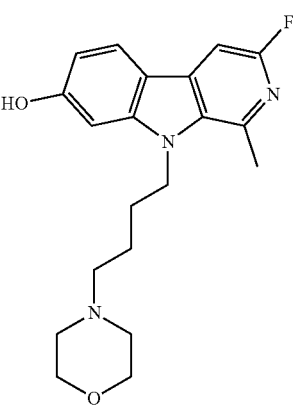 [SMILES: Cc1nc(F)cc2c3ccc(O)cc3n(CCCCN3CCOCC3)c12]

3-fluoro-1-methyl-9-(4-morpholinobutyl)-9H-pyrido[3,4-b]indol-7-ol;

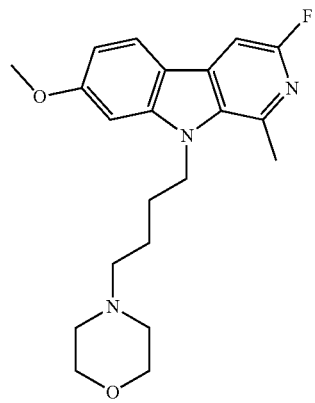 [SMILES: COc1ccc2c3cc(F)nc(C)c3n(CCCCN3CCOCC3)c2c1]

4-(4-(3-fluoro-7-methoxy-1-methyl-9H-pyrido[3,4-b]indol-9-yl)butyl)morpholine;

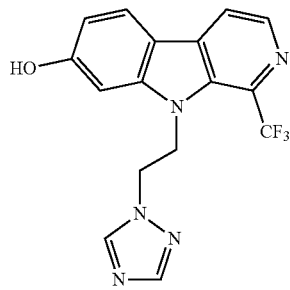

9-(2-(1H-1,2,4-triazol-1-yl)ethyl)-1-(trifluoromethyl)-9H-pyrido[3,4-b]indol-7-ol;

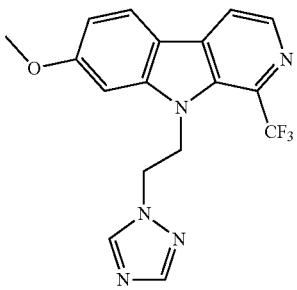 [SMILES: COc1ccc2c3ccnc(C(F)(F)F)c3n(CCn3cncn3)c2c1]

9-(2-(1H-1,2,4-triazol-1-yl)ethyl)-7-methoxy-1-(trifluoromethyl)-9H-pyrido[3,4-b]indole;

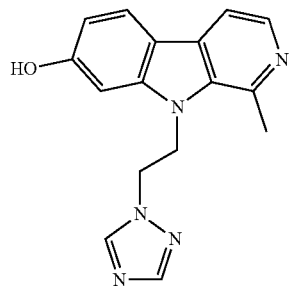 [SMILES: Cc1nccc2c3ccc(O)cc3n(CCn3cncn3)c12]

9-(2-(1H-1,2,4-triazol-1-yl)ethyl)-1-methyl-9H-pyrido[3,4-b]indol-7-ol;

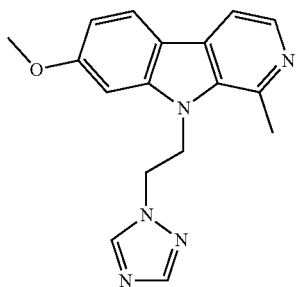 [SMILES: COc1ccc2c3ccnc(C)c3n(CCn3cncn3)c2c1]

9-(2-(1H-1,2,4-triazol-1-yl)ethyl)-7-methoxy-1-methyl-9H-pyrido[3,4-b]indole;

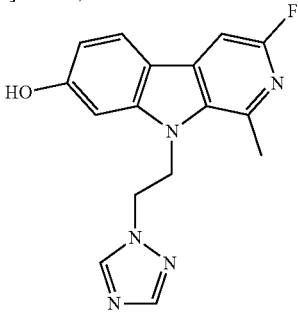

9-(2-(1H-1,2,4-triazol-1-yl)ethyl)-3-fluoro-1-methyl-9H-pyrido[3,4-b]indol-7-ol;

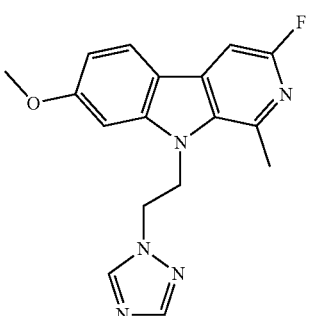 [SMILES: COc1ccc2c3cc(F)nc(C)c3n(CCn3cncn3)c2c1]

9-(2-(1H-1,2,4-triazol-1-yl)ethyl)-3-fluoro-7-methoxy-1-methyl-9H-pyrido[3,4-b]indole;

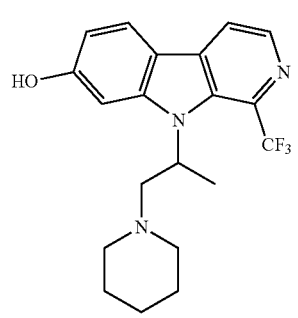

9-(1-(piperidin-1-yl)propan-2-yl)-1-(trifluoromethyl)-9H-pyrido[3,4-b]indol-7-ol;

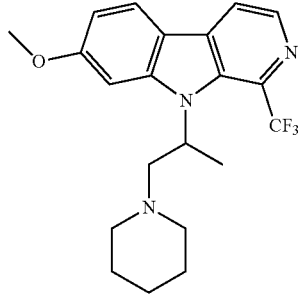 [SMILES: COc1ccc2c3ccnc(C(F)(F)F)c3n(C(C)CN3CCCCC3)c2c1]

7-methoxy-9-(1-(piperidin-1-yl)propan-2-yl)-1-(trifluoromethyl)-9H-pyrido[3,4-b]indole;

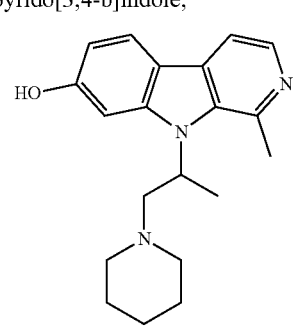

1-methyl-9-(1-(piperidin-1-yl)propan-2-yl)-9H-pyrido[3,4-b]indol-7-ol;

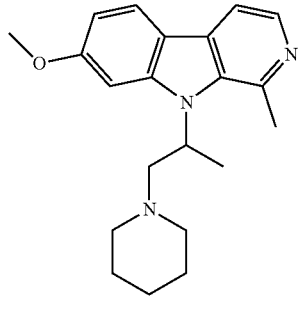 [SMILES: COc1ccc2c3ccnc(C)c3n(C(C)CN3CCCCC3)c2c1]

7-methoxy-1-methyl-9-(1-(piperidin-1-yl)propan-2-yl)-9H-pyrido[3,4-b]indole;

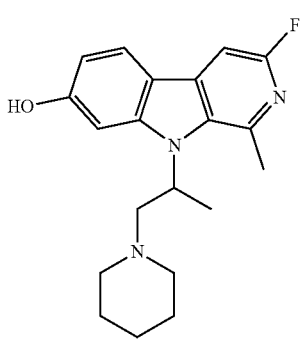 [SMILES: Cc1nc(F)cc2c3ccc(O)cc3n(C(C)CN3CCCCC3)c12]

3-fluoro-1-methyl-9-(1-(piperidin-1-yl)propan-2-yl)-9H-pyrido[3,4-b]indol-7-ol;

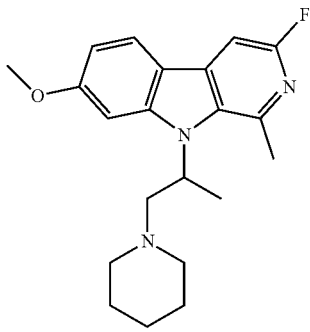 [SMILES: COc1ccc2c3cc(F)nc(C)c3n(C(C)CN3CCCCC3)c2c1]

3-fluoro-7-methoxy-1-methyl-9-(1-(piperidin-1-yl)propan-2-yl)-9H-pyrido[3,4-b]indole;

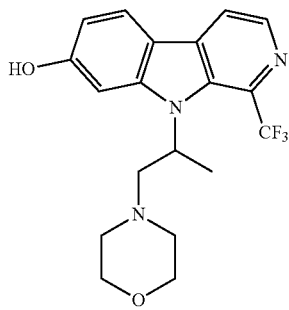

9-(1-morpholinopropan-2-yl)-1-(trifluoromethyl)-9H-pyrido[3,4-b]indol-7-ol;

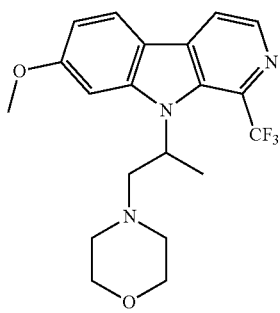

4-(2-(7-methoxy-1-(trifluoromethyl)-9H-pyrido[3,4-b]indol-9-yl)propyl)morpholine;

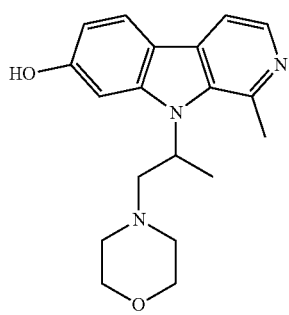 [SMILES: Cc1nccc2c3ccc(O)cc3n(C(C)CN3CCOCC3)c12]

1-methyl-9-(1-morpholinopropan-2-yl)-9H-pyrido[3,4-b]indol-7-ol;

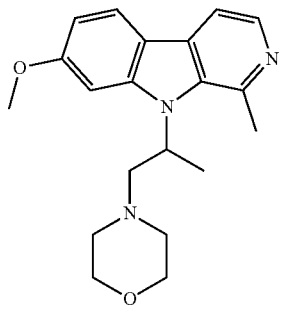 [SMILES: COc1ccc2c3ccnc(C)c3n(C(C)CN3CCOCC3)c2c1]

4-(2-(7-methoxy-1-methyl-9H-pyrido[3,4-b]indol-9-yl)propyl)morpholine;

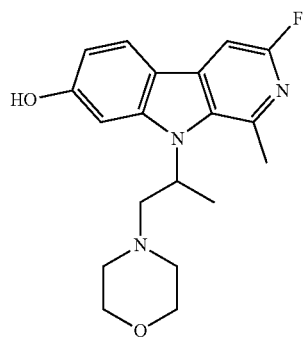 [SMILES: Cc1nc(F)cc2c3ccc(O)cc3n(C(C)CN3CCOCC3)c12]

3-fluoro-1-methyl-9-(1-morpholinopropan-2-yl)-9H-pyrido[3,4-b]indol-7-ol;

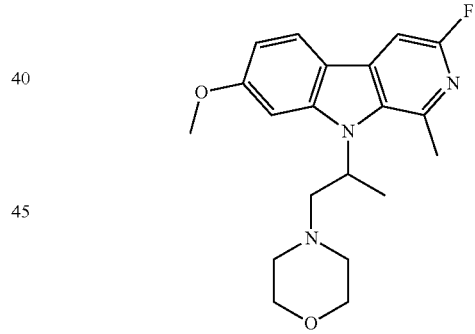

4-(2-(3-fluoro-7-methoxy-1-methyl-9H-pyrido[3,4-b]indol-9-yl)propyl)morpholine;

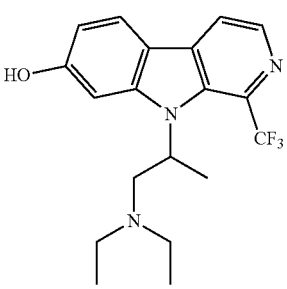

61

9-(1-(diethylamino)propan-2-yl)-1-(trifluoromethyl)-9H-pyrido[3,4-b]indol-7-ol;

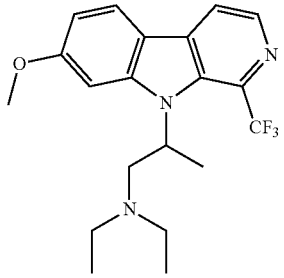 [SMILES: CCN(CC)CC(C)n1c2cc(OC)ccc2c2ccnc(C(F)(F)F)c21]

N,N-diethyl-2-(7-methoxy-1-(trifluoromethyl)-9H-pyrido[3,4-b]indol-9-yl)propan-1-amine;

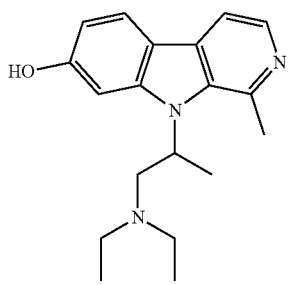 [SMILES: CCN(CC)CC(C)n1c2cc(O)ccc2c2ccnc(C)c21]

9-(1-(diethylamino)propan-2-yl)-1-methyl-9H-pyrido[3,4-b]indol-7-ol;

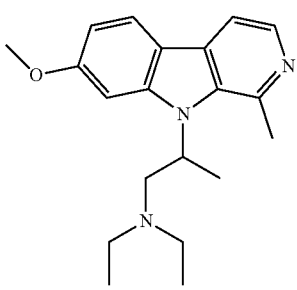 [SMILES: CCN(CC)CC(C)n1c2cc(OC)ccc2c2ccnc(C)c21]

N,N-diethyl-2-(7-methoxy-1-methyl-9H-pyrido[3,4-b]indol-9-yl)propan-1-amine;

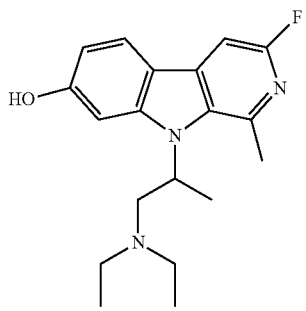 [SMILES: CCN(CC)CC(C)n1c2cc(O)ccc2c2cc(F)nc(C)c21]

9-(1-(diethylamino)propan-2-yl)-3-fluoro-1-methyl-9H-pyrido[3,4-b]indol-7-ol;

62

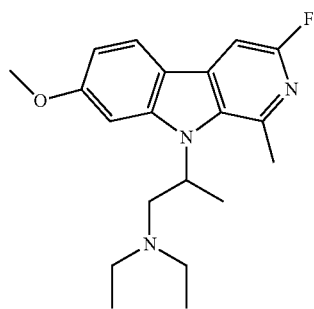 [SMILES: CCN(CC)CC(C)n1c2cc(OC)ccc2c2cc(F)nc(C)c21]

N,N-diethyl-2-(3-fluoro-7-methoxy-1-methyl-9H-pyrido[3,4-b]indol-9-yl)propan-1-amine;

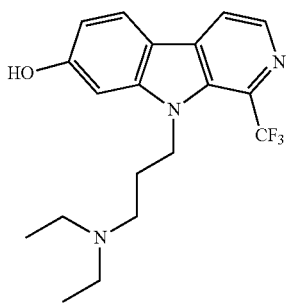 [SMILES: CCN(CC)CCCn1c2cc(O)ccc2c2ccnc(C(F)(F)F)c21]

9-(3-(diethylamino)propyl)-1-(trifluoromethyl)-9H-pyrido[3,4-b]indol-7-ol;

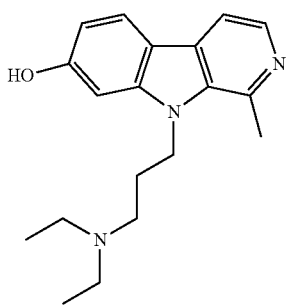 [SMILES: CCN(CC)CCCn1c2cc(O)ccc2c2ccnc(C)c21]

N,N-diethyl-3-(7-methoxy-1-(trifluoromethyl)-9H-pyrido[3,4-b]indol-9-yl)propan-1-amine;

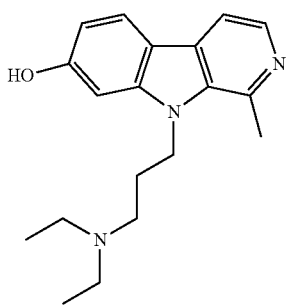 [SMILES: CCN(CC)CCCn1c2cc(O)ccc2c2ccnc(C)c21]

9-(3-(diethylamino)propyl)-1-methyl-9H-pyrido[3,4-b]indol-7-ol;

63

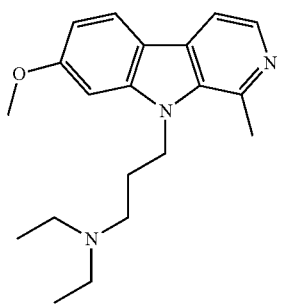 [SMILES: CCN(CC)CCCn1c2cc(OC)ccc2c2ccnc(C)c21]

N,N-diethyl-3-(7-methoxy-1-methyl-9H-pyrido[3,4-b]indol-9-yl)propan-1-amine;

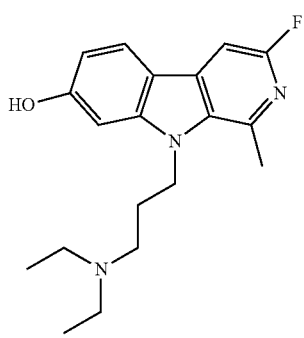 [SMILES: CCN(CC)CCCn1c2cc(O)ccc2c2cc(F)nc(C)c21]

9-(3-(diethylamino)propyl)-3-fluoro-1-methyl-9H-pyrido[3,4-b]indol-7-ol;

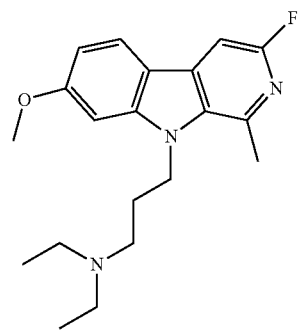 [SMILES: CCN(CC)CCCn1c2cc(OC)ccc2c2cc(F)nc(C)c21]

N,N-diethyl-3-(3-fluoro-7-methoxy-1-methyl-9H-pyrido[3,4-b]indol-9-yl)propan-1-amine;

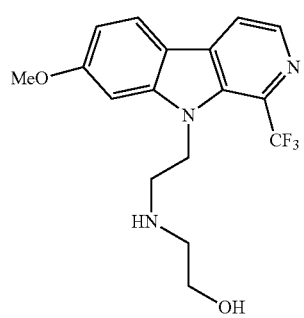 [SMILES: COc1ccc2c3ccnc(C(F)(F)F)c3n(CCNCCO)c2c1]

64

2-((2-(7-methoxy-1-(trifluoromethyl)-9H-pyrido[3,4-b]indol-9-yl)ethyl)amino)ethanol;

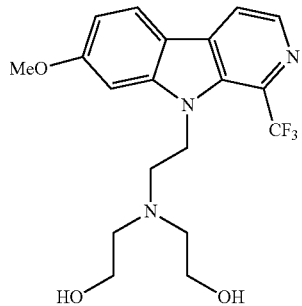 [SMILES: COc1ccc2c3ccnc(C(F)(F)F)c3n(CCN(CCO)CCO)c2c1]

2,2'-((2-(7-methoxy-1-(trifluoromethyl)-9H-pyrido[3,4-b]indol-9-yl)ethyl) azanediyl)diethanol;

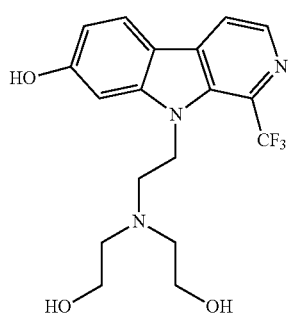 [SMILES: OCCN(CCO)CCn1c2cc(O)ccc2c2ccnc(C(F)(F)F)c21]

2,2'-((2-(7-hydroxy-1-(trifluoromethyl)-9H-pyrido[3,4-b]indol-9-yl)ethyl) azanediyl)diethanol;

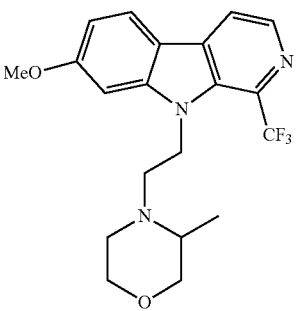 [SMILES: COc1ccc2c3ccnc(C(F)(F)F)c3n(CCN3CCOCC3C)c2c1]

4-(2-(7-methoxy-1-(trifluoromethyl)-9H-pyrido[3,4-b]indol-9-yl)ethyl)-3-methylmorpholine;

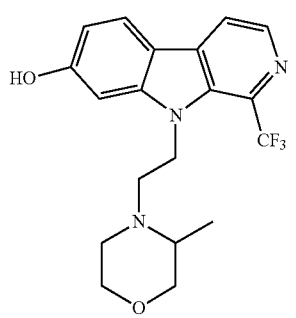 [SMILES: CC1COCCN1CCn1c2cc(O)ccc2c2ccnc(C(F)(F)F)c21]

9-(2-(3-methylmorpholino)ethyl)-1-(trifluoromethyl)-9H-pyrido[3,4-b]indol-7-ol;

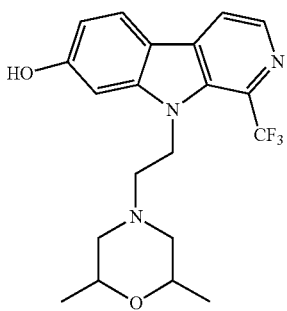 [SMILES: CC1CN(CCn2c3cc(O)ccc3c3ccnc(C(F)(F)F)c32)CC(C)O1]

9-(2-(2,6-dimethylmorpholino)ethyl)-1-(trifluoromethyl)-9H-pyrido[3,4-b]indol-7-ol;

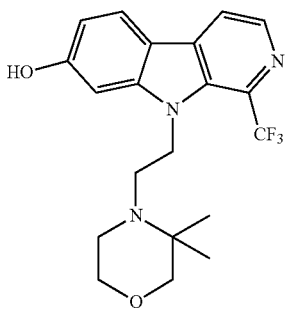 [SMILES: CC1(C)COCCN1CCn1c2cc(O)ccc2c2ccnc(C(F)(F)F)c21]

9-(2-(3,3-dimethylmorpholino)ethyl)-1-(trifluoromethyl)-9H-pyrido[3,4-b]indol-7-ol;

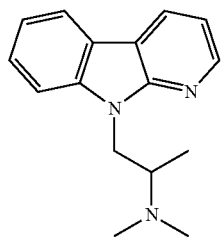 [SMILES: CC(Cn1c2ccccc2c2cccnc21)N(C)C]

N,N-dimethyl-1-(9H-pyrido[2,3-b]indol-9-yl)propan-2-amine;

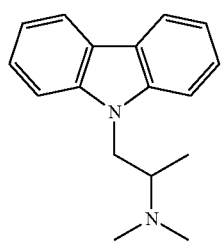 [SMILES: CC(Cn1c2ccccc2c2ccccc21)N(C)C]

1-(9H-carbazol-9-yl)-N,N-dimethylpropan-2-amine.

In some embodiments, the invention provides a formate salt of a compound according to any of the compounds described above. In some embodiments, the invention provides a citrate salt of a compound according to any of the compounds described above. In some embodiments, the invention provides a hydrochloric salt of a compound according to any of the compounds described above.

In some embodiments, the invention provides a pharmaceutical composition comprising a compound according to Formula I and a pharmaceutically acceptable excipient. Further provided herein are pharmaceutical compositions comprising compounds of Formula IA, or Formula IB, or Formula IC. Further provided herein are pharmaceutical compositions comprising compounds of Formula ID.

In a further aspect, the invention provides compounds of Formula III:

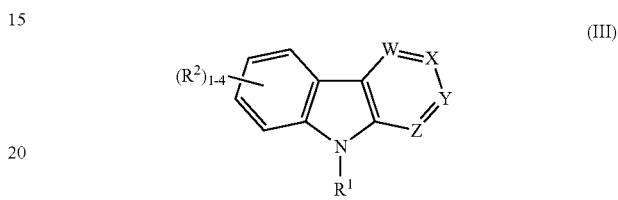

or a salt, hydrate, or isomer thereof; wherein
$R^1$ is H or $C_{1-6}$ alkyl;
W is selected from $CR^{3a}$ and N, wherein N is optionally oxidized to the corresponding N-oxide;
X is selected from $CR^{3b}$ and N, wherein N is optionally oxidized to the corresponding N-oxide;
Y is $CR^{3c}$;
Z is selected from $CR^{3d}$ and N, wherein N is optionally oxidized to the corresponding N-oxide;
each $R^2$, $R^{3a}$, $R^{3b}$, $R^{3c}$ and $R^{3d}$ is independently selected from the group consisting of H, halogen, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, aryloxy, $C_{1-6}$ alkyl-OH, —$OR^4$, —$C_{0-6}$ alkyl-$NR^4R^5$, —$SR^4$, —$C(O)R^4$, —$C_{0-6}$ alkyl-$C(O)OR^4$, —$C(O)NR^4R^5$, —$N(R^4)C(O)R^5$, —$N(R^4)C(O)OR^5$, —$N(R^4)C(O)NR^4R^5$, —$OP(O)(OR^4)_2$, —$S(O)_2OR^4$, —$S(O)_2NR^4R^5$, —CN, cycloalkyl, heterocycloalkyl, aryl and heteroaryl; alternatively, two $R^2$ groups on adjacent atoms can be combined with the atoms to which they are attached to form a member selected from the group consisting of cycloalkyl, heterocycloalkyl, aryl and heteroaryl; and
each $R^4$, $R^5$, $R^6$, and $R^7$ is independently selected from the group consisting of H, $C_{1-6}$ alkyl, and $C_{1-6}$ alkyl-OH.

In one group of embodiments of Formula (III),
$R^1$ is H or $C_{1-6}$ alkyl;
W is $CR^{3a}$;
X is $CR^{3b}$;
Y is $CR^{3c}$; and
Z is N, wherein N is optionally oxidized to the corresponding N-oxide.

In another group of embodiments of Formula (III),
$R^1$ is H or $C_{1-6}$ alkyl;
W is $CR^{3a}$;
X is N, wherein N is optionally oxidized to the corresponding N-oxide;
Y is $CR^{3c}$; and
Z is $CR^{3d}$.

In yet another group of embodiments of Formula (III),
$R^1$ is H or $C_{1-6}$ alkyl;
W is N, wherein N is optionally oxidized to the corresponding N-oxide;
X is $CR^{3a}$;
Y is $CR^{3c}$; and
Z is $CR^{3d}$.

In some embodiments of Formula (III), or a salt, hydrate, or isomer thereof are compounds wherein $R^1$ is H.

In some embodiments of Formula (III), or a salt, hydrate, or isomer thereof; are compounds wherein $R^1$ is $C_{1-6}$ alkyl.

In some embodiments, the compound of Formula (III) is not 1-(9H-carbazol-9-yl)-N,N-dimethylpropan-2-amine or 1-amino-3-(3,6-dibromo-9H-carbazol-9-yl)propan-2-ol.

In one embodiment, provided is a formate salt of a compound of Formula (III).

In one embodiment, provided is a citrate salt of a compound of Formula (III).

In one embodiments, provided is a hydrochloric salt of a compound of Formula (III).

In some embodiments, the invention provides a pharmaceutical composition comprising a compound of Formula (III).

The compounds and compositions of the present invention can also include salts, hydrates, solvates, and prodrug forms. The compounds and compositions of the present invention can also include the isomers and metabolites of compounds of Formula I, IA, IB, IC, ID, II, and/or III.

The compounds of the present invention can be in the salt form. Salts include, but are not limited to, sulfate, citrate, acetate, oxalate, chloride, bromide, iodide, nitrate, bisulfate, phosphate, acid phosphate, phosphonic acid, isonicotinate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. Other salts include, but are not limited to, salts with inorganic bases include alkali metal salts such as sodium salts, and potassium salts; alkaline earth metal salts such as calcium salts, and magnesium salts; aluminum salts; and ammonium salts. Other salts with organic bases include salts with diethylamine, diethanolamine, meglumine, and N,N'-dibenzylethylenediamine. In some embodiments, the present invention provides the hydrochloride salt.

In some embodiments, the compounds of the present invention comprise nitrogen atoms which are optionally further oxidized, i.e., the compounds are N-oxides. By way of example only, ine one instance, a nitrogen atom in a pyrido-indolyl ring system in a compound of Formula (I) is oxidized to the corresponding N-oxide.

In some embodiments, the compounds described herein are delivered and/or formulated as prodrugs. In one embodiment, any compound described herein is an ester prodrug. In another embodiment, any compound described herein is an amide prodrug. In further embodiments, the prodrug moieties comprise conjugated groups which allow selective targeting at a bone structure. Examples of such motifs are described in Erez et al., *Bioorg. Med. Chem. Lett.* 2008, 18, 816-820 and Neale et al., *Bioorg. Med. Chem. Lett.* 2009, 19, 680-683 and are incorporated herein by reference. Accordingly, contemplated within the scope of embodiments presented herein are estradiol conjugates and/or bisphosphonate conjugates of compounds of Formula (I), Formula (II), and/or Formula (III).

The compounds of the present invention can be made by a variety of methods known to one of skill in the art (see Comprehensive Organic Transformations Richard C. Larock, 1989). One of skill in the art will appreciate that other methods of making the compounds are useful in the present invention. Exemplary methods for the synthesis of compounds of Formula I, Formula II and Formula III are described in the Examples section and in Scheme 1 below.

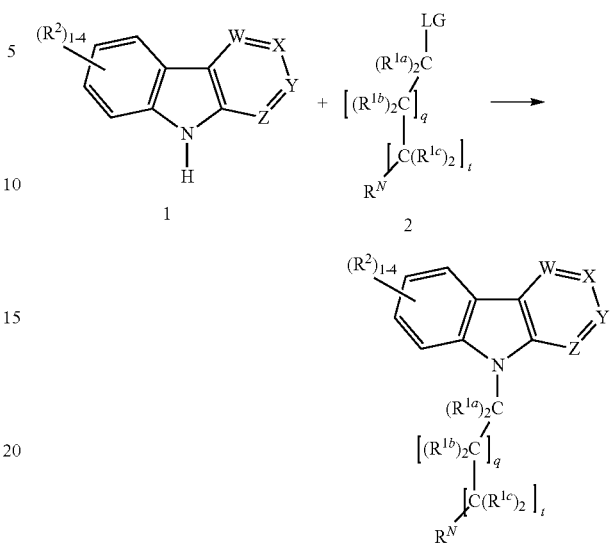

Scheme 1

Starting with a compound 1, reaction with a compound 2 comprising a leaving group (LG) provides compounds of Formula I or Formula II. Various leaving groups are suitable including and not limited to halo, activated esters, mesylates, triflates or any other suitable leaving groups which allow for the attachment of the group

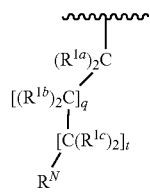

at the 9-position of the core ring system. Optionally, compounds of Formula III are converted to compounds of Formula I or Formula II. Optionally, where $R^2$ is a methoxy, it can be converted to a hydroxy group by demethylation using procedures described, for example, HBr in acetic acid, or boron tribromide, or any other suitable procedure. Optionally, compounds of Formula I or Formula II comprise N-oxides which are prepared by oxidation using, for example, chloroperbenzoic acid.

IV. Methods of Promoting Bone Formation

In another aspect, the present invention provides a method of promoting bone formation in a subject in need thereof, by administering to the subject a therapeutically effective amount of a compound of the present invention (e.g., a compound or composition of Formula I, Formula IA, Formula IB, Formula IC, Formula II, or Formula III as described in Section III above).

In some embodiments, the present invention provides a method of promoting bone formation in a subject in need thereof, comprising administering to the subject a therapeutically effective amount of a compound of Formula II:

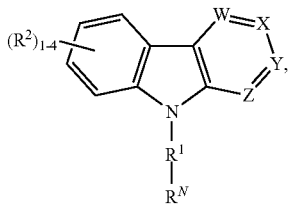

(II)

or a salt, hydrate, or isomer thereof; wherein
W is selected from $CR^{3a}$ and N, wherein N is optionally oxidized to the corresponding N-oxide;
X is selected from $CR^{3b}$ and N, wherein N is optionally oxidized to the corresponding N-oxide;
Y is selected from $CR^{3c}$ and N, wherein N is optionally oxidized to the corresponding N-oxide;
Z is selected from $CR^{3d}$ and N, wherein N is optionally oxidized to the corresponding N-oxide;
$R^N$ is selected from the group consisting of $NR^6R^7$, heterocyclyl, and heteroaryl, wherein heterocyclyl and heteroaryl comprise from about 5 to about 10 ring atoms, at least one of which is nitrogen, and wherein any N in $R^N$ is optionally oxidized to the corresponding N-oxide; $R^1$ is —$C_{1-6}$ alkyl-; each $R^2$, $R^{3a}$, $R^{3b}$, $R^{1c}$ and $R^{3d}$ is independently selected from the group consisting of H, halogen, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkyl-OH, —$OR^4$, —$C_{0-6}$ alkyl-$NR^4R^5$, —$SR^4$, —$C(O)R^4$, —$C_{0-6}$ alkyl-$C(O)OR^4$, —$C(O)NR^4R^5$, —$N(R^4)C(O)R^5$, —$N(R^4)C(O)OR^5$, —$N(R^4)C(O)NR^4R^5$, —$OP(O)(OR^4)_2$, —$S(O)_2OR^4$, —$S(O)_2NR^4R^5$, —CN, cycloalkyl, heterocycloalkyl, aryl and heteroaryl;
alternatively, two $R^2$ groups on adjacent atoms can be combined with the atoms to which they are attached to form a member selected from the group consisting of cycloalkyl, heterocycloalkyl, aryl and heteroaryl; and
each $R^4$, $R^5$, $R^6$, and $R^7$ is independently selected from the group consisting of H, $C_{1-6}$ alkyl, and $C_{1-6}$ alkyl-OH;
thereby promoting bone formation in the subject.
In some embodiments,
$R^1$ is —$C(R^{1a})_2$—$[C(R^{1b})_2]_q$—$[C(R^{1c})_2]_t$, wherein each $R^{1a}$, $R^{1b}$ and $R^{1c}$ is independently selected from H, methyl, and ethyl, and wherein the total number of carbon atoms in the group —$C(R^{1a})_2$—$[C(R^{1b})_2]_q$—$[C(R^{1c})_2]_t$— does not exceed six;
the subscript q is an integer from 0 to 4; and
the subscript t is an integer from 0 to 4;
provided that when:
a) the sum of q and t is, 1 and
b) either of $R^6$ or $R^7$, if present, is H or $C_{1-6}$ alkyl,
at least one of $R^{1a}$ and $R^{1b}$ is other than H; and
provided that when the sum of q and t is 2,
a) $R^2$ is other than H, and
b) at least one of $R^6$ and $R^7$, if present, is other than H or methyl.
In some embodiments, the compound is selected from the group consisting of:
9-(2-(dimethylamino)propyl)-9H-pyrido[3,4-b]indol-7-ol;
9-(2-(dimethylamino)propyl)-1-methyl-9H-pyrido[3,4-b]indol-7-ol;
N,N-dimethyl-1-(9H-pyrido[2,3-b]indol-9-yl)propan-2-amine;
N,N-dimethyl-1-(9H-pyrido[3,4-b]indol-9-yl)propan-2-amine;
1-(9H-carbazol-9-yl)-N,N-dimethylpropan-2-amine;
1-(7-methoxy-9H-pyrido[3,4-b]indol-9-yl)-N,N-dimethylpropan-2-amine;
1-(2-methoxy-9H-carbazol-9-yl)-N,N-dimethylpropan-2-amine;
4-(3-(7-methoxy-1-methyl-9H-pyrido[3,4-b]indol-9-yl)propyl)morpholine;
N,N-diethyl-3-(7-methoxy-1-methyl-9H-pyrido[3,4-b]indol-9-yl)propan-1-amine;
7-methoxy-1-methyl-9-(3-(piperazin-1-yl)propyl)-9H-pyrido[3,4-b]indole;
2-(7-methoxy-1-methyl-9H-pyrido[3,4-b]indol-9-yl)-N,N-dimethylpropan-1-amine;
N,N-diethyl-2-(7-methoxy-1-methyl-9H-pyrido[3,4-b]indol-9-yl)propan-1-amine;
7-methoxy-1-methyl-9-(2-(piperazin-1-yl)ethyl)-9H-pyrido[3,4-b]indole;
4-(2-(7-methoxy-1-methyl-9H-pyrido[3,4-b]indol-9-yl)ethyl)morpholine;
4-(2-(7-methoxy-1-methyl-9H-pyrido[3,4-b]indol-9-yl)propyl)morpholine;
7-methoxy-1-methyl-9-(1-(piperidin-1-yl)propan-2-yl)-9H-pyrido[3,4-b]indole;
9-(2-(4H-1,2,4-triazol-3-yl)ethyl)-7-methoxy-1-methyl-9H-pyrido[3,4-b]indole;
2-(2-(7-methoxy-1-methyl-9H-pyrido[3,4-b]indol-9-yl)ethyl)-1,3,4-oxadiazole;
5-(2-(7-methoxy-1-methyl-9H-pyrido[3,4-b]indol-9-yl)ethyl)-1,2,4-oxadiazole;
9-(2-(1H-1,2,4-triazol-1-yl)ethyl)-7-methoxy-1-methyl-9H-pyrido[3,4-b]indole;
9-(3-(4H-1,2,4-triazol-3-yl)propyl)-7-methoxy-1-methyl-9H-pyrido[3,4-b]indole;
2-(3-(7-methoxy-1-methyl-9H-pyrido[3,4-b]indol-9-yl)propyl)-1,3,4-oxadiazole;
5-(3-(7-methoxy-1-methyl-9H-pyrido[3,4-b]indol-9-yl)propyl)-1,2,4-oxadiazole;
9-(3-(1H-1,2,4-triazol-1-yl)propyl)-7-methoxy-1-methyl-9H-pyrido[3,4-b]indole; and
2-(7-methoxy-1-methyl-9H-pyrido[3,4-b]indol-9-yl)-N,N-dimethylethanamine;
or salts, hydrates, or isomers thereof.
In some embodiments, the method comprises administering to the subject a therapeutically effective amount of formate salt or a citrate salt of a compound of Formula II.
One of skill in the art will appreciate that bone formation can be local, systemic, or both local and systemic. In some embodiments, bone formation is local. A subject in need of local bone formation may have any of a variety of ailments or disease states (including but not limited to, weakened bone, fractured bone, or a disease or condition characterized by low bone mass such as described herein). In some embodiments, the subject is in need of a spinal fusion, arthrodesis, or an orthopedic, dental, or periodontal synthetic bone graft or implant. In some embodiments, the present invention provides a method of promoting bone formation at a site of injury or localized condition. In some embodiments, the present invention comprises a method of fusing bones (e.g., at a site of injury). In some embodiments, the site of injury is a surgical site. In other embodiments, the injury is a fracture or weakened bone or periodontal disease.
In some embodiments, bone formation is systemic. Systemic bone formation refers to the formation of bone throughout the subject, and can affect all the bones in the subject's body. A subject in need of systemic bone formation can suffer from any of a variety of ailments or disease states. In some embodiments, the subject suffers from a low bone mass phenotype disease, a bone fracture, or periodontal disease. In some embodiments, the subject suffers from a low bone mass phenotype disease. Low bone mass can be determined by a variety of methods known to one of skill in the art. For example, low bone mass can be characterized by a T-score less than about −0.5. Low bone mass phenotype diseases can include osteoporosis, osteopenia, and osteoporosis-pseudoglioma syndrome (OPPG). In some other embodiments, the low bone mass phenotype disease can be osteopenia or osteoporosis-pseudoglioma syndrome (OPPG).

Local and/or systemic bone formation using a compound or composition of the present invention can be achieved according to any of a variety of methods. Methods of formulating and administering the compounds and compositions of the present invention (e.g., a compound or composition of Formula I, Formula IA, Formula IB, Formula IC, Formula II, or Formula III) are described in Section VII below. In some embodiments, the method of promoting bone formation comprises implanting a subject in need thereof a medical device as described herein (e.g., in Section VIII below).

The methods of promoting bone formation can be used to treat diseases characterized by secondary induced osteoporosis (low bone mass) including, but not limited to, osteomalacia, Polyostotic fibrous dysplasia, osteogenesis imperfecta, Paget's disease, rheumatoid arthritis, zero gravity, osteoarthritis, Prolonged inactivity or immobility, arthrodesis, osteomyelitis, Celiac disease, Crohn's Disease, Ulcerative Colitis, inflammatory bowel disease, gastrectomy, secondary induced osteoporosis, Amennorhea, Cushing's Disease, Cushing's syndrome, Diabetes Mellitus, Diabetes, Eating Disorders, Hyperparathyroidism, Hyperthyroidism, Hyperprolactinemia, Kleinefelter Syndrome, Thyroid Disease, Turner Syndrome, steroid induced osteoporosis, seizure or depression induced osteoporosis, immobility, arthritis, cancer induced secondary osteoporosis, Gonadotropin-releasing hormone agonists induced low bone mass, Thyroid medication induced low bone mass, Dilantin (phenytoin), depakote induced low bone mass, chemotherapy induced low bone mass, Immunosuppressant induced low bone mass, Blood thinning agents induced low bone mass, Grave's disease, Juvenile rheumatoid arthritis, Malabsorption syndromes, Anorexia nervosa, Kidney disease, Anticonvulsant treatment (e.g., for epilepsy), Corticosteroid treatment (e.g., for rheumatoid arthritis, asthma), Immunosuppressive treatment (e.g., for cancer), Inadequate nutrition (especially calcium, vitamin D), Excessive exercise leading to amenorrhea (absence of periods), Smoking, and Alcohol abuse, pregnancy-associated osteoporosis, copper deficiency, Dibasic aminoaciduria type 2, Werner's syndrome, Hajdu-Cheney syndrome, Hyperostosis corticalis deformans juvenilis, Methylmalonic aciduria type 2, Cystathionine beta-synthase deficiency, Exemestane, Hyperimmunoglobulin E (IgE) syndrome, Haemochromatosis, Singleton-Merten syndrome, Beta thalassaemia (homozygous), Reflex sympathetic osteodystrophy, Sarcoidosis, Winchester syndrome, Hallermann-Streiff syndrome (HSS), Cyproterone, Glycerol kinase deficiency, Bonnet-Dechaume-Blanc syndrome, Prednisolone, Heparin, Geroderma osteodysplastica, Torg osteolysis syndrome, Orchidectomy, Fabry's disease, Pseudoprogeria syndrome, Wolcott-Rallison syndrome, Ankylosing spondylitis, Myeloma, Systemic infantile hyalinosis, Albright's hereditary osteodystrophy, Anorexia Nervosa, Autoimmune Lymphoproliferative Syndrome, Brown-Sequard Syndrome, Diamond-Blackfan anemia, Eating disorders, Galactorrhoea-Hyperprolactinaemia, Gonadal dysgenesis, Kidney conditions, Menkes Disease, Menopause, Neuritis, Ovarian insufficiency due to FSH resistance, Familial Ovarian insufficiency, Premature aging, Primary biliary cirrhosis, Prolactinoma, Familial Prolactinoma, Renal osteodystrophy, Ulcerative colitis, Underweight, Werner syndrome, Bone tumor, Bone cancer, Brittle bone disease, Osteonecrosis, Osteogenesis imperfecta congenita, Osteogenesis imperfecta tarda, and periodontal disease. One of skill in the art will appreciate that other types of conditions, diseases and treatments lead to osteoporosis.

Bone formation can be measured according to any of a variety of ways known to one of skill in the art. Methods of measuring bone formation include, but are not limited to, Uct (micro CT), Dual X-ray absorption (Bone density), ultrasound, QCT, SPA, DPA, DXR, SEXA, QUS, X-ray, using the human eye during surgically manipulation, Alizarin red S, serum osteocalcin, serum alkaline phosphatase, Serum bone Gla-protein (BGP), bone mineral content, serum calcium, serum phosphorus, tantalum markers, and serum IGF-1.

Many indicators of bone formation can be used to measure and/or quantify the amount of bone formation, including bone density. In some embodiments, bone formation can be demonstrated by an increase of 0.1% in bone density. In other embodiments, bone growth can be demonstrated by an increase of 0.2%, 0.3%, 0.4%, 0.5%, 0.6%, 0.7%, 0.8%, 0.9%, 1%, 2%, 3%, 4%, 5%, 10%, 20%, 30%, 40%, 50%, 60%, 70%, 80%, 90%, 100%, 200%, 300%, 400%, 500%, 600%, 700%, 800%, 900% or 1000% or greater, in bone density. Bone density can be measured by a variety of different methods, including the T-score and Z-score. The Z-score is the number of standard deviations above or below the mean for the patient's age and sex. The T-score is the number of standard deviations above or below the mean for a healthy 30 year old adult of the same sex as the patient. Low bone mass is characterized by a T-score of −1 to −2.15. Osteoporosis is characterized by a T-score less than −2.15. Improvement in the T-score or Z-score indicate bone growth. Bone density can be measured in a variety of places of the skeleton, such the spine or the hip. One of skill in the art will appreciate that other methods of determining bone density are useful in the present invention.

V. Methods of Treating Renal Damage

In another aspect, the present invention provides a method of treating renal damage by administering to a subject suffering from renal damage, a therapeutically effective amount of a compound of the present invention (e.g., a compound or composition of Formula I, Formula IA, Formula IB, Formula IC, Formula II, or Formula III as described in Section III above).

Renal damage can be caused by a variety of ailments known to one of skill in the art. In some embodiments, renal damage is caused by infection, radiation, toxin, dehydration or trauma. Toxins causing renal damage include, but are not limited to, chemicals, poisons, and chemotherapeutic agents. One of skill in the art will appreciate that other causes of renal damage can be treated by the methods of the present invention.

Renal damage treatable by the compounds of the present invention includes acute renal failure. Acute renal failure is also known as acute kidney failure or acute kidney injury. Acute renal failure results in retention of nitrogenous (urea and creatinine) and non-nitrogenous waste products that are normally excreted by the kidney. Depending on the severity and duration of the renal dysfunction, this accumulation is accompanied by metabolic disturbances, such as metabolic acidosis (acidification of the blood) and hyperkalaemia (elevated potassium levels), changes in body fluid balance, and effects on other organ systems. Acute renal failure can be characterized by oliguria or anuria (decrease or cessation of urine production), although nonliguric acute renal failure can also occur.

A subject can be characterized as being at (1) a risk for acute damage; (2) kidney damage resulting in injury; (3) acute renal failure; and (4) loss of kidney function. Risk for acute kidney damage is characterized by serum creatinine increased 1.5 times or urine production of <0.5 ml/kg body weight over 6 hours. Injury is reached when serum creatinine increased 2.0 times or urine production <0.5 ml/kg over 12 hours. Failure is reached when serum creatinine increased 3.0 times or creatinine >35504 (with a rise of >44) or urine output below 0.3 ml/kg over 24 hours. Loss of kidney function is reached when a subject suffers from persistent acute renal failure or more than four weeks of complete loss of kidney function.

Kidney biopsy can be performed in the setting of acute renal failure, to provide a definitive diagnosis and sometimes an idea of the prognosis, unless the cause is clear and appropriate screening investigations are reassuringly negative.

Renal therapeutic agents of the invention can be used in subjects that have received renal injury, or those at risk of chronic renal failure. As used herein, a subject is said to be in, or at risk for, chronic renal failure, or at risk of the need for renal replacement therapy (i.e., chronic hemodialysis, continuous peritoneal dialysis, or kidney transplantation), if the subject is reasonably expected to suffer a progressive loss of renal function associated with progressive loss of functioning nephron units. Whether a particular subject is in, or at risk of, chronic renal failure is a determination which may routinely be made by one of ordinary skill in the relevant medical or veterinary art. Subjects in, or at risk of, chronic renal failure, or at risk of the need for renal replacement therapy, include but are not limited to the following: subjects which can be regarded as afflicted with chronic renal failure, end-stage renal disease, chronic diabetic nephropathy, hypertensive nephrosclerosis, chronic glomerulonephritis, hereditary nephritis, and/or renal dysplasia; subjects having a biopsy indicating glomerular hypertrophy, tubular hypertrophy, chronic glomerulosclerosis, renal cell carcinoma, and/or chronic tubulointerstitial sclerosis; subjects having an ultrasound, MRI, CAT scan, or other non-invasive examination indicating renal fibrosis; subjects having an unusual number of broad casts present in urinary sediment; subjects having a GFR which is chronically less than about 50%, and more particularly less than about 40%, 30% or 20%, of the expected GFR for the subject; human male subjects weighing at least about 50 kg and having a GFR which is chronically less than about 50 ml/min, and more particularly less than about 40 ml/min 30 ml/min or 20 ml/min; human female subjects weighing at least about 40 kg and having a GFR which is chronically less than about 40 ml/min, and more particularly less than about 30 ml/min, 20 ml/min or 10 ml/min; subjects possessing a number of functional nephron units which is less than about 50%, and more particularly less than about 40%, 30% or 20%, of the number of functional nephron units possessed by a healthy but otherwise similar subject; subjects which have a single kidney; and subjects which are kidney transplant recipients.

VI. Methods of Treating Cancer

The compounds and compositions of the present invention are also useful in the treatment of cancer. Accordingly, some embodiments of the invention provide a method of treating cancer. The method includes administering to a subject in need thereof a therapeutically effective amount of a compound of the present invention (e.g., a compound or composition of Formula I, Formula IA, Formula IB, Formula IC, Formula II, or Formula III as described in Section III above).

In some embodiments, the compounds of the present invention are useful in the treatment of proliferative disorders such as cancers, leukaemias and other disorders associated with uncontrolled cellular proliferation such as psoriasis and restenosis. As defined herein, an anti-proliferative effect within the scope of the present invention may be demonstrated by the ability to inhibit cell proliferation in an in vitro whole cell assay, for example using any of the cell lines A549, HT29, Saos-2, HeLa or MCF-7, or by showing inhibition of a CDK enzyme (such as CDK2 or CDK4) in an appropriate assay. Using such cell line and enzymes assays it may be determined whether a compound is anti-proliferative in the context of the present invention.

As used herein, the term "cancer" includes, but is not limited to the following cancers: breast, ovary, cervix, prostate, testis, genitourinary tract, esophagus, larynx, glioblastoma, neuroblastoma, stomach, skin, keratoacanthoma, lung, epidermoid carcinoma, large cell carcinoma, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colon-rectum, large intestine, rectum, brain and central nervous system, and leukemia. One of skill in the art will appreciate that other cancers and proliferative disorders can be treated by the compounds and compositions of the present invention.

In some embodiments, the cancer is bone cancer, colon cancer, multiple myeloma, gastric cancer, colorectal cancer, prostate cancer, cervical cancer, lung cancer, pancreatic cancer, medulloblastoma, liver cancer, parathyroid cancer, endometrial cancer, or breast cancer. In some embodiments, the cancer is bone cancer. In some embodiments, the cancer is a cancer that is characterized by secondary low bone mass, including but not limited to, breast cancer and prostate cancer. In some embodiments, the cancer is a cancer that has metastasized to bone.

VII. Formulation and Administration

In some embodiments, the present invention provides a pharmaceutical composition including a compound as described herein (e.g., a compound or composition of Formula I, Formula IA, Formula IB, Formula IC, Formula II, or Formula III as described in Section III above) and a pharmaceutically acceptable excipient. In other embodiments, the composition further comprises an osteoconductive matrix.

The compositions of the present invention can be in the form of a pharmaceutical composition containing the antagonist and a pharmaceutically acceptable carrier. Pharmaceutically acceptable carriers are well known in the art and include aqueous solutions such as physiologically buffered saline or other buffers or solvents or vehicles such as glycols, glycerol, oils such as olive oil or injectable organic esters. The selection of a pharmaceutically acceptable carrier will depend, in part, on the chemical nature of the compound.

The compounds of the present invention can be formulated in a variety of different manners known to one of skill in the art. Pharmaceutically acceptable carriers are determined in part by the particular composition being administered, as well as by the particular method used to administer the composition. Accordingly, there are a wide variety of suitable formulations of pharmaceutical compositions of the present invention (see, e.g., Remington's Pharmaceutical Sciences, 20$^{th}$ ed., 2003, supra).

A pharmaceutically acceptable carrier may include physiologically acceptable compounds that act, for example, to stabilize the composition or increase its absorption, or other excipients as desired. Physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration and on its particular physio-chemical characteristics.

Generally, such carriers should be nontoxic to recipients at the dosages and concentrations employed. Ordinarily, the preparation of such compositions entails combining the therapeutic agent with buffers, antioxidants such as ascorbic acid, low molecular weight (less than about 10 residues) polypeptides, proteins, amino acids, carbohydrates including glucose, maltose, sucrose or dextrins, chelating agents such as EDTA, glutathione and other stabilizers and excipients. Neutral buffered saline or saline mixed with nonspecific serum albumin are exemplary appropriate diluents.

The amount of a compound or composition of the present invention (e.g., a compound or composition of Formula I, Formula IA, Formula IB, Formula IC, Formula II, or Formula III as described herein) that is administered to an individual will depend, in part, on the disease and/or extent of injury. Methods for determining an effective amount of an agent to administer for a diagnostic or a therapeutic procedure are well known in the art and include phase I, phase II and phase III clinical trials, or the Pilot and Pivotal trials (FDA device approval pathway). Generally, an agent is administered in a dose of about 0.01 to 200 mg/kg body weight when administered systemically, and at a concentration of approximately 0.1-100 µM when administered directly to a wound site.

The total amount of the compound or composition can be administered to a subject as a single dose, either as a bolus or by infusion over a relatively short period of time, or can be administered using a fractionated treatment protocol, in which the multiple doses are administered over a more prolonged period of time. One skilled in the art would know that the concentration of a particular compound or composition that is needed to provide an effective amount to a region or regions of injury depends on many factors, including the age and general health of the subject as well as the route of administration, the number of treatments to be administered, and the nature of the compound. In view of these factors, the skilled artisan would adjust the particular dose so as to obtain an effective amount for efficaciously promoting bone formation for therapeutic purposes.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents. Preferred pharmaceutical preparations can deliver the compounds of the invention in a sustained release formulation.

In some embodiments, the methods of the present invention include application of the compounds as described herein in cocktails including other medicaments, for example, antibiotics, fungicides, and anti-inflammatory agents. Alternatively, the methods may comprise sequential dosing of an afflicted individual with a compound as described herein and one or more additional medicaments to optimize a treatment regime. In such optimized regimes, the medicaments, including the granulation inhibitor can be applied in any sequence and in any combination.

Individuals to be treated with the compounds and compositions of the present invention can be any mammal, for example, a human or a non-human mammal, e.g., a primate, dog, cat, horse, cow, goat, sheep, pig, mouse, or rat, or any commercially important animal or domesticated animal.

In some embodiments, an individual to be treated according to the methods of the present invention is an individual who has received or is receiving an anti-resorptive therapeutic agent. For example, in some embodiments, anti-resorptive therapy may be administered concurrently with a compound or composition of the present invention. In some embodiments, anti-resorptive therapy and therapy with a compound or composition of the present invention are administered sequentially (either anti-resorptive therapy preceding therapy with a compound or composition of the present invention, or therapy with a compound or composition of the present invention preceding anti-resorptive therapy). In some embodiments, the individual may have been previously treated with an anti-resorptive agent. In some embodiments, an individual may be concurrently treated with an anti-resorptive agent during a first portion of the treatment course for the compound or composition of the present invention but may discontinue treatment with the anti-resorptive agent during a second portion of the treatment course. In some embodiments, an individual to be treated according to the methods of the present invention has not been treated with an anti-resorptive agent. In some embodiments, an individual is treated with an anti-resorptive agent after being treated with a compound or composition of the present invention.

In some embodiments, the compounds and compositions of the present invention are administered systemically. In some embodiments, the compounds and compositions of the present invention are administered locally.

A. Systemic Delivery

In some embodiments, the compounds and compositions of the present invention are administered systemically. Systemic administration of the compounds and compositions of the present invention can be used, for example, for the treatment of a disease or condition characterized by low bone mass, e.g., osteoporosis.

The pharmaceutical compositions of the present invention can be prepared for administration by a variety of different routes. In general, the type of carrier is selected based on the mode of administration. Pharmaceutical compositions can be formulated for any appropriate manner of administration, including, for example, topical, oral, nasal, intrathecal, rectal, vaginal, sublingual or parenteral administration, including subcutaneous, intravenous, intramuscular, intrasternal, intracavernous, intrameatal, or intraurethral injection or infusion. A pharmaceutical composition (e.g., for oral administration or delivery by injection) can be in the form of a liquid (e.g., an elixir, syrup, solution, emulsion or suspension). A liquid pharmaceutical composition may include, for example, one or more of the following: sterile diluents such as water for injection, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers such as acetates, citrates or phosphates and agents for the adjustment of tonicity such as sodium chloride or dextrose. A parenteral preparation can be enclosed in ampoules, disposable syringes or multiple dose vials made of glass or plastic. The use of physiological saline is preferred, and an injectable pharmaceutical composition is preferably sterile.

The formulations of the invention are also suitable for administration in all body spaces/cavities, including but not limited to pleura, peritoneum, cranium, mediastinum, pericardium, bursae or bursal, epidural, intrathecal, intraocular, intra-articular, intra-discal, intra-medullary, perispinal, etc.

Formulations suitable for oral administration can consist of (a) liquid solutions, such as an effective amount of a compound of the present invention suspended in diluents, such as water, saline or PEG 400; (b) capsules, sachets, depots or tablets, each containing a predetermined amount of the active ingredient, as liquids, solids, granules or gelatin; (c) suspensions in an appropriate liquid; (d) suitable emulsions; and (e) patches. The pharmaceutical forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compounds of the present invention may also be included in slow release formulations for prolonged treatment following a single dose. In one embodiment, the formulation is prepared in the form of microspheres. The microspheres can be prepared as a homogenous matrix of a compound with a biodegradable controlled release material, with optional additional medicaments as the treatment requires. The microspheres are preferably prepared in sizes suitable for infiltration and/or injection, and injected systemically, or directly at the site of treatment.

Some slow release embodiments include polymeric substances that are biodegradable and/or dissolve slowly. Such polymeric substances include polyvinylpyrrolidone, low- and medium-molecular-weight hydroxypropyl cellulose and hydroxypropyl methylcellulose, cross-linked sodium carboxymethylcellulose, carboxymethyl starch, potassium methacrylatedivinylbenzene copolymer, polyvinyl alcohols, starches, starch derivatives, microcrystalline cellulose, ethylcellulose, methylcellulose, and cellulose derivatives, β-cyclodextrin, poly(methyl vinyl ethers/maleic anhydride), glucans, scierozlucans, mannans, xanthans, alzinic acid and derivatives thereof, dextrin derivatives, glyceryl monostearate, semisynthetic glycerides, glyceryl palmitostearate, glyceryl behenate, polyvinylpyrrolidone, gelatine, agnesium stearate, stearic acid, sodium stearate, talc, sodium benzoate, boric acid, and colloidal silica.

Slow release agents of the invention may also include adjuvants such as starch, pregelled starch, calcium phosphate mannitol, lactose, saccharose, glucose, sorbitol, microcrystalline cellulose, gelatin, polyvinylpyrrolidone, methylcellulose, starch solution, ethylcellulose, arabic gum, tragacanth gum, magnesium stearate, stearic acid, colloidal silica, glyceryl monostearate, hydrogenated castor oil, waxes, and mono-, bi-, and trisubstituted glycerides. Slow release agents may also be prepared as generally described in WO94/06416.

B. Local Delivery

In some embodiments, the compounds and compositions of the present invention are administered locally. Local administration of the compounds and compositions of the present invention can be used, for example, for fracture healing, fusion (arthrodesis), orthopedic reconstruction, and periodontal repair. In some embodiments, local administration comprises administering a compound or composition in conjunction with a suitable carrier material capable of maintaining the compound at an in vivo site of application or capable of providing structural load. In some embodiments, the carrier is biocompatible, a matrix, in vivo biodegradable or resorbable, and/or porous enough to allow cell infiltration. In some embodiments, a compound or composition of the present invention (e.g., a compound or composition of Formula I, Formula IA, Formula IB, Formula IC, Formula II, or Formula III) is administered locally via an implantable medical device.

The compounds and compositions of the present invention are useful in clinical applications in conjunction with a suitable delivery or support system (e.g., a scaffold or matrix as described herein). As disclosed herein, the matrix can be combined with a compound or composition of Formula I, Formula IA, Formula IB, Formula IC, Formula II, or Formula III to induce bone formation reliably and reproducibly in a mammalian body. The matrix preferably includes particles of porous materials. The pores are preferred to be of a dimension to permit progenitor cell migration into the matrix and subsequent differentiation and proliferation. In some embodiments, the pore size of the matrix is at least 5 μm, e.g., at least 5, 10, 20, 30, 40, 50, 60, 70, 80, 90, 100, 125, 150, 175, 200, 250, 300, 400, 450, 500, 550, 600, 650, 700, 750, 800, 850, 900, 950, or 1000 μm. The matrix can be fabricated by close packing particulate material into a shape spanning the bone defect, or by otherwise structuring as desired a material that is biocompatible, and preferably biodegradable or resorbable in vivo to serve as a "temporary scaffold" and substratum for recruitment of migratory progenitor cells, and as a base for their subsequent anchoring and proliferation. In some embodiments, the scaffold or matrix comprises a mesh structure, a foam structure, a sponge structure, or a fiber structure.

A scaffold or matrix for use in delivering a compound of the present invention can comprise a synthetic and/or biologic material. In some embodiments, the scaffold or matrix comprises a naturally occurring polymer, a synthetic biodegradable polymer, a synthetic nonbiodegradable polymer, a bioceramic, a bioglass, or combinations thereof. Natural and synthetic polymers, bioceramics, and bioglasses for use in scaffolds are known in the art. See, e.g., Dhandayuthapani et al., International Journal of Polymer Science, volume 2011, article ID 290602 (2011), incorporated by reference herein. Natural polymers include, but are not limited to, proteins (e.g., silk, collagen, gelatin, fibrinogen, elastin, keratin, actin, and myosin), polysaccharides (e.g., cellulose, amylose, dextran, chitin, chitosan, and glycosaminoglycans), and polynucleotides (e.g., DNA and RNA). Synthetic polymers include, but are not limited to, PLA, PGA, PLLA, PLGA, PCL, PLDLA, PDS, PGCL, PEA, PCA, PDLLA, PEU, and PBT. Bioceramics and bioglasses include, but are not limited to, HAP, TCP, CP ceramics, BCP, and TCP. In some embodiments, the scaffold or matrix is a hydrogel scaffold, a fibrous scaffold, a microsphere scaffold, a polymer-bioceramic composite scaffold, or an acellular scaffold.

In some embodiments, the scaffold or matrix is an osteoconductive matrix. Non-limiting examples of suitable osteoconductive matrix materials include, for example, collagen; homopolymers or copolymers of glycolic acid, lactic acid, and butyric acid, including derivatives thereof; and ceramics, hydroxyapatite, tricalcium phosphate and other calcium phosphates, and calcium sulphates. Other matrices useful in the present invention include, but are not limited to, Kryptonite bone cement (Doctors Research Group, Oxford, Conn.) and Genex bone graft (Biocomposites, Wilmington, N.C.). Combinations of these matrix materials also can be useful. The osteoconductive matrix can also include a structural support such as a calcium salt, calcium sulfate, calcium phosphate, a calcium phosphate cement, hydroxyapatite, coralline based hydroyxapatite (HA), dicalcium phosphate, tricalcium phosphate (TCP), calcium carbonate, collagen, plaster of Paris, phosphophoryn, a borosilicate, a biocompatible ceramic, a calcium phosphate ceramic, polytetrafluoroethylene, sulfate salt, or hydrogel.

In some embodiments, the osteoconductive matrix comprises an osteoinductive agent and, optionally, a structural support. The osteoinductive agent can be any agent that promotes bone formation. In some embodiments, the osteoinductive agent is bone allograft, bone autograft, demineralized bone, or periodontal ligament cells.

C. Combination Therapy

In practicing the methods of the present invention, the pharmaceutical compositions can be used alone, or in combination with other therapeutic or diagnostic agents. The additional drugs used in the combination protocols of the present invention can be administered separately or one or more of the drugs used in the combination protocols can be administered together, such as in an admixture. Where one or more drugs are administered separately, the timing and schedule of administration of each drug can vary. The other therapeutic or diagnostic agents can be administered at the same time as the compounds of the present invention, separately or at different times.

In some embodiments, a compound or composition as described herein (e.g., a compound or composition of Formula I, Formula IA, Formula IB, Formula IC, Formula II, or Formula III) is administered in combination with one or more other therapeutic agents. When a compound of the present invention and is combined with another agent, the two can be co-administered or administered separately. Co-administration includes administering the other agent within 0.5, 1, 2, 4, 6, 8, 10, 12, 16, 20, or 24 hours, as well as within 1 to 7 days (e.g., 1, 2, 3, 4, 5, 6, or, 7 days), 1 to 4 weeks (e.g., 1, 2, 3, or 4 weeks), or 1 or 6 months (e.g., 1, 2, 3, 4, 5, or 6 months) of administering the compound of the present invention. Co-administration also includes administering the other agent and the compound of the present invention simultaneously, approximately simultaneously (e.g., within about 1, 5, 10, 15, 20, or 30 minutes, or on the same day, of each other), or sequentially in any order. In some embodiments, co-administration comprises administering another agent (e.g., an antiresorptive) for a period of time (e.g., weeks, months, or years), then administering a compound or composition of Formula I, Formula IA, Formula IB, Formula IC, Formula II, or Formula III for a period of time (e.g., days, weeks, months, or years), then administering the other agent (e.g., antiresorptive) either alone or in combination with the compound or composition of Formula I, Formula IA, Formula IB, Formula IC, Formula II, or Formula III. In some embodiments, the other agent and the compound of the present invention can each be administered once a day, or two, three, or more times per day so as to provide the preferred dosage level per day.

In some embodiments, co-administration can be accomplished by co-formulation, i.e., preparing a single pharmaceutical composition including both a compound of the present invention and the second therapeutic agent (e.g., the antiresorptive agent). In other embodiments, the compound of the present invention and the second therapeutic agent are formulated separately.

The one or more other therapeutic agents can be delivered by any suitable means. The pharmaceutical preparation is preferably in unit dosage form. In such form the preparation is subdivided into unit doses containing appropriate quantities of the antiresorptive agent and/or the compound of the present invention. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The one or more other therapeutic agents can be present in any suitable amount, and can depend on various factors including, but not limited to, weight and age of the subject, state of the disease, etc. Suitable dosage ranges for the one or more other therapeutic agents in combination with the a compound or composition of the present invention include from about 0.1 ug to about 10,000 mg, or about 0.1 ug to about 1000 mg, or about 0.1 ug to about 500 mg, or about 0.1 ug to about 1000 ug, or about 1 ug to about 1000 mg, or about 1 ug to about 500 mg, or about 1 ug to about 50 mg, or about 1 ug to about 1000 ug, or about 10 ug to about 1000 mg, or about 10 ug to about 500 mg, or about 10 ug to about 50 mg, or about 0.1 mg to about 10,000 mg, or about 1 mg to about 1000 mg, or about 10 mg to about 750 mg, or about 25 mg to about 500 mg, or about 50 mg to about 250 mg. Suitable dosages for the one or more other therapeutic agents in combination with a compound or composition of the present invention, include about 1, 5, 10, 20, 30, 40, 50, 60, 70, 80, 90, 100, 200, 300, 400, 500, 600, 700, 800, 900 or 1000 mg.

The one or more other therapeutic agents and the compound or composition of the present invention can be present in the compositions of the present invention in any suitable weight ratio, such as from about 1:100 to about 100:1 (w/w), or about 1:50 to about 50:1, or about 1:25 to about 25:1, or about 1:10 to about 10:1, or about 1:5 to about 5:1 (w/w). Other dosages and dosage ratios of the antiresorptive agent and the compound of the present invention are suitable in the compositions and methods of the present invention.

The composition can also contain other compatible therapeutic agents. The compounds described herein can be used in combination with one another, with other active agents, or with adjunctive agents that may not be effective alone, but may contribute to the efficacy of the active agent.

In some embodiments, an individual to be treated according to a method of the present invention is administered a compound or composition as described herein (e.g., a compound or composition of Formula I, Formula IA, Formula IB, Formula IC, Formula II, or Formula III) in combination or sequentially with an antiresorptive drug. Antiresorptive drugs include those that slow or block the resorption of bone. Administration of a compound or composition as described herein and an antiresorptive drug can promote local bone growth and/or systemic bone growth. In some embodiments, the administration of a compound or composition as described herein and an antiresorptive drug promotes systemic bone growth. Bone growth can be achieved by increasing bone mineral content, increasing bone density and/or growth of new bone. In other embodiments, local application of the compound or composition as described herein and an antiresorptive drug achieves systemic bone growth.

Antiresorptive drugs useful in the methods of the present invention include, but are not limited to, denosumab, a RankL inhibitor, a bisphosphonate (e.g., Fosamax, Actonel, or Reclast), a selective estrogen receptor modulator (SERM) or analog (e.g., Evista), calcitonin, a calcitonin analog (e.g., Miacalcic), Vitamin D or a Vitamin D analog, CatK inhibitor, prostaglandin inhibitor, or phosphodiesterase inhibitor type E.

In some embodiments, the antiresorptive drug is denosumab.

Bisphosphonates useful in the methods of the present invention can be any suitable bisphosphonate. In some embodiments, the bisphosphonates are nitrogenous, such as Pamidronate (APD, Aredia), Neridronate, Olpadronate, Alendronate (Fosamax), Ibandronate (Boniva), Risedronate (Actonel) and Zoledronate (Zometa). In other embodiments, the bisphosphonates are non-nitrogenous, such as Etidronate (Didronel), Clodronate (Bonefos, Loron) and Tiludronate (Skelid). One of skill in the art will appreciate that other bisphosphonates are useful in the present invention.

SERMs useful in the methods of the present invention can be any suitable SERM. In some embodiments, the SERM can be clomifene, raloxifene, tamoxifen, toremifene, bazedoxifene, lasofoxifene or ormeloxifene. One of skill in the art will appreciate that other SERMs are useful in the present invention.

The antiresorptive drug can also be any suitable calcitonin analog or cathepsin K inhibitor. In some embodiments, calcitonin analogs useful in the methods of the present invention include, but are not limited to, miacalcic. One of skill in the art will appreciate that other calcitonin analogs are useful in the present invention.

Vitamin D analogs useful in the methods of the present invention can be any suitable Vitamin D analog. In some embodiments, Vitamin D analogs useful in the methods of the present invention include, but are not limited to, Vitamin D1 (molecular compound of ergocalciferol with lumisterol, 1:1), Vitamin D2 (ergocalciferol or calciferol), Vitamin D3 (cholecalciferol), Vitamin D4 (22-dihydroergocalciferol) and Vitamin D5 (sitocalciferol). One of skill in the art will appreciate that other Vitamin D analogs are useful in the present invention.

RankL inhibitors useful in the present invention include any compounds that inhibit the activity of RankL. For example, RankL inhibitors include, but are not limited to, the human monoclonal antibody denosumab. One of skill in the art will appreciate that other RankL inhibitors are useful in the present invention.

In some embodiments, an individual to be treated according to a method of the present invention is administered a compound or composition as described herein (e.g., a compound or composition of Formula I, Formula IA, Formula IB, Formula IC, Formula II, or Formula III) in combination or sequentially with an anabolic agent. In some embodiments, the anabolic agent is parathyroid hormone (PTH) or an analog thereof (e.g., teriparatide (Forteo). In some embodiments, the anabolic agent is a sclerostin antibody (Mab) inhibitor or a compound of Formula I, Formula IA, Formula IB, Formula IC, Formula II, or Formula III.

VIII. Medical Devices

In some embodiments, the present invention provides a medical device formed from a structural support, wherein an implantable portion of the structural support is adapted to be permanently implanted within a subject, wherein the implantable portion is attached to a bone, the structural support bearing at least a partial coating including a compound of Formula I, Formula IA, Formula IB, Formula IC, Formula II, or Formula III as described herein (e.g., in Section III above). In some embodiments, the medical device is an orthopedic or periodontal medical device.

Other aspects of the present invention are directed towards medical implants. Such medical devices and implants include, for example, the osteogenic devices and methods of using the same for repairing endochondral bone and osteochondral defects taught in US patent application publication No. 20060177475 to David Rueger et al., published Aug. 10, 2006, as well as in issued U.S. Pat. Nos. 6,190,880, 5,344,654, 5,324,819, 5,468,845, 6,949,251, 6,426,332 and 5,656,593, and U.S. Publication Nos. 2002/0169122, 2002/0187104, 2006/0252724 and 2007/0172479, the subject matter of which is hereby incorporated by reference.

These medical devices generally provide a structural support having an implantable portion preferentially adapted to mechanically engage bone and/or cartilage as taught, for instance, in U.S. Publication No. 2006/0178752 to Joseph Vaccarino III, et al., published Aug. 10, 2006, the subject matter of which is hereby incorporated by reference. These bone implants desirably comprise an active agent on at least a portion thereof. As shown by U.S. Publication No. 2006/0188542 to John Dennis Bobyn, et al., published Aug. 24, 2006, the subject matter of which is hereby incorporated by reference, the active agent is preferably formulated to be locally deliverable to bone proximate the implant in sustained-release or in at least a two-phased release scheme. In the latter, a first phase rapidly releases a first quantity of the active agent, and the second and subsequent phases gradually release a second quantity of the active agent, whereby bone formation stimulated by the active agent is modulated.

Medical devices such as bone implants feature implantable portions bearing a compound or composition of present invention (e.g., a compound or composition of Formula I, Formula IA, Formula IB, Formula IC, Formula II, or Formula III) foster quicker and more complete bone formation in situ. The implantable portion of the medical device can be desirable at least partially or totally covered or impregnated with a compound or composition of the present invention. In some embodiments, the medical device is externally coated with a compound or composition as described herein. In some embodiments, the external coating completely coats the implantable portion of the structural support. In some embodiments, the structural support (e.g., matrix or scaffold) comprises a compound or composition as described herein within the support, i.e., internally. In some embodiments, the structural support (e.g., matrix or scaffold) comprises an external coating of a compound or composition as described herein and also comprises the compound or composition within the support, i.e., internally.

In some other embodiments, the implantable portion of the structural support comprises an osteoconductive matrix. The matrix material can be conducive to bone growth. This can be desirable for materials such as teeth and artificial bone graft sections, and the like. Alternatively, when the implantable sections are load bearing and formed, e.g., of stainless steel, these implantable sections can be desirable when formed with a coating of a compound or composition of the present invention. In that event, it is desirable to also provide a separate matrix material conducive to forming new bone growth.

In some embodiments, the matrix comprises particles of porous materials. The pores are preferred to be of a dimension to permit progenitor cell migration into the matrix and subsequent differentiation and proliferation. In some embodiments, the pore size of the matrix is at least 5 µm, e.g., at least 5, 10, 20, 30, 40, 50, 60, 70, 80, 90, 100, 125, 150, 175, 200, 250, 300, 400, 450, 500, 550, 600, 650, 700, 750, 800, 850, 900, 950, or 1000 µm. In some embodiments, the scaffold or matrix comprises a mesh structure, a foam structure, a sponge structure, or a fiber structure.

A scaffold or matrix for use in a device as described herein can comprise a synthetic and/or biologic material. In some embodiments, the scaffold or matrix comprises a naturally occurring polymer, a synthetic biodegradable polymer, a synthetic nonbiodegradable polymer, a bioceramic, a bioglass, or combinations thereof. Natural and synthetic polymers, bioceramics, and bioglasses for use in scaffolds are known in the art. See, e.g., Dhandayuthapani et al., International Journal of Polymer Science, volume 2011, article ID 290602 (2011), incorporated by reference herein. Natural polymers include, but are not limited to, proteins (e.g., silk, collagen, gelatin, fibrinogen, elastin, keratin, actin, and myosin), polysaccharides (e.g., cellulose, amylose, dextran, chitin, chitosan, and glycosaminoglycans), and polynucleotides (e.g., DNA and RNA). Synthetic polymers include, but are not limited to, PLA, PGA, PLLA, PLGA, PCL, PLDLA, PDS, PGCL, PEA, PCA, PDLLA, PEU, and PBT. Bioceramics and bioglasses include, but are not limited to, HAP, TCP, CP ceramics, BCP, and TCP. In some embodiments, the scaffold or matrix is a hydrogel scaffold, a fibrous scaffold, a microsphere scaffold, a polymer-bioceramic composite scaffold, or an acellular scaffold.

In some embodiments, suitable matrixes include those comprising composite biomaterials having a sponge-like structure such as those containing, e.g., phosphophoryn and/or collagen as taught in Takashi Saito's U.S. Publication No. 2006/0188544, published Aug. 24, 2006, the subject matter of which is hereby incorporated by reference. Such coatings include, for example, the single and multilayer coatings taught in U.S. Publication No. 2006/0204542 to Zongtao Zhang et al, published Sep. 14, 2006, as well as those in U.S. Pat. Nos. 6,949,251, 5,298,852, 5,939,039, and 7,189,263 and can be made by conventional methods including the methods taught therein, the subject matter of which is hereby incorporated by reference.

In some embodiments, the matrix is an osteoconductive matrix. In some embodiments, the osteoconductive matrix includes an osteoinductive agent such as bone allograft, bone autograft, demineralized bone or periodontal ligament cells. In some other embodiments, the osteoconductive matrix can be a calcium salt, calcium sulfate, calcium phosphate, a calcium phosphate cement, hydroxyapatite, coralline based hydroyxapatite (HA), dicalcium phosphate, tricalcium phosphate (TCP), calcium carbonate, collagen, plaster of Paris, phosphophoryn, a borosilicate, a biocompatible ceramic, a calcium phosphate ceramic, polytetrafluoroethylene, sulfate salt, borosilicate or hydrogel. One of skill in the art will appreciate that other osteoconductive matrices and osteoinductive agents are useful in the present invention.

IX. Assay for Identification of Compounds for Treating Bone Loss

Compounds useful in the methods of the present invention can be identified via a variety of methods known to one of skill in the art. Several exemplary methods for identifying such antagonists are described herein, including cell-based and in vitro techniques (Journal of Bone and Mineral Research 2006, 21(11), 1738-1749). A general method of identifying compounds involves evaluating the effects of antagonist candidates on bone formation under controlled conditions. Preferably bone formation is determined using micro-CT techniques on live animals. Preferred animals include rodents, more preferred are primates. Femur, tibia and vertebrae bones are particularly useful subjects for such study.

Briefly, the test animal is treated with a predetermined dose of a candidate compound. A control animal is treated with a control solution, preferably a non-irritating buffer solution or other carrier. When the candidate compound is delivered in a carrier, the control solution is ideally the carrier absent the candidate compound. Multiple doses of the candidate compound can be applied to the test animal, preferably following a predetermined schedule of dosing. The dosing schedule can be over a period of days, e.g., 1, 2, 3, 4, 5, 6, 7, 8, 9, 10, 15, 20, 25 days or more; over a period of weeks, e.g., 1, 2, 3, 4, 5, 6, 7, 8, 9, 10 weeks or more; or other a period of months, e.g., 1, 2, 3, 4, 5, 6, 7, 8, 9, 10 months or more.

In an exemplary embodiment, localized administration in situ of a candidate compound can be made into a test animal, with a control animal receiving an equal volume of control solution without the candidate compound. Suitable dosage will depend on the nature of the particular candidate compound being tested. By way of example, in dosing it should be noted that systemic administration (e.g., by oral or injection, e.g., intravenously, subcutaneously or intramuscularly), can also be used. Dosing performed by nebulized inhalation, eye drops, or oral ingestion should be at an amount sufficient to produce blood levels of the candidate compound similar to those reached using systemic injection. The amount of candidate compound that can be delivered by nebulized inhalation, eye drops, or oral ingestion to attain these levels is dependent upon the nature of the inhibitor used and can be determined by routine experimentation.

Once the dosing schedule has been completed, both test and control animals are examined to determine the quantity of bone formation present. This can be accomplished by any suitable method, but is preferably performed on live animals to analyze the bone mineral content. Methods for micro-CT examination of bones in animals are well known in the art. A candidate compound suitable for use in promoting bone formation is identified by noting a significant increase in bone formation in the test animal when compared to the control animal. In some embodiments, a candidate compound is identified as suitable for use in promoting bone formation if the amount of bone formation in the test bone(s) of the test animal is at least 0.5%, 1, 5, 10, 20, 30, 40, 50, 60, 70, 80, 90, 100, 200, 300, 400, 500, 600, 700, 800, 900 or 1000% or more as compared to the comparable bone(s) of the control animal. In some embodiments, bone formation is increased by at least 10%, at least 20%, at least 30%, at least 40%, at least 50% or more as compared to the control animal. Where necessary, levels of bone formation can be calculated by determining the volume of bone formation present in each animal. Calculations can be performed by constructing a 3-dimensional image of the bone formation and calculating the volume from the image with the aid of e.g., histomorphometry.

An example of the molecular modeling system described generally above consists of the CHARMm and QUANTA programs, Polygen Corporation, Waltham, Mass. CHARMm performs the energy minimization and molecular dynamics functions. QUANTA performs the construction, graphic modeling and analysis of molecular structure. QUANTA allows interactive construction, modification, visualization, and analysis of the behavior of molecules with each other.

Compounds may also be identified using a process known as computer, or molecular modeling, which allows visualization of the three-dimensional atomic structure of a selected molecule and the rational design of new compounds that will interact with the molecule. The three-dimensional construct typically depends on data from x-ray crystallographic analyses or NMR imaging of the selected molecule. The molecular dynamics require force field data. The computer graphics systems enable prediction of how a new compound will link to the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user-friendly, menu-driven interfaces between the molecular design program and the user.

X. Examples

Example 1: Synthesis of N,N-dimethyl-1-(9H-pyrido[2,3-b]indol-9-yl)propan-2-amine

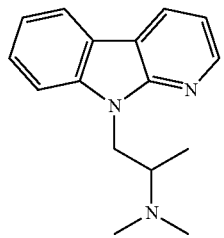 [SMILES: CC(Cn1c2ccccc2c2cccnc21)N(C)C]

2-(dimethylamino)propan-1-ol (Matrix catalog #032457; 1.0 g, 9.7 mmol) was dissolved in 10 mL DMF and 1 mL (14 mmol) of thionyl chloride was added. The reaction mixture was stirred overnight at ambient temperature and monitored by LCMS. After the reaction was completed the solvent was evaporated to dryness to give 1.5 g of crude 1-chloro-N,N-dimethylpropan-2-amine HCl salt that was used further without purification (yield 94%).

A mixture of the alpha-carboline starting material (Toronto Research Chemicals catalog # C176600, 25 mg, 0.1 mmol), anhydrous DMF (3 mL), and anhydrous THF (1 mL) was stirred at ambient temperature until clear. 60% NaH (50 mg portions until evolution of gas ceases) and 1-chloro-N,N-dimethylpropan-2-amine hydrochloride (47 mg, 0.28 mmol) were then added and stirred at ambient temperature for 30 min after which the THF was evaporated under reduced pressure. The resulting solution was poured into $H_2O$ (10 mL), and extracted with petrol ether (15 mL). The water phase was condensed under reduced pressure. The oil obtained was purified by prep HPLC (mobile phase A: 0.1% formic acid in water; mobile phase B: MeCN; solvent gradient: 100-50 A/B over 35 mins then 50-0 A/B over 5 mins then 0/100 A/B 5 mins; flow rate: 45 mL/min; column: Luna RP18, 10 mm, 21×250 mm) to obtain the target product (8 mg, 27% yield). $^1$H NMR (DMSO-$d_6$, 400 MHz) δ 8.53 (dd, 1H, J=1.6, 6.0 Hz), 8.47 (dd, 1H, J=1.6, 4.8 Hz), 8.20 (d, 1H, J=7.6 Hz), 7.66 (d, 1H, J=8.4 Hz), 7.53 (t, 1H), 7.24 (m, 2H), 4.54 (dd, 1H, J=6.8, 21 Hz), 4.33 (dd, 1H, J=6.8, 21 Hz), 3.48 (m, 1H), 2.23 (s, 6H), 0.87 (d, 3H, J=6.4 Hz); LCMS m/z 254.37 ([M+H]$^+$, $C_{16}H_{20}N_3$ requires 254.17).

Example 2: Synthesis of 1-(9H-carbazol-9-yl)-N,N-dimethylpropan-2-amine

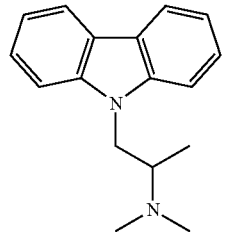 [SMILES: CC(Cn1c2ccccc2c2ccccc21)N(C)C]

2-(dimethylamino)propan-1-ol (Matrix catalog #032457; 1.0 g, 9.7 mmol) was dissolved in 10 mL DMF and 1 mL (14 mmol) of thionyl chloride was added. The reaction mixture was stirred overnight at ambient temperature and monitored by LCMS. After the reaction was completed the solvent was evaporated to dryness to give 1.5 g of crude 1-chloro-N,N-dimethylpropan-2-amine HCl salt that was used further without purification (yield 94%).

A mixture of the carbazole starting material (Aldrich catalog # C5132, 40 mg, 0.23 mmol), anhydrous DMF (3 mL), and anhydrous THF (1 mL) was stirred at ambient temperature until clear. 60% NaH (50 mg portions until evolution of gas ceases) and 1-chloro-N,N-dimethylpropan-2-amine hydrochloride (75 mg, 0.46 mmol) were then added and stirred at ambient temperature for 30 min after which the THF was evaporated under reduced pressure. The resulting solution was poured into $H_2O$ (10 mL), and extracted with petrol ether (15 mL). The water phase was condensed under reduced pressure. The oil obtained was purified by prep HPLC (mobile phase A: 0.1% formic acid in water; mobile phase B: MeCN; solvent gradient: 100-50 A/B over 35 mins then 50-0 A/B over 5 mins then 0/100 A/B 5 mins; flow rate: 45 mL/min; column: Luna RP18, 10 mm, 21×250 mm) to obtain the target product (9 mg, 20% yield). $^1$H NMR (DMSO-$d_6$, 400 MHz) δ 8.14 (d, 2H, J=7.6 Hz), 7.58 (d, 2H, J=8.0 Hz), 7.45 (t, 2H, J=7.2 Hz), 7.20 (t, 2H, J=7.2 Hz), 4.45 (dd, 1H, J=6.0, 14.8 Hz), 4.33 (dd, 1H, J=8.0, 14.6 Hz), 3.15 (m, 1H), 2.27 (s, 6H), 0.85 (d, 3H, J=6.8 Hz).

Example 3: Synthesis of 1-(7-methoxy-1-methyl-9H-pyrido[3,4-b]indol-9-yl)-N,N-dimethylpropan-2-aminium formate

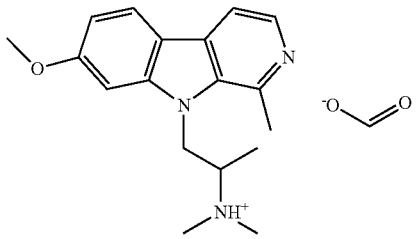

2-(dimethylamino)propan-1-ol (Matrix catalog #032457; 1.0 g, 9.7 mmol) was dissolved in 10 mL DMF and 1 mL (14 mmol) of thionyl chloride was added. The reaction mixture was stirred overnight at ambient temperature and monitored by LCMS. After the reaction was completed the solvent was evaporated to dryness to give 1.5 g of crude 1-chloro-N,N-dimethylpropan-2-amine HCl salt that was used further without purification (yield 94%).

A mixture of the beta-carboline starting material (TCI catalog # H0001, 20 mg, 0.1 mmol), anhydrous DMF (1 mL), and anhydrous THF (1 mL) was stirred at ambient temperature until clear. 60% NaH (10 mg) and 1-chloro-N,N-dimethylpropan-2-amine hydrochloride (30 mg, 0.2 mmol) were then added and stirred at ambient temperature for 30 min after which the THF was evaporated under reduced pressure. The resulting solution was poured into H$_2$O (10 mL), and extracted with ethyl acetate (15 mL). The organic phase was washed with water and brine, then dried over anhydrous sodium sulfate, filtered, and evaporated. The oil obtained was purified by prep HPLC (mobile phase A: 0.1% formic acid in water; mobile phase B: MeCN; solvent gradient: 100-50 A/B over 35 mins then 50-0 A/B over 5 mins then 0/100 A/B 5 mins; flow rate: 45 mL/min; column: Luna RP18, 10 mm, 21×250 mm) to obtain the target product (17 mg, 62% yield). $^1$H NMR (DMSO-d$_6$, 300 MHz) δ 11.86 (bs, 1H), 8.54 (d, 1H, J=6.0 Hz), 8.45 (m, 2H), 7.71 (d, 1H, J=1.8 Hz), 7.11 (dd, 1H, J=1.8, 8.7 Hz), 5.28 (m, 1H), 4.99 (m, 1H), 4.02 (s, 3H), 3.92 (m, 1H), 3.26 (s, 3H), 2.87 (bs, 6H), 0.99 (d, 3H, J=6.6 Hz); LCMS m/z 298.54 ([M+H]$^+$, C$_{18}$H$_{24}$N$_3$O requires 298.19).

The Example 3 beta-carboline starting material (TCI catalog # H0001) can also be converted to compounds of Formula I or Formula II using the procedure described in Example 3 and Scheme 1.

Example 4: Synthesis of 9-(2-(dimethylamino)propyl)-1-methyl-9H-pyrido[3,4-b]indol-7-ol

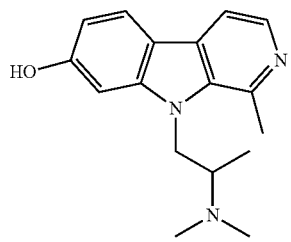 [SMILES: Cc1nccc2c3ccc(O)cc3n(CC(C)N(C)C)c12]

1-(7-methoxy-1-methyl-9H-pyrido[3,4-b]indol-9-yl)-N,N-dimethylpropan-2-aminium formate (150 mg 0.5 mmol) was dissolved in 5 mL of acetic acid and 5 mL of concentrated HBr was carefully added. Solution was refluxed overnight and monitored by LCMS. After the reaction was completed the reaction mixture was evaporated and crude product was purified by RP HPLC (mobile phase A: 0.1% formic acid in water; mobile phase B: MeCN; solvent gradient: 100-50 A/B over 35 mins then 50-0 A/B over 5 mins then 0/100 A/B 5 mins; flow rate: 45 mL/min; column: Luna RP18, 10 mm, 21×250 mm) to obtain the target product (85 mg, yield 61%). $^1$H NMR (DMSO-d$_6$, 400 MHz) δ 8.26 (s, 1H), 8.15 (d, 1H, J=6.0 Hz), 8.01 (d, 1H, J=11 Hz), 7.86 (d, 1H, J=6.4 Hz), 7.01 (s, 1H), 6.78 (d, 1H, J=11.2 Hz), 4.57 (m, 1H), 4.48 (m, 1H), 3.19 (m, 1H), 2.95 (s, 3H), 2.39 (s, 6H), 0.78 (d, 3H, J=8.8 Hz); LCMS m/z 284.37 ([M+H]$^+$, C$_{17}$H$_{22}$N$_3$O requires 284.18).

The Example 3 beta-carboline starting material (TCI catalog # H0001) can also be converted to compounds of Formula I or Formula II using the procedure described in Example 3 and Example 4 and Scheme 1.

Example 5: 2-(7-methoxy-1-methyl-9H-pyrido[3,4-b]indol-9-yl)-N,N-dimethylpropan-1-amine

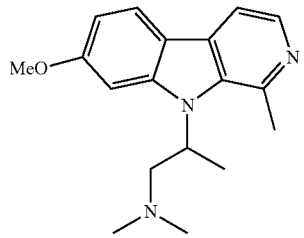 [SMILES: COc1ccc2c3ccnc(C)c3n(C(C)CN(C)C)c2c1]

$^1$H NMR (DMSO-d$_6$, 400 MHz) δ 8.16 (d, 1H, J=5.2 Hz), 8.12 (d, 1H, J=8.8 Hz), 7.87 (d, 1H, J=5.2 Hz), 7.11 (d, 1H, J=2.4 Hz), 6.88 (dd, 1H, J=8.8, 2.0 Hz), 5.35 (m, 1H), 3.89 (s, 3H), 3.01 (dd, 1H, J=12.5, 8.0 Hz), 2.97 (s, 3H), 2.83 (dd, 1H, J=12.8, 6.4 Hz), 2.07 (s, 6H), 1.64 (d, 1H, J=6.8 Hz); LCMS m/z 298.19 ([M+H]$^+$, C$_{18}$H$_{24}$N$_3$O requires 298.19).

Example 6: N,N-diethyl-3-(7-methoxy-1-methyl-9H-pyrido[3,4-b]indol-9-yl)propan-1-amine

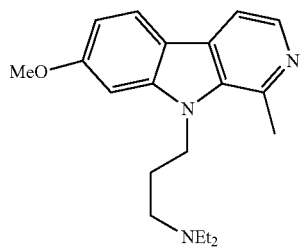

$^1$H NMR (DMSO-d$_6$, 400 MHz) δ 8.15 (d, 1H, J=5.2 Hz), 8.07 (d, 1H, J=8.8 Hz), 7.85 (d, 1H, J=5.2 Hz), 7.15 (d, 1H, J=2.0 Hz), 6.87 (dd, 1H, J=8.4, 2.0 Hz), 4.55 (m, 2H), 3.89 (s, 3H), 2.95 (s, 3H), 2.42 (m, 6H), 1.79 (m, 2H), 0.92 (t, 6H, J=6.8 Hz); LCMS m/z 326.22 ([M+H]$^+$, C$_{20}$H$_{28}$N$_3$O requires 326.22).

Example 7: 2-(7-methoxy-1-methyl-9H-pyrido[3,4-b]indol-9-yl)-N,N-dimethyl ethanamine

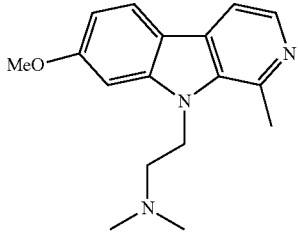 [SMILES: COc1ccc2c3ccnc(C)c3n(CCN(C)C)c2c1]

$^1$H NMR (DMSO-d$_6$, 400 MHz) δ 8.16 (d, 1H, J=5.2 Hz), 8.08 (d, 1H, J=8.4 Hz), 7.86 (d, 1H, J=5.2 Hz), 7.12 (d, 1H, J=2.0 Hz), 6.87 (dd, 1H, J=8.4, 2.0 Hz), 4.64 (t, 2H, J=7.2 Hz), 3.90 (s, 3H), 2.95 (s, 3H), 2.57 (t, 2H, J=7.2 Hz), 2.23 (s, 6H).

Example 8: 4-(1-(7-methoxy-1-methyl-9H-pyrido[3,4-b]indol-9-yl)propan-2-yl) morpholine

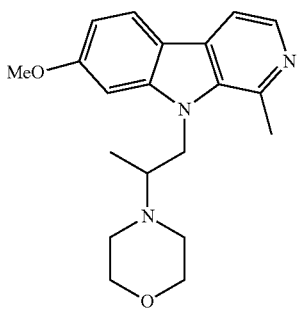 [SMILES: COc1ccc2c3ccnc(C)c3n(CC(C)N3CCOCC3)c2c1]

$^1$H NMR (DMSO-d$_6$, 400 MHz) δ 8.18 (d, 1H, J=5.2 Hz), 8.08 (d, 1H, J=8.8 Hz), 7.87 (d, 1H, J=5.2 Hz), 7.19 (d, 1H, J=2.0 Hz), 6.86 (dd, 1H, J=8.4, 2.0 Hz), 4.61 (dd, 1H, J=15.2, 6.4 Hz), 4.47 (dd, 1H, J=15.2, 6.4 Hz), 3.89 (s, 3H), 3.39 (m, 4H), 2.97 (m, 1H), 2.93 (s, 3H), 2.65 (m, 2H), 2.31 (m, 2H), 0.82 (d, 3H, J=6.4 Hz).

Example 9: 7-methoxy-1-methyl-9-(2-(piperidin-1-yl)propyl)-9H-pyrido[3,4-b]indole

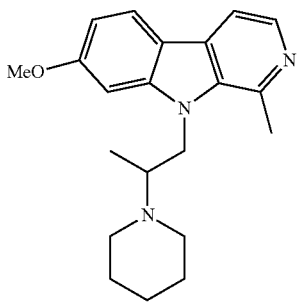 [SMILES: COc1ccc2c3ccnc(C)c3n(CC(C)N3CCCCC3)c2c1]

$^1$H NMR (DMSO-d$_6$, 400 MHz) δ 8.17 (d, 1H, J=5.2 Hz), 8.06 (d, 1H, J=8.4 Hz), 7.86 (d, 1H, J=5.2 Hz), 7.17 (d, 1H, J=2.0 Hz), 6.84 (dd, 1H, J=8.4, 2.0 Hz), 4.56 (dd, 1H, J=14.8, 6.4 Hz), 4.46 (dd, 1H, J=14.8, 6.4 Hz), 3.89 (s, 3H), 2.97 (m, 1H), 2.92 (s, 3H), 2.61 (m, 2H), 2.25 (m, 2H), 1.32 (m, 6H), 0.80 (d, 3H, J=6.8 Hz).

Example 10: 7-methoxy-1-methyl-9-(2-(piperidin-1-yl)ethyl)-9H-pyrido[3,4-b]indole

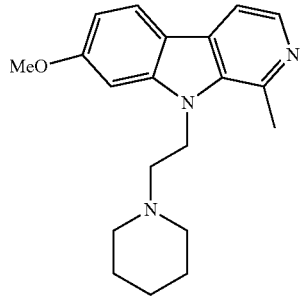 [SMILES: COc1ccc2c3ccnc(C)c3n(CCN3CCCCC3)c2c1]

$^1$H NMR (DMSO-d$_6$, 400 MHz) δ 8.16 (d, 1H, J=5.2 Hz), 8.08 (d, 1H, J=8.4 Hz), 7.86 (d, 1H, J=5.2 Hz), 7.14 (d, 1H, J=2.4 Hz), 6.86 (dd, 1H, J=8.8, 2.4 Hz), 4.65 (t, 2H, J=7.2 Hz), 3.90 (s, 3H), 2.97 (s, 3H), 2.62 (t, 2H, J=7.2 Hz), 2.40 (m, 4H), 1.45 (m, 4H), 1.35 (m, 2H).

Example 11: 4-(3-(7-methoxy-1-methyl-9H-pyrido[3,4-b]indol-9-yl)propyl)morpholine formate

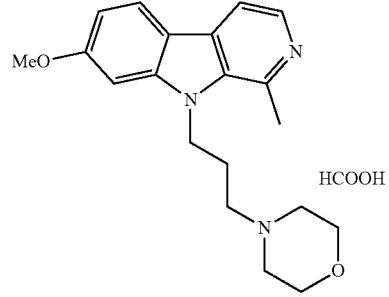 [SMILES: COc1ccc2c3ccnc(C)c3n(CCCN3CCOCC3)c2c1 ; "HCOOH"]

$^1$H NMR (DMSO-d$_6$, 400 MHz) δ 8.17 (d, 1H, J=5.2 Hz), 8.15 (formate), 8.10 (d, 1H, J=8.4 Hz), 7.89 (d, 1H, J=5.6 Hz), 7.18 (d, 1H, J=2.4 Hz), 6.88 (dd, 1H, J=8.8, 2.4 Hz), 4.62 (t, 1H, J=7.6 Hz), 3.90 (s, 3H), 3.53 (t, 1H, J=4.8 Hz), 2.97 (s, 3H), 2.31 (m, 6H), 1.89 (m, 2H).

Example 12: 4-(2-(7-methoxy-1-methyl-9H-pyrido[3,4-b]indol-9-yl)ethyl)morpholine

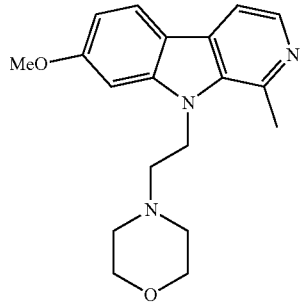 [SMILES: COc1ccc2c3ccnc(C)c3n(CCN3CCOCC3)c2c1]

¹H NMR (DMSO-d₆, 400 MHz) δ 8.16 (d, 1H, J=5.2 Hz), 8.08 (d, 1H, J=8.8 Hz), 7.87 (d, 1H, J=5.2 Hz), 7.15 (d, 1H, J=2.4 Hz), 6.87 (dd, 1H, J=8.8, 2.4 Hz), 4.67 (t, 2H, J=7.2 Hz), 3.90 (s, 3H), 3.52 (t, 4H, J=4.8 Hz), 2.97 (s, 3H), 2.65 (m, 2H), 2.44 (m, 4H).

Example 13: 1-methyl-9-(2-morpholinoethyl)-9H-pyrido[3,4-b]indol-7-ol

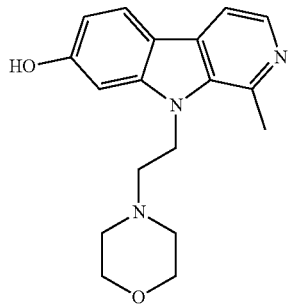 [SMILES: Cc1nccc2c3ccc(O)cc3n(CCN3CCOCC3)c12]

¹H NMR (DMSO-d₆, 400 MHz) δ 8.15 (d, 1H, J=5.2 Hz), 8.00 (d, 1H, J=8.4 Hz), 7.85 (d, 1H, J=5.2 Hz), 6.95 (d, 1H, J=2.0 Hz), 6.76 (dd, 1H, J=8.4, 2.0 Hz), 4.58 (t, 2H, J=7.2 Hz), 3.56 (t, 4H, J=4.4 Hz), 2.97 (s, 3H), 2.66 (m, 2H), 2.48 (m, 4H).

Example 14: t-butyl 4-(2-(7-methoxy-1-methyl-9H-pyrido[3,4-b]indol-9-yl)ethyl)piperazine-1-carboxylate

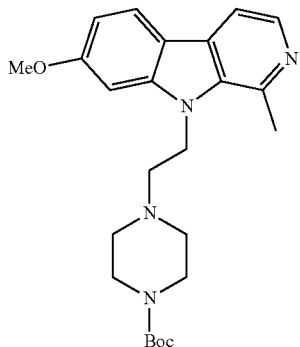 [SMILES: COc1ccc2c3ccnc(C)c3n(CCN3CCN(C(=O)OC(C)(C)C)CC3)c2c1]

¹H NMR (DMSO-d₆, 400 MHz) δ 8.16 (d, 1H, J=5.2 Hz), 8.09 (d, 1H, J=8.8 Hz), 7.87 (d, 1H, J=5.2 Hz), 7.16 (d, 1H, J=2.0 Hz), 6.87 (dd, 1H, J=8.6, 2.0 Hz), 4.67 (t, 2H, J=7.2 Hz), 3.90 (s, 3H), 3.24 (m, 4H), 2.97 (s, 3H), 2.68 (t, 2H, J=7.2 Hz), 2.42 (m, 4H), 1.38 (s, 9H).

Example 15: t-butyl 4-(3-(7-methoxy-1-methyl-9H-pyrido[3,4-b]indol-9-yl)propyl)piperazine-1-carboxylate

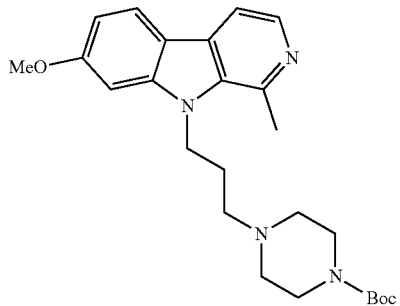 [SMILES: COc1ccc2c3ccnc(C)c3n(CCCN3CCN(C(=O)OC(C)(C)C)CC3)c2c1]

¹H NMR (DMSO-d₆, 400 MHz) δ 8.15 (d, 1H, J=4.8 Hz), 8.07 (d, 1H, J=8.8 Hz), 7.85 (d, 1H, J=5.2 Hz), 7.14 (d, 1H, J=2.0 Hz), 6.85 (dd, 1H, J=8.8, 2.0 Hz), 4.58 (t, 2H, J=7.2 Hz), 3.89 (s, 3H), 3.25 (m, 4H), 2.94 (s, 3H), 2.29 (t, 4H, J=6.4 Hz), 1.86 (m, 2H), 1.37 (s, 9H); LCMS m/z 439.27 ([M+H]⁺, C₂₅H₃₅N₄O₃ requires 439.27).

Example 16: 7-methoxy-1-methyl-9-(2-(piperazin-1-yl)ethyl)-9H-pyrido[3,4-b]indole

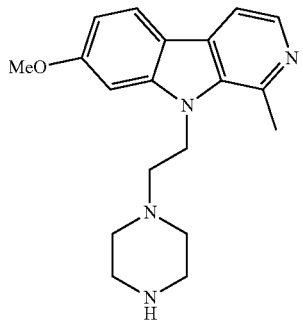 [SMILES: COc1ccc2c3ccnc(C)c3n(CCN3CCNCC3)c2c1]

Tert-butyl 4-(2-(7-methoxy-1-methyl-9H-pyrido[3,4-b]indol-9-yl)ethyl)piperazine-1-carboxylate (0.1 g, 0.236 mmol) was dissolved in a 1/3 mixture of trifluoroacetic acid (Sigma Aldrich, 299537) and dichlolromethane. The sample was allowed to stir until completion. The sample was concentrated envacuo and then purified via reverse phase chromatography (pH=9 water, acetonitrile) to provide 7-methoxy-1-methyl-9-(2-(piperazin-1-yl)ethyl)-9H-pyrido[3,4-b]indole (0.074 g, 0.228 mmol, 97% yield). ¹H NMR (CDCl₃, 400 MHz) δ 8.28 (d, 1H, J=5.2 Hz), 7.97 (d, 1H, J=8.4 Hz), 7.72 (d, 1H, J=5.2 Hz), 6.91 (d, 1H, J=2.0 Hz), 6.90 (d, 1H, J=2.0 Hz), 6.88 (d, 1H, J=2.0 Hz), 4.62 (t, 2H, J=8.0 Hz), 3.94 (s, 3H), 3.04 (s, 1H), 2.90 (t, 4H, J=4.8 Hz), 2.73 (t, 2H, J=7.6 Hz), 2.52 (m, 4H); LCMS m/z 325.20 ([M+H]⁺, C₁₉H₂₅N₄O requires 325.20).

Example 17: 7-methoxy-1-methyl-9-(3-(piperazin-1-yl)propyl)-9H-pyrido[3,4-b]indole trifluoroacetate

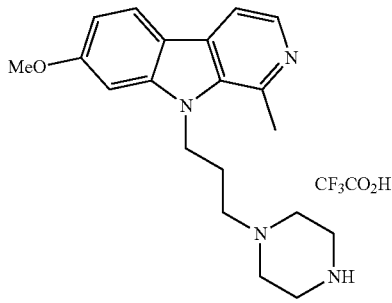 [SMILES: COc1ccc2c3ccnc(C)c3n(CCCN3CCNCC3)c2c1 ; "CF3CO2H"]

Example 17 can be synthesized from Example 15 using the procedure from Example 16. $^1$H NMR (DMSO-d$_6$, 400 MHz) δ 9.56 (bs, 1H), 8.53 (d, 1H, J=6.0 Hz), 8.45 (d, 1H, J=6.0 Hz), 8.39 (d, 1H, J=8.8 Hz), 7.40 (d, 1H, J=2.0 Hz), 7.08 (dd, 1H, J=8.8, 2.0 Hz), 4.72 (t, 2H, J=7.2 Hz), 3.98 (s, 3H), 3.40-3.31 (m, 10H), 3.19 (s, 3H), 2.21 (m, 2H); LCMS m/z 339.22 ([M+H]$^+$, C$_{20}$H$_{27}$N$_4$O requires 339.22).

Example 18: 2-((2-(7-methoxy-1-methyl-9H-pyrido[3,4-b]indol-9-yl)ethyl)(methyl)amino ethanol

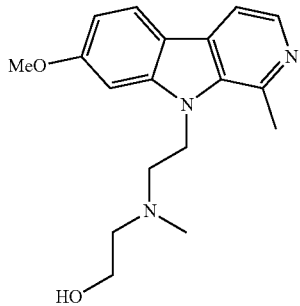 [SMILES: COc1ccc2c3ccnc(C)c3n(CCN(C)CCO)c2c1]

7-methoxy-1-methyl-9H-pyrido[3,4-b]indole hydrochloride (0.15 g, 0.603 mmol)) was dissolved in 3 mL of DMF and 3 mL of THF and transferred to a 10 mL round bottomed flask containing a stir bar. Sodium Hydride (0.096 g, 2.412 mmol) was added slowly to the reaction flask and then allowed to stir under argon for 30 minutes. tert-butyl (2-chloroethyl)(methyl)carbamate (0.234 g, 1.206 mmol) was then added as a 1 mL solution in a 1:1 mixture of DMF and THF. The reaction was then heated to 60° C. until completion. The reaction was quenched with water and then extracted three times with ethyl acetate. The organic phase was washed three times with water and then once with brine. The organic phase was then dried with sodium sulfate and then concentrated en vacuo. The crude residue was purified via normal phase and then reverse phase chromatography to givetert-butyl (2-(7-methoxy-1-methyl-9H-pyrido[3,4-b]indol-9-yl)ethyl)(methyl)carbamate (0.065 g, 0.176 mmol, 29.2% yield). The product was then dissolved in a 1:3 mixture of trifluoroacetic acid:dichloromethane and stirred until the reaction had completed. The reaction mixture was concentrated en vacuo, dissolved in dichloromethane, washed with sodium bicarbonate, dried with sodium sulfate and then concentrated en vacuo to give 2-(7-methoxy-1-methyl-9H-pyrido[3,4-b]indol-9-yl)-N-methylethanamine in >95% yield.

2-(7-methoxy-1-methyl-9H-pyrido[3,4-b]indol-9-yl)-N-methylethanamine (0.04 g, 0.149 mmol) was dissolved in 3 mL of DMF and 3 mL of THF and transfered to a 10 mL round bottomed flask containing a stir bar. Sodium Hydride (0.024 g, 0.594 mmol) was added slowly to the reaction flask and then allowed to stir under argon for 30 minutes. 2-bromoethanol (0.032 ml, 0.446 mmol) was then added as a 1 mL solution in a 1:1 mixture of DMF and THF. The reaction was then heated to 60° C. until completion. The reaction was quenched with water and then extracted three times with ethyl acetate. The organic phase was washed three times with water and then once with brine. The organic phase was then dried with sodium sulfate and then concentrated en vacuo. The crude residue was purified via normal phase and then reverse phase chromatography to give 2-((2-(7-methoxy-1-methyl-9H-pyrido[3,4-b]indol-9-yl)ethyl)(methyl)amino)ethanol (0.038 g, 0.121 mmol, 82% yield). $^1$H NMR (DMSO-d$_6$, 400 MHz) δ 8.16 (d, 1H, J=5.2 Hz), 8.08 (d, 1H, J=8.4 Hz), 7.87 (d, 1H, J=4.8 Hz), 7.15 (d, 1H, J=2.0 Hz), 6.86 (dd, 1H, J=8.4, 2.0 Hz), 4.63 (t, 2H, J=7.6 Hz), 4.37 (bs, 1H), 3.90 (s, 3H), 3.40 (m, 2H), 2.96 (s, 3H), 2.73 (t, 1H, J=7.6 Hz), 2.50 (m, 2H), 2.32 (s, 3H); LCMS m/z 314.19 ([M+H]$^+$, C$_{18}$H$_{24}$N$_3$O$_2$ requires 314.19).

Example 19: Synthesis of 7-methoxy-1-methyl-9H-pyrido[3,4-b]indol-3-ol 6-(benzyloxy)-3-bromo-2-methylpyridine (ArkPharm catalog # AK-27978, 0.1 g, 0.360 mmol), 2-(dicyclohexylphosphino)-2',4',6'-tri-i-propyl-1,1'-biphenyl (Chemimpex catalog #27675, 0.013 g, 0.027 mmol), cesium carbonate (0.141 g, 0.431 mmol) and palladium (II) acetate (4.04 mg, 0.018 mmol) were added to a microwave vial containing a stir bar and 5 mL of anhydrous toluene. Then, 2-chloro-5-methoxyaniline (Chemimpex catalog #27675, 0.059 g, 0.378 mmol) was added. The solvent was degassed with argon twice. The reaction was heated on a heating block to 100° C. for 15 hours. The crude reaction mixture was cooled to room temperature and then filtered through celite. The celite was rinsed repeatedly with ethyl acetate to collect the crude product mixture. A normal phase ethylacetate/hexanes column was run on the crude mixture to give 6-(benzyloxy)-N-(2-chloro-5-methoxyphenyl)-2-methylpyridin-3-amine (0.1195 g, 94% yield). $^1$H NMR (CDCl3, 400 MHz) δ 7.39 (m, 6H), 7.20 (d, 1H, J=8.8 Hz), 6.67 (d, 1H, J=8.4 Hz), 6.26 (dd, 1H, J=2.8, 8.8 Hz), 6.01 (d, 1H, J=2.8 Hz), 5.65 (s, 1H), 5.37 (s, 2H), 3.65 (s, 3H), 2.38 (s, 3H).

6-(benzyloxy)-N-(2-chloro-5-methoxyphenyl)-2-methylpyridin-3-amine (0.1195 g, 0.337 mmol), N,N-dimethylacetamide (5 mL), tri-t-butylphosphonium tetrafluoroborate (0.020 g, 0.067 mmol), potassium carbonate (0.093 g, 0.674 mmol), and palladium (II) acetate (7.56 mg, 0.034 mmol) were added to a microwave sample vessel. The solvent was degassed with argon twice. The microwave vial was heated in a microwave at 150° C. for three hours. The crude reaction mixture was filtered through celite. The celite was washed repeatedly with ethyl acetate. The combined organic fractions were washed with water twice, brine twice, dried with sodium sulfate and then concentrated en vacuo. Normal phase chromatography (methanol/DCM) was performed, followed by a reverse phase chromatography (water/acetonitrile) to give 3-(benzyloxy)-7-methoxy-1-methyl-9H-pyrido [3,4-b]indole (0.135 g, 75% yield). $^1$H NMR (CDCl3, 400 MHz) δ 8.98 (bs, 1H), 7.69 (d, 1H, J=8.4 Hz), 7.42 (d, 1H, J=7.2 Hz), 7.25 (m, 3H), 6.90 (s, 1H), 6.84 (s, 1H), 6.69 (d, 1H, J=8.4 Hz), 5.22 (s, 2H), 3.65 (s, 3H), 2.73 (s, 3H). LCMS m/z 319.15 ([M+H]$^+$, $C_{20}H_{19}N_2O_2$ requires 319.14).

3-(benzyloxy)-7-methoxy-1-methyl-9H-pyrido[3,4-b]indole (0.07 g, 0.220 mmol) was dissolved in THF (10 mL) in around bottomed flask equipped with a stir bar and rubber septum. 10% palladium on carbon (0.014 g, 0.132 mmol) was added slowly. The reaction chamber was purged repeatedly with hydrogen gas (double balloon pressure). Then, the reaction was left under balloon filled hydrogen gas pressure for three hours. The crude reaction mixture was then filtered through celite. The celite was washed with ethyl acetate repeatedly followed by a concentration en vacuo of the combined organic washings. The residue was purified via normal phase chromatography (methanol/dichloromethane) and then reverse phase chromatography (water, acetonitrile) to give 7-methoxy-1-methyl-9H-pyrido[3,4-b]indol-3-ol (0.046 g, 92% yield).

$^1$H NMR (DMSO-d$_6$, 500 MHz) δ 10.69 (bs, 2H), 7.87 (d, 1H, J=8.5 Hz), 6.80 (d, 1H, J=2.0 Hz), 6.73 (s, 1H), 6.66 (dd, 1H, J=2.0, 8.5 Hz), 3.83 (s, 3H), 2.50 (s, 3H). LCMS m/z 229.09 ([M+H]$^+$, $C_{13}H_{13}N_2O_2$ requires 229.10).

The compound of Example 19 can be converted to compounds of Formula I or Formula II through the corresponding 3-(benzyloxy)-7-methoxy-1-methyl-9H-pyrido[3, 4-b]indole intermediate using the procedure described in Example 3 and Scheme 1 and then using the debenzylation procedure described in Example 19.

Example 20: Synthesis of 1-methyl-9H-pyrido[3,4-b]indole-3,7-diol

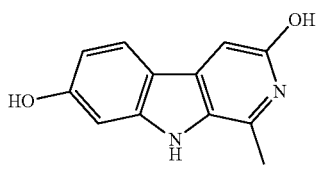 [SMILES: Cc1nc(O)cc2c1[nH]c1cc(O)ccc12]

7-methoxy-1-methyl-9H-pyrido[3,4-b]indol-3-ol (0.013 g, 0.057 mmol) was dissolved in THF and then cooled to −78° C. Then, boron tribromide (1N solution in dichloromethane) (0.285 mL, 0.285 mmol) was added drop-wise. The reaction was allowed to slowly warm to room temperature until the reaction was completed as determined by UPLC. The reaction was then cooled to −78° C. and then quenched by the drop-wise addition of methanol. The reaction mixture was concentrated en vacuo and then purified via normal phase chromatography to give 1-methyl-9H-pyrido [3,4-b]indole-3,7-diol (0.0058 g, 47% yield). $^1$H NMR (DMSO-d$_6$, 500 MHz) δ 10.35 (s, 1H), 7.69 (d, 1H, J=8.5 Hz), 6.62 (d, 1H, J=2.0 Hz), 6.57 (s, 1H), 6.48 (dd, 1H, J=2.0, 8.5 Hz), 2.45 (s, 3H). LCMS m/z 215.08 ([M+H]$^+$, $C_{12}H_{12}N_2O_2$ requires 215.08).

The compound of Example 20 can be converted to compounds of Formula I or Formula II through the corresponding 3-(benzyloxy)-7-methoxy-1-methyl-9H-pyrido[3, 4-b]indole intermediate using the procedure described in Example 3 and Scheme 1 and then using the debenzylation procedure described in Example 19 and demethylation procedure in Example 20.

Example 21: Synthesis of 7-methoxy-1-methyl-9H-pyrido[3,4-b]indole pyridine N-oxide

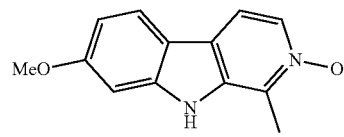

7-methoxy-1-methyl-9H-pyrido[3,4-b]indole (Chemimpex catalog #21756, 0.1 g, 0.471 mmol) was dissolved in a mixture of 5 mL chloroform and 5 mL ethanol and m-chloroperbenzoic acid (0.317 g, 1.413 mmol) is added. The reaction mixture was refluxed for 2 h, then allowed to cool to room temperature after which 3 mL of 0.1 M NaOH was added and stirring was continued for 30 min. The organic layer was dried with Na$_2$SO$_4$ and the solvents were evaporated. The residue was purified via normal phase chromatography (ethyl acetate/MeOH) to give the product (0.087 g, 81% yield). $^1$H NMR (DMSO-d$_6$, 400 MHz) δ 11.60 (s, 1H), 8.05 (d, 1H, J=6.8 Hz), 8.00 (d, 1H, J=8.8 Hz), 7.86 (d, 1H, J=6.4 Hz), 6.98 (d, 1H, J=2.4 Hz), 6.86 (dd, 1H, J=2.0, 8.6 Hz), 3.85 (s, 3H), 2.63 (s, 3H). LCMS m/z 229.09 ([M+H]$^+$, $C_{13}H_{13}N_2O_2$ requires 229.10).

The compound of Example 21 can then converted to compounds of Formula I or Formula II using the procedure described in Example 3 and Scheme 1.

Example 22: Synthesis of 7-methoxy-1-(trifluoromethyl)-9H-pyrido[3,4-b]indole

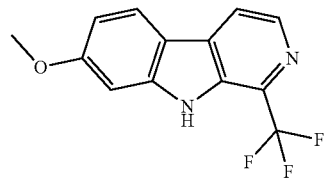 [SMILES: COc1ccc2c(c1)[nH]c1c(C(F)(F)F)nccc12]

3-bromo-2-(trifluoromethyl)pyridine (Matrix catalog #032388, 0.2 g, 0.885 mmol), anhydrous toluene (5 mL), 2-(Dicyclohexylphosphino)-2',4',6'-tri-i-propyl-1,1'-biphenyl (0.032 g, 0.066 mmol), cesium carbonate (0.346 g, 1.062 mmol) and palladium (II) acetate (9.93 mg, 0.044 mmol) were added to a microwave vial. Then, 2-chloro-5-methoxyaniline (Chemimpex catalog #27675, 0.146 g, 0.929 mmol) was added. The solvent was degassed with argon twice. The reaction was heated on a heating block to 100° C. for 15 hours. The crude reaction mixture was cooled to room temperature and then filtered through celite. The celite was rinsed repeatedly with ethyl acetate to collect the crude product mixture. A normal phase ethylacetate/hexanes column was run on the crude mixture to give N-(2-chloro-5-methoxyphenyl)-2-(trifluoromethyl)pyridin-3-amine (0.1182 g, 44% yield). $^1$H NMR (CDCl$_3$, 400 MHz) δ 8.28 (dd, 1H, J=0.6, 4.4 Hz), 7.74 (d, 1H, J=8.4 Hz), 7.37 (m, 2H), 6.76 (d, 1H, J=2.8 Hz), 6.56 (dd, 1H, J=2.8, 8.8 Hz), 6.46 (s, 1H), 3.76 (s, 3H).

N-(2-chloro-5-methoxyphenyl)-2-(trifluoromethyl)pyridin-3-amine (0.110 g, 0.364 mmol), N,N-dimethylacetamide (5 mL), tri-t-butylphosphonium tetrafluoroborate (0.053 g, 0.182 mmol), potassium carbonate (0.101 g, 0.728 mmol), and palladium (II) acetate (16 mg, 0.073 mmol) were added to a microwave sample vessel. The solvent was degassed with argon twice. The microwave vial was heated in a microwave at 150° C. for three hours. The crude reaction mixture was filtered through celite. The celite was washed repeatedly with ethyl acetate. The combined organic fractions were washed with water twice, brine twice, dried with sodium sulfate and then concentrated en vacuo. Normal phase chromatography (methanol/DCM) was performed, followed by a reverse phase chromatography (water/acetonitrile) to give 7-methoxy-1-(trifluoromethyl)-9H-pyrido[3,4-b]indole (0.067 g, 69% yield). $^1$H NMR (CDCl$_3$, 400 MHz) δ 8.631 (s, 1H), 8.49 (d, 1H, J=5.2 Hz), 8.01 (d, 1H, J=8.4 Hz), 7.99 (d, 1H, J=5.6 Hz), 6.99 (d, 1H, J=2.4 Hz), 6.95 (dd, 1H, J=2.4, 8.4 Hz), 3.92 (s, 3H). LCMS m/z 267.07 ([M+H]$^+$, C$_{13}$H$_{10}$F$_3$N$_2$O requires 267.07).

The compound of Example 22 is then converted to compounds of Formula I or Formula II using the procedure described in Example 3 and Scheme 1.

Example 23: 1-(trifluoromethyl)-9H-pyrido[3,4-b]indol-7-ol

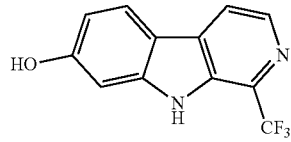 [SMILES: Oc1ccc2c(c1)[nH]c1c(C(F)(F)F)nccc12]

3-bromo-2-(trifluoromethyl)pyridine (0.4 g, 1.770 mmol), 2-(Dicyclohexylphosphino)-2',4',6'-tri-i-propyl-1,1'-biphenyl (0.063 g, 0.133 mmol), Cesium carbonate (0.692 g, 2.124 mmol) and Palladium (II) Acetate (0.020 g, 0.088 mmol) were added to a microwave vial. Then, 2-chloro-5-methoxyaniline (0.293 g, 1.858 mmol) was added. The vial was purged with argon repeatedly. Dry toluene was added. The reaction was heated to 100° C. for 15 hours. The reaction mixture was filtered through celite, concentrated en vacuo. Normal phase chromatography (ethyl acetate/hexanes) was used to purify the crude material to give N-(2-chloro-5-methoxyphenyl)-2-(trifluoromethyl)pyridin-3-amine (0.376 g, 1.242 mmol, 70.2% yield).

N-(2-chloro-5-methoxyphenyl)-2-(trifluoromethyl)pyridin-3-amine (0.2382 g, 0.787 mmol) was dissolved in DMA and then placed in a 5 mL microwave reaction tube. The solution was degassed with argon. Next, Palladium (II) Acetate (0.035 g, 0.157 mmol), Tri-t-butylphosphonium tetrafluoroborate (0.114 g, 0.393 mmol) and Potassium Carbonate (0.218 g, 1.574 mmol) was added. The head space was purged with argon and then the microwave tube was resealed. The reaction vessel was heated in a reaction microwave at 150° C. for 3.5 hours. The crude reaction mixture was filtered through celite. Ethyl acetate was added to the filtrate, then washed with water three times, brine once, dried with sodium sulfate and then concentrated en vacuo. The crude reaction mixture was purified via normal phase (MeOH/DCM) and then reverse phase chromatography to give 7-methoxy-1-(trifluoromethyl)-9H-pyrido[3,4-b]indole (0.067 g, 0.252 mmol, 32.0% yield). The product was dissolved in 1 mL of dichloromethane and then cooled to −78° C. in an acetone/dry ice bath. Then, 3 mL of 1N BBr3/DCM was added slowly. The reaction was allowed to stir until the reaction was completed. The reaction was quenched with a few drops of methanol and then concentrated en vacuo. The crude reaction mixture was purified via reverse phase chromatography to give 1-(trifluoromethyl)-9H-pyrido[3,4-b]indol-7-ol (>95% yield). LCMS m/z 253.06 ([M+H]$^+$, C$_{12}$H$_8$F$_3$N$_2$O requires 253.06).

Example 23 derivatives of Formula I or Formula II are accessed through Example 22 using the procedure described in Example 3 and Scheme 1 and then using the demethylation procedure described in Example 23.

Example 24: t-butyl 4-(2-(7-methoxy-1-(trifluoromethyl)-9H-pyrido[3,4-b]indol-9-yl)ethyl)piperazine-1-carboxylate

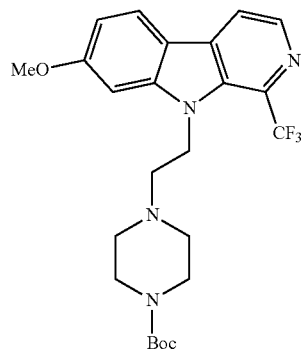 [SMILES: COc1ccc2c3ccnc(C(F)(F)F)c3n(CCN3CCN(C(=O)OC(C)(C)C)CC3)c2c1]

$^1$H NMR (DMSO-d$_6$, 400 MHz) δδ 8.45 (d, 1H, J=4.8 Hz), 8.41 (d, 1H, J=4.8 Hz), 8.25 (d, 1H, J=8.6 Hz), 7.25 (d, 1H, J=2.1 Hz), 7.01 (dd, 1H, J=8.6, 2.1 Hz), 4.60 (t, 2H, J=7.6 Hz), 3.95 (s, 3H), 3.28 (m, 4H), 2.66-2.58 (m, 2H), 2.46-2.34 (m, 4H), 1.39 (s, 9H).

Example 25: 4-(2-(7-methoxy-1-(trifluoromethyl)-9H-pyrido[3,4-b]indol-9-yl)ethyl)morpholine

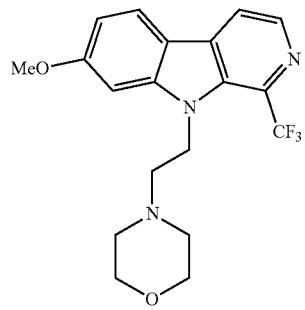 [SMILES: COc1ccc2c3ccnc(C(F)(F)F)c3n(CCN3CCOCC3)c2c1]

$^1$H NMR (DMSO-d$_6$, 400 MHz) δ 8.44 (d, 1H, J=5.2 Hz), 8.41 (d, 1H, J=5.2 Hz), 8.25 (d, 1H, J=8.8 Hz), 7.25 (d, 1H, J=2.4 Hz), 7.00 (dd, 1H, J=8.4, 2.0 Hz), 4.61 (t, 2H, J=7.2 Hz), 3.94 (s, 3H), 3.53 (t, 4H, J=4.4 Hz), 2.60 (t, 2H, J=7.2

Hz), 2.44 (m, 4H); LCMS m/z 380.16 ([M+H]$^+$, $C_{19}H_{21}F_3N_3O_2$ requires 380.16).

Example 26: 9-(2-morpholinoethyl)-1-(trifluoromethyl)-9H-pyrido[3,4-b]indol-7-ol

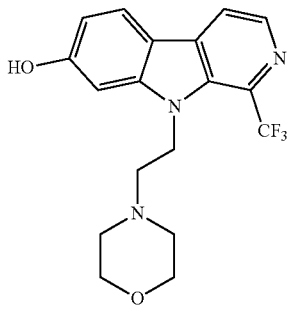

$^1$H NMR (DMSO-d$_6$, 400 MHz) δ 10.24 (bs, 1H), 8.39 (d, 1H, J=5.2 Hz), 8.33 (d, 1H, J=5.2 Hz), 8.14 (d, 1H, J=8.5 Hz), 7.01 (d, 1H, J=2.0 Hz), 6.86 (dd, 1H, J=8.8, 2.0), 4.49 (t, 2H, J=8 Hz), 3.56 (t, 4H, J=4.4 Hz), 2.58 (t, 2H, J=8.4 Hz), 2.46 (t, 2H, J=4.8 Hz); LCMS m/z 366.14 ([M+H]$^+$, $C_{18}H_{19}F_3N_3O_2$ requires 366.14).

Example 27: 1-(7-methoxy-1-(trifluoromethyl)-9H-pyrido[3,4-b]indol-9-yl)-N,N-dimethylpropan-2-amine

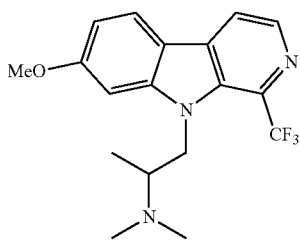 [SMILES: COc1ccc2c3ccnc(C(F)(F)F)c3n(CC(C)N(C)C)c2c1]

$^1$H NMR (DMSO-d$_6$, 400 MHz) δ 8.45 (d, 1H, J=4.8 Hz), 8.41 (d, 1H, J=5.2 Hz), 8.23 (d, 1H, J=8.8 Hz), 7.32 (d, 1H, J=2.0 Hz), 76.98 (dd, 1H, J=8.4, 2.0 Hz), 4.61 (dd, 1H, J=15.2, 6.8 Hz), 4.36 (dd, 1H, J=15.6, 7.2 Hz), 3.93 (s, 3H), 3.03 (q, 1H, J=4.0 Hz), 2.15 (s, 1H), 0.65 (d, 3H, J=6.4 Hz).

Example 28: 4-(1-(7-methoxy-1-(trifluoromethyl)-9H-pyrido[3,4-b]indol-9-yl)propan-2-yl)morpholine

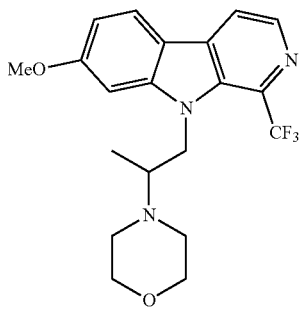 [SMILES: COc1ccc2c3ccnc(C(F)(F)F)c3n(CC(C)N3CCOCC3)c2c1]

$^1$H NMR (DMSO-d$_6$, 400 MHz) δ 8.47 (d, 1H, J=4.8 Hz), 8.41 (d, 1H, J=4.8 Hz), 8.24 (d, 1H, J=8.4 Hz), 7.36 (d, 1H, J=2.4 Hz), 6.99 (dd, 1H, J=8.8, 2.0 Hz), 4.64 (dd, 1H, J=15.6, 8.4 Hz), 4.36 (dd, 1H, J=15.6, 6.4 Hz), 3.93 (s, 3H), 3.15 (m, 4H), 2.94 (s, 1H), 2.58 (m, 2H), 2.05 (m, 2H), 0.78 (d, 3H, J=6.8 Hz); LCMS m/z 394.17 ([M+H]$^+$, $C_{20}H_{23}F_3N_3O_2$ requires 394.17).

Example 29: 4-(2-(7-methoxy-1-(trifluoromethyl)-9H-pyrido[3,4-b]indol-9-yl)ethyl)-3-methylmorpholine

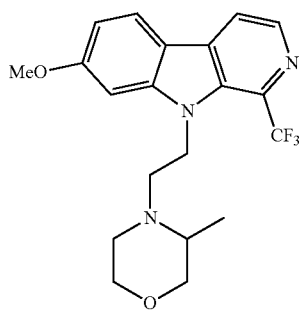 [SMILES: COc1ccc2c3ccnc(C(F)(F)F)c3n(CCN3CCOCC3C)c2c1]

$^1$H NMR (CDCl$_3$, 400 MHz) δ 8.45 (d, 1H, J=4.8 Hz), 8.05 (d, 1H, J=4.8 Hz), 8.02 (d, 1H, J=8.4 Hz), 7.00 (d, 1H, J=2.0 Hz), 6.97 (dd, 1H, J=8.4, 2.0 Hz), 4.64 (m, 1H), 4.49 (m, 1H) 3.96 (s, 3H), 3.83 (m, 1H), 3.68 (m, 2H), 3.23 (m, 1H), 3.12 (m, 1H), 2.90 (m, 1H), 2.51 (m, 3H), 0.95 (d, 3H, J=6.4 Hz).

Example 30: 9-(2-(3-methylmorpholino)ethyl)-1-(trifluoromethyl)-9H-pyrido[3,4-b]indol-7-ol

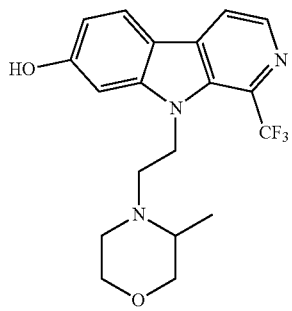

$^1$H NMR (CDCl$_3$, 400 MHz) δ 8.45 (d, 1H, J=4.8 Hz), 8.02 (d, 1H, J=4.8 Hz), 7.97 (d, 1H, J=8.4 Hz), 7.06 (d, 1H, J=2.0 Hz), 6.91 (dd, 1H, J=8.4, 2.0 Hz), 4.59 (m, 1H), 4.53 (m, 1H), 3.82 (m, 1H), 3.69 (m, 2H), 3.29 (m, 1H), 3.14 (m, 1H), 2.94 (m, 1H), 2.56 (m, 3H), 0.95 (d, 3H, J=6.4 Hz).

Example 31: 9-(2-(2,6-dimethylmorpholino)ethyl)-1-(trifluoromethyl)-9H-pyrido[3,4-b]indol-7-ol

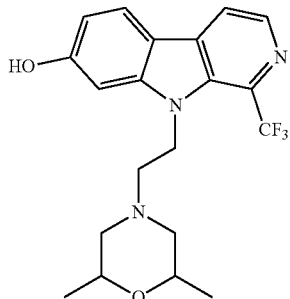

From 7-methoxy-1-(trifluoromethyl)-9H-pyrido[3,4-b]indole was synthesized 4-(2-(7-methoxy-1-(trifluoromethyl)-9H-pyrido[3,4-b]indol-9-yl)ethyl)-2,6-dimethylmorpholine using procedure in Example 3. $^1$H NMR (CDCl$_3$, 400 MHz) δ 8.43 (d, 1H, J=4.8 Hz), 8.00 (m, 2H), 7.02 (d, 1H, J=2.0 Hz), 6.95 (dd, 1H, J=8.4, 2.0 Hz), 4.59 (t, 2H, J=7.6 Hz), 3.96 (s, 3H), 3.70 (m, 2H), 2.77 (m, 4H), 2.52 (m, 2H), 1.17 (d, 6H, J=6.4 Hz).

From 4-(2-(7-methoxy-1-(trifluoromethyl)-9H-pyrido[3,4-b]indol-9-yl)ethyl)-2,6-dimethyl morpholine was synthesized 9-(2-(2,6-dimethylmorpholino)ethyl)-1-(trifluoromethyl)-9H-pyrido[3,4-b]indol-7-ol using demethylation procedure in Example 23. $^1$H NMR (CDCl$_3$, 400 MHz) δ 8.47 (d, 1H, J=4.8 Hz), 8.01 (d, 1H, J=5.2 Hz), 7.96 (d, 1H, J=8.4 Hz), 7.49 (s, 1H), 6.94 (d, 1H, J=8.4 Hz), 4.98 (m, 2H), 4.16 (m, 2H), 3.30 (m, 2H), 3.15 (m, 2H), 2.35 (m, 2H), 1.25 (s, 6H).

Example 32: 9-(2-(3,3-dimethylmorpholino)ethyl)-1-(trifluoromethyl)-9H-pyrido[3,4-b]indol-7-ol

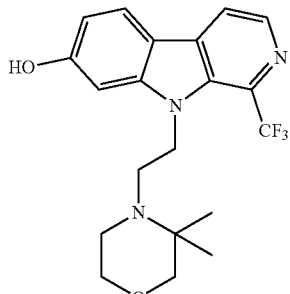

$^1$H NMR (CDCl$_3$, 400 MHz) δ 8.29 (d, 1H, J=5.2 Hz), 7.92 (d, 1H, J=8.4 Hz), 7.78 (d, 1H, J=5.2 Hz), 6.93 (d, 1H, J=2.0 Hz), 6.91 (dd, 1H, J=8.4, 2.0 Hz), 4.46 (t, 2H, J=7.2 Hz), 3.60 (t, 2H, J=4.8 Hz), 3.20 (s, 2H), 2.71 (t, 2H, J=7.2 Hz), 2.55 (t, 2H, J=4.8 Hz), 0.69 (s, 1H).

Example 33: 7-methoxy-9-(2-(piperidin-1-yl)ethyl)-1-(trifluoromethyl)-9H-pyrido[3,4-b]indole

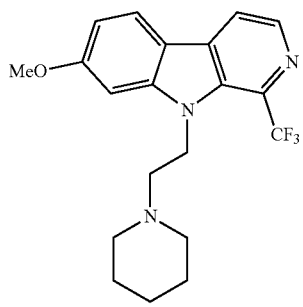 [SMILES: COc1ccc2c3ccnc(C(F)(F)F)c3n(CCN3CCCCC3)c2c1]

$^1$H NMR (DMSO-d$_6$, 400 MHz) δ 8.45 (d, 1H, J=5.2 Hz), 8.41 (d, 1H, J=4.8 Hz), 8.25 (d, 1H, J=8.8 Hz), 7.25 (d, 1H, J=2.0 Hz), 7.01 (dd, 1H, J=8.8, 2.0 Hz), 4.58 (t, 2H, J=7.6 Hz), 3.96 (s, 3H), 2.54 (m, 2H), 2.42 (m, 4H), 1.46 (m, 4H), 1.37 (m, 2H).

Example 34: 2-((2-(7-methoxy-1-(trifluoromethyl)-9H-pyrido[3,4-b]indol-9-yl)ethyl)amino ethanol $^1$H NMR (CDCl$_3$, 400 MHz) δ 8.45 (d, 1H, J=5.2 Hz), 8.05 (d, 1H, J=5.2 Hz), 8.02 (d, 1H, J=8.4 Hz), 7.03 (d, 1H, J=2.4 Hz), 6.97 (dd, 1H, J=8.8, 2.2 Hz), 4.60 (d, 2H, J=7.2 Hz), 4.00 (s, 3H), 3.65 (t, 2H, J=5.2 Hz), 3.06 (t, 2H, J=7.6 Hz), 2.84 (t, 2H, J=5.2 Hz).

Example 34 derivatives of Formula I or Formula II are accessed through Example 22 using the procedure described in Example 18 and Scheme 1. A demethylation procedure described in Example 4 is used to provide additional phenol derivatives.

Example 35: 2,2'-((2-(7-methoxy-1-(trifluoromethyl)-9H-pyrido[3,4-b]indol-9-yl)ethyl)azanediyl)diethanol

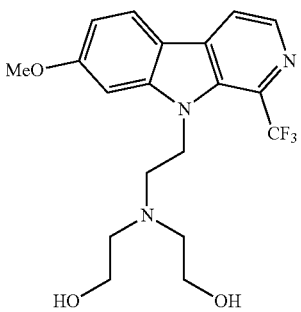 [SMILES: COc1ccc2c3ccnc(C(F)(F)F)c3n(CCN(CCO)CCO)c2c1]

$^1$H NMR (CDCl$_3$, 400 MHz) δ 8.46 (d, 1H, J=5.2 Hz), 8.05 (m, 2H), 7.06 (d, 1H, J=2.4 Hz), 6.97 (dd, 1H, J=8.8, 2.4 Hz), 4.63 (d, 2H, J=8.0 Hz), 3.97 (s, 3H), 3.69 (t, 4H, J=5.2 Hz), 2.98 (t, 2H, J=8.0 Hz), 2.84 (t, 4H, J=5.6 Hz).

Example 36: 2,2'-((2-(7-hydroxy-1-(trifluoromethyl)-9H-pyrido[3,4-b]indol-9-yl)ethyl)azanediyl)diethanol

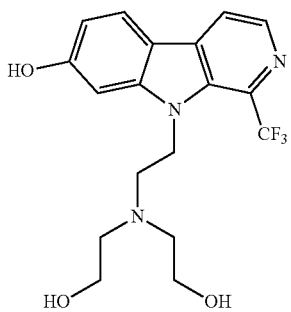 [SMILES: OCCN(CCO)CCn1c2cc(O)ccc2c2ccnc(C(F)(F)F)c21]

$^1$H NMR (DMSO-d$_6$, 400 MHz) δ 10.30 (s 1H), 9.75 (s, 1H), 8.93 (s, 1H), 8.45 (d, 1H, J=4.8 Hz), 8.38 (d, 1H, J=4.8 Hz), 8.20 (d, 1H, J=8.4 Hz), 7.25 (d, 1H, J=2.4 Hz), 6.94 (dd, 1H, J=8.4, 2.0 Hz), 4.82 (t, 2H, J=8.4 Hz), 3.82 (t, 4H, J=5.6 Hz), 3.44 (m, 4H), 3.10-2.90 (m, 2H).

Example 37: Synthesis of 7-methoxy-4-methyl-5H-pyrido[3,2-b]indole

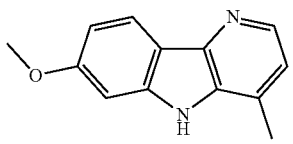 [SMILES: COc1ccc2c(c1)[nH]c1c(C)ccnc12]

3-bromo-4-methylpyridine (Matrix catalog #011246, 0.266 g, 1.547 mmol), 2-(dicyclohexylphosphino)-2',4',6'-tri-i-propyl-1,1'-biphenyl (0.055 g, 0.116 mmol), cesium carbonate (0.605 g, 1.856 mmol) and palladium (II) acetate (0.017 g, 0.077 mmol) were added to a microwave vial. Then, 3-methoxyaniline (Aldrich catalog # A88204-100G, 0.2 g, 1.624 mmol) was added. The solvent was degassed with argon twice. The reaction was heated on a heating block to 100° C. for 15 hours. The crude reaction mixture was cooled to room temperature and then filtered through celite. The celite was rinsed repeatedly with ethyl acetate to collect the crude product mixture. A normal phase ethylacetate/hexanes column was run on the crude mixture to give N-(3-methoxyphenyl)-4-methylpyridin-3-amine (0.246 g, 74% yield).

$^1$H NMR (CDCl$_3$, 400 MHz) δ 8.49 (s, 1H), 8.19 (d, 1H, J=4.8 Hz), 7.18-7.11 (m, 2H), 6.50-6.42 (m, 3H), 5.34 (s, 1H), 3.76 (s, 1H), 2.25 (s, 1H).

N-(3-methoxyphenyl)-4-methylpyridin-3-amine (0.245 g, 1.143 mmol) was dissolved in trifluoroacetic acid (20 mL) in a round bottomed flask equipped with a stir-bar and reflux condenser. Then, palladium (II) acetate (0.19 g, 0.846 mmol) was added slowly in small increments. The reaction mixture was refluxed for three hours. The crude mixture was concentrated en vacuo and then purified via reverse phase chromatography (water (pH=9.5), acetonitrile) to afford 7-methoxy-4-methyl-5H-pyrido[3,2-b]indole (0.193 g, 80% yield). $^1$H NMR (DMSO-d$_6$, 400 MHz) δ 11.31 (s, 1H), 8.25 (d, 1H, J=4.8 Hz), 8.01 (d, 1H, J=8.8 Hz), 7.12 (dd, 1H, J=0.8, 4.8 Hz), 7.00 (d, 1H, J=2.0 Hz), 6.85 (dd, 1H, J=2.4, 8.6 Hz), 3.88 (s, 3H), 2.56 (s, 3H). LCMS m/z 213.10 ([M+H]$^+$, C$_{13}$H$_{13}$N$_2$O requires 213.10).

The compound of Example 37 can be converted to compounds of Formula I or Formula II using the procedure described in Example 3 and Scheme 1.

Example 38: Synthesis of 3-fluoro-7-methoxy-1-methyl-9H-pyrido[3,4-b]indole

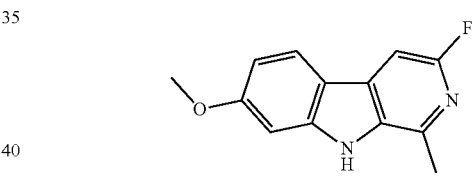

3-bromo-6-fluoro-2-methylpyridine (Matrix catalog #024607, 0.230 g, 1.209 mmol), 2-(dicyclohexylphosphino)-2',4',6'-tri-i-propyl-1,1'-biphenyl (0.043 g, 0.091 mmol), cesium carbonate (0.473 g, 1.450 mmol) and palladium (II) acetate (0.014 g, 0.060 mmol) were added to a microwave vial. Then, 2-chloro-5-methoxyaniline (0.2 g, 1.269 mmol) was added. The solvent was degassed with argon twice. The reaction was heated on a heating block to 100° C. for 15 hours. The crude reaction mixture was cooled to room temperature and then filtered through celite. The celite was rinsed repeatedly with ethyl acetate to collect the crude product mixture. A reverse-phase column was run (water, acetonitrile) to give N-(2-chloro-5-methoxyphenyl)-6-fluoro-2-methylpyridin-3-amine (0.246 g, 76% yield). $^1$H NMR (CDCl$_3$, 400 MHz) δ 7.65 (t, 1H, J=8.4 Hz), 7.24 (s, 1H), 6.79 (dd, 1H, J=3.6, 8.4 Hz), 6.35 (dd, 1H, J=2.8, 8.8 Hz), 6.15 (d, 1H, J=2.8 Hz), 5.71 (s, 1H), 3.69 (s, 3H), 2.44 (s, 3H).

N-(2-chloro-5-methoxyphenyl)-6-fluoro-2-methylpyridin-3-amine (0.217 g, 0.812 mmol), N,N-dimethylacetamide (5 ml), tri-t-butylphosphonium tetrafluoroborate (0.118 g, 0.406 mmol), potassium carbonate (0.224 g, 1.624 mmol), and palladium (II) acetate (0.036 mg, 0.162 mmol) were added to a microwave sample vessel. The solvent was degassed with argon twice. The microwave vial was heated in a microwave at 150° C. for three hours. The crude reaction mixture was filtered through celite. The celite was washed repeatedly with ethyl acetate. The combined organic fractions were washed with water twice, brine twice, dried with sodium sulfate and then concentrated en vacuo. Normal phase chromatography (methanol/DCM) was performed, followed by a reverse phase chromatography (water/acetonitrile) to give 3-fluoro-7-methoxy-1-methyl-9H-pyrido[3,4-b]indole (0.11 g, 58% yield). $^1$H NMR (DMSO-$d_6$, 400 MHz) δ 11.45 (s, 1H), 8.07 (d, 1H, J=8.8 Hz), 7.51 (d, 1H, J=2.0 Hz), 6.98 (d, 1H, J=2.4 Hz), 6.84 (dd, 1H, J=2.4, 8.4 Hz), 3.88 (s, 3H), 2.67 (s, 3H). LCMS m/z 231.09 ([M+H]$^+$, $C_{13}H_{12}FN_2O$ requires 231.09).

The compound of Example 38 is then converted to compounds of Formula I or Formula II using the procedure described in Example 3 and Scheme 1.

Example 39: 3-fluoro-7-methoxy-1-methyl-9-(2-(piperidin-1-yl)ethyl)-9H-pyrido[3,4-b]indole

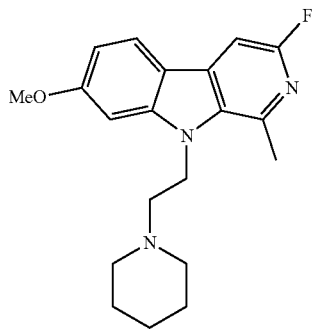 [SMILES: COc1ccc2c3cc(F)nc(C)c3n(CCN3CCCCC3)c2c1]

$^1$H NMR (DMSO-$d_6$, 400 MHz) δδ 8.10 (d, 1H, J=8.6 Hz), 7.59 (d, 1H, J=2.6 Hz), 7.13 (d, 1H, J=2.2 Hz), 6.86 (dd, 1H, J=8.7, 2.2 Hz), 4.61 (t, 2H, J=7.1 Hz), 3.92 (s, 3H), 2.90 (s, 3H), 2.60 (t, 2H, J=7.0 Hz), 2.43-2.32 (m, 4H), 1.42 (m, 4H), 1.34 (m, 2H).

Example 40: Synthesis of 3,7-dimethoxy-1-methyl-9H-pyrido[3,4-b]indole

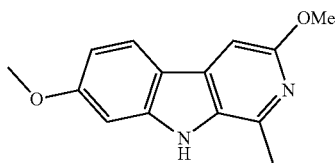 [SMILES: COc1ccc2c(c1)[nH]c1c(C)nc(OC)cc12]

3-bromo-6-methoxy-2-methylpyridine (Aldrich catalog #758191-1G, 0.3 g, 1.485 mmol), 2-(dicyclohexylphosphino)-2',4',6'-tri-i-propyl-1,1'-biphenyl (0.053 g, 0.111 mmol), cesium carbonate (0.581 g, 1.782 mmol) and palladium (II) acetate (0.017 g, 0.074 mmol) were added to a microwave vial. Then, 2-chloro-5-methoxyaniline (Chemimpex catalog #27675, 0.246 g, 1.559 mmol) was added. The solvent was degassed with argon twice. The reaction was heated on a heating block to 100° C. for 15 hours. The crude reaction mixture was cooled to room temperature and then filtered through celite. The celite was rinsed repeatedly with ethyl acetate to collect the crude product mixture. A reverse-phase column was run (water, acetonitrile) to give N-(2-chloro-5-methoxyphenyl)-6-methoxy-2-methylpyridin-3-amine (0.286 g, 69% yield). $^1$H NMR (CDCl$_3$, 400 MHz) δ 7.42 (d, 1H, J=8.4 Hz), 7.20 (d, 1H, J=8.4 Hz), 6.60 (d, 1H, J=8.4 Hz), 6.26 (dd, 1H, J=2.8, 8.8 Hz), 6.00 (d, 1H, J=2.8 Hz), 5.65 (s, 1H), 3.93 (s, 3H), 3.66 (s, 3H), 2.37 (s, 3H).

N-(2-chloro-5-methoxyphenyl)-6-methoxy-2-methylpyridin-3-amine (0.1697 g, 0.609 mmol), N,N-dimethylacetamide (5 mL), tri-t-butylphosphonium tetrafluoroborate (0.035 g, 0.122 mmol), potassium carbonate (0.168 g, 1.218 mmol), and palladium (II) acetate (14 mg, 0.061 mmol) were added to a microwave sample vessel. The solvent was degassed with argon twice. The microwave vial was heated in a microwave at 150° C. for three hours. The crude reaction mixture was filtered through celite. The celite was washed repeatedly with ethyl acetate. The combined organic fractions were washed with water twice, brine twice, dried with sodium sulfate and then concentrated en vacuo. Normal phase chromatography (methanol/DCM) was performed, followed by a reverse phase chromatography (water/acetonitrile) to give 3,7-dimethoxy-1-methyl-9H-pyrido[3,4-b]indole (0.115 g, 78% yield). $^1$H NMR (DMSO-$d_6$, 400 MHz) δ 11.03 (s, 1H), 7.99 (d, 1H, J=8.8 Hz), 7.18 (s, 1H), 6.92 (d, 1H, J=2.0 Hz), 6.76 (dd, 1H, J=2.4, 8.4 Hz), 3.87 (s, 3H), 3.86 (s, 3H), 2.65 (s, 3H). LCMS m/z 243.11 ([M+H]$^+$, $C_{14}H_{15}N_2O_2$ requires 243.11).

The compound of Example 40 can be converted to compounds of Formula I or Formula II using the procedure described in Example 3 and Scheme 1.

Example 41: Synthesis of 7-methoxy-4-methyl-5H-pyrido[4,3-b]indole

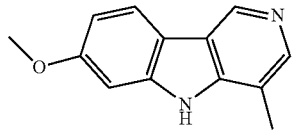 [SMILES: COc1ccc2c(c1)[nH]c1c(C)cncc12]

4-Bromo-3-methylpyridine (Astatech catalog #56516, 0.3 g, 1.744 mmol), 2-(dicyclohexylphosphino)-2',4',6'-tri-i-propyl-1,1'-biphenyl (0.062 g, 0.131 mmol), cesium carbonate (0.682 g, 2.093 mmol), anhydrous toluene (5 mL) and palladium (II) acetate (0.020 g, 0.087 mmol) were added to a microwave vial. Then, 2-chloro-5-methoxyaniline (0.289 g, 1.831 mmol) was added. The vial was purged with argon twice. The reaction was heated to 100° C. for 16 hours. The crude reaction mixture was filtered with celite. The celite was rinsed repeatedly with ethyl acetate to collect the crude product mixture. A normal-phase column was run (ethylacetate/hexanes) to give N-(2-chloro-5-methoxyphenyl)-6-methoxy-2-methylpyridin-3-amine (0.41 g, 95% yield).

N-(2-chloro-5-methoxyphenyl)-3-methylpyridin-4-amine (0.1572 g, 0.632 mmol), N,N-Dimethylacetamide (5 ml, Aldrich, 271012-100 ML), Tri-t-butylphosphonium tetrafluoroborate (0.037 g, 0.126 mmol), Potassium Carbonate (0.175 g, 1.264 mmol), and Palladium (II) Acetate (14 mg, 0.063 mmol, Aldrich, 520764-1G) were added to a microwave sample vessel. The solvent was degassed with argone twice. The microwave vial was heated in a microwave at 150° C. for three hours. The crude reaction mixture was filtered through celite. The celite was washed repeatedly with ethyl acetate. The combined organic fractions were washed with water twice, brine twice, dried with sodium sulfate and then concentrated en vacuo. Normal phase chromatography (methanol/DCM) was performed, followed by a reverse phase chromatography (water/acetonitrile) to give 7-methoxy-4-methyl-5H-pyrido[4,3-b]indole (0.089 g, 67% yield). $^1$H NMR (DMSO-$d_6$, 400 MHz) δ 11.56 (s, 1H), 9.05 (s, 1H), 8.17 (s, 1H), 8.05 (d, 1H, J=8.4 Hz), 7.02 (d, 1H, J=2.4 Hz), 6.86 (dd, 1H, J=2.4, 8.4 Hz), 3.85 (s, 3H), 2.50 (s, 3H). LCMS m/z 213.10 ([M+H]$^+$, $C_{13}H_{13}N_2O$ requires 213.10).

The compound of Example 41 can be converted to compounds of Formula I or Formula II using the procedure described in Example 3 and Scheme 1.

Example 42: 7-cyclopropoxy-1-methyl-9H-pyrido[3,4-b]indole

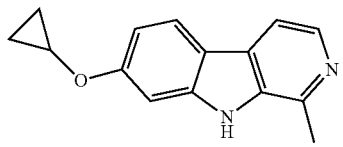 [SMILES: Cc1nccc2c1[nH]c1cc(OC3CC3)ccc12]

1-methyl-9H-pyrido[3,4-b]indol-7-ol (0.2 g, 1.009 mmol) was dissolved in DMF. Then, Cesium carbonate (0.329 g, 1.009 mmol) and Sodium hydride (0.089 g, 2.220 mmol) was added slowly. bromocyclopropane (0.122 g, 1.009 mmol) was added to the reaction mixture. The reaction was heated to 80° C. until no more starting material was detected via UPLC. The reaction mixture was quenched with water, extracted with ethyl acetate. The organic phase was washed with water three times, brine once, dried with sodium sulfate and then concentrated en vacuo. The crude residue was purified via normal phase chromatography (ethyl acetate/hexanes) and then reverse phase chromatography to give 7-cyclopropoxy-1-methyl-9H-pyrido[3,4-b]indole (0.067 g, 0.281 mmol, 27.9% yield). $^1$H NMR (DMSO-$d_6$, 400 MHz) δ 10.91 (s, 1H), 8.65 (d, 1H, J=5.2 Hz), 8.48 (d, 1H, J=8.8 Hz), 8.22 (d, 1H, J=5.2 Hz), 7.73 (d, 1H, J=2.0 Hz), 7.36 (dd, 1H, J=8.8, 2.4 Hz), 4.34 (m, 1H), 3.19 (s, 3H), 1.29 (m, 2H), 1.18 (m, 2H).

The compound of Example 42 can be converted to compounds of Formula I or Formula II using the procedure described in Example 3 and Scheme 1.

Example 43: 7-(1,1-difluoroethoxy)-1-methyl-9H-pyrido[3,4-b]indole

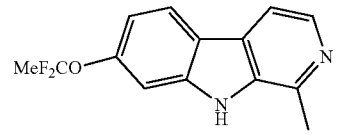

To a reaction flask was added 1-methyl-9H-pyrido[3,4-b]indol-7-ol (0.24 g, 1.211 mmol) a stir bar, acetonitrile (7.5 mL), water (0.5 mL) and Potassium hydroxide (0.075 g, 1.332 mmol). The reaction mixture is stirred for 2 min, and a portion of the 2-Bromo-1,1-difluoroethylene (0.095 ml, 1.211 mmol) in acetonitrile was added. The reaction mixture was heated to 65° C. for up to 12 h. The reaction mixture was cooled to room temperature, filtered through celite and then concentrated en vacuo. The crude residue was purified via normal phase chromatography (ethyl acetate/hexanes) to give 7-(2-bromo-1,1-difluoroethoxy)-1-methyl-9H-pyrido[3,4-b]indole (0.331 g, 0.970 mmol, 80% yield).

To a Parr bottle charged with 7-(2-bromo-1,1-difluoroethoxy)-1-methyl-9H-pyrido[3,4-b]indole (0.331 g, 0.970 mmol) and ethanol (10 mL) was added 10% Palladium on activated carbon (0.103 g, 0.970 mmol) as a slurry in 2 mL ethanol. The reaction was hydrogenated at 45 psi for 20 h. Upon completion detected by UPLC the mixture was filtered and concentrated en vacuo. The crude residue was purified via normal phase chromatography (ethyl acetate/hexanes) and then reverse phase chromatography to give 7-(1,1-difluoroethoxy)-1-methyl-9H-pyrido[3,4-b]indole (0.216 g, 0.824 mmol, 85% yield).

$^1$H NMR (DMSO-$d_6$, 400 MHz) δ 8.22 (m, 2H), 7.92 (d, 1H, J=5.2 Hz), 7.38 (s, 1H), 7.06 (dd, 1H, J=8.4, 2.0 Hz), 2.76 (s, 3H), 2.01 (t, 3H, J=14 Hz).

The compound of Example 43 can be converted to compounds of Formula I or Formula II using the procedure described in Example 3 and Scheme 1.

Example 44: 7-chloro-1-methyl-9H-pyrido[3,4-b]indole

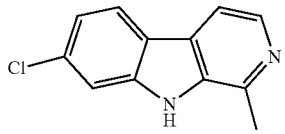

1-methyl-9H-pyrido[3,4-b]indol-7-ol (0.122 g, 0.615 mmol) was dissolved in Pyridine (0.487 g, 6.15 mmol) in a round bottomed flask equipped with a stir bar. The reaction mixture was cooled to 0° C. Then, Trifluoromethanesulphonic acid anhydride (0.114 ml, 0.677 mmol) was added dropwise. The reaction was allowed to slowly warm to room temperature and to stir overnight. Water was added to the reaction mixture and then extracted with ethyl acetate. The organic phase was washed with water three times, a copper sulfate solution twice, brine, dried with sodium sulfate and then concentrated en vacuo. The crude residue was purified via normal phase chromatography (ethyl acetate/hexanes) to give 1-methyl-9H-pyrido[3,4-b]indol-7-yl trifluoromethanesulfonate (0.103 g, 0.312 mmol, 50.7% yield).

To a screw-cap test tube equipped with a magnetic stir bar was added Potassium chloride (0.035 g, 0.472 mmol)), Potassium fluoride (6.86 mg, 0.118 mmol) and 1-methyl-9H-pyrido[3,4-b]indol-7-yl trifluoromethanesulfonate (0.078 g, 0.236 mmol)). The tube was sealed with a Teflon-lined septum, evacuated and backfilled with argon (this process was repeated a total of three times).

To another screw-cap test tube equipped with a magnetic stir bar was added Tris(dibenzylideneacetone)dipalladium (0) (3.24 mg, 3.54 µmol) and 2-(Di-tert-butylphosphino)-2',4',6'-triisopropyl-3,6-dimethoxy-1,1'-biphenyl (5.15 mg, 10.63 µmol). The tube was sealed with a Teflon-lined septum, evacuated and backfilled with argon (this process was repeated a total of three times). 1,4-Dioxane (1 mL) was added via syringe, and the mixture was heated at 120° C. in a preheated oil bath for 3 min. After the catalyst solution was cooled to room temperature, it was added to the reaction tube containing KCl, KF, and ArOTf via syringe, followed by addition of dioxane (3 mL). The resulting mixture was stirred vigorously at 130° C. in a preheated oil bath for 16 h and then cooled to room temperature, filtered through a pad of silica gel (eluted with EtOAc) and concentrated under reduced pressure. The crude material was purified via normal phase chromatography (ethyl acetate/hexanes) to give 7-chloro-1-methyl-9H-pyrido[3,4-b]indole (0.035 g, 0.162 mmol, 68.4% yield). $^1$H NMR (DMSO-d$_6$, 400 MHz) δ11.72 (s, 1H), 8.23 (d, 1H, J=1.2 Hz), 8.21 (d, 1H, J=1.6 Hz), 7.93 (d, 1H, J=5.6 Hz), 7.59 (d, 1H, J=2.0 Hz), 7.24 (dd, 1H, J=8.4, 2.0 Hz), 2.75 (s, 3H); LCMS m/z 217.05 ([M+H]$^+$, $C_{12}H_{10}ClN_2$ requires 217.05.

The compound of Example 44 can be converted to compounds of Formula I or Formula II using the procedure described in Example 3 and Scheme 1.

Example 45: 7-(difluoromethoxy)-1-methyl-9H-pyrido[3,4-b]indole

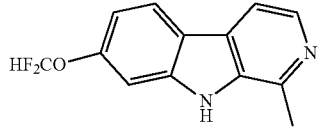

To a solution of 1-methyl-9H-pyrido[3,4-b]indol-7-ol (0.1 g, 0.504 mmol) and Potassium hydroxide (0.283 g, 5.04 mmol) acetonitrile (2 mL) and water (2 mL) was added Bromodifluoromethyl diethylphosphonate (0.099 ml, 0.555 mmol), at −15° C. After 30 minutes the mixture was allowed to warm to room temperature, stirred for another 30 min. and then treated with 1M aqueous and extracted with Et$_2$O. The combined organic layers were dried with sodium sulfate and concentrated in vacuo. The crude residue was purified by normal phase chromatography (ethyl acetate/hexanes) to give 7-(difluoromethoxy)-1-methyl-9H-pyrido[3,4-b]indole (0.075 g, 0.302 mmol, 59.9% yield). $^1$H NMR (DMSO-d$_6$, 400 MHz) δ11.70 (s, 1H), 8.24 (d, 1H, J=8.4 Hz), 8.20 (d, 1H, J=5.2 Hz), 7.91 (d, 1H, J=5.2 Hz), 7.35 (t, 1H, J=74 Hz, F-splitting), 7.30 (d, 1H, J=2.0 Hz), 7.05 (dd, 1H, J=8.4, 2.0 Hz), 2.71 (s, 3H); LCMS m/z 249.08 ([M+H]$^+$, $C_{13}H_{11}F_2N_2O$ requires 249.08.

The compound of Example 45 can be converted to compounds of Formula I or Formula II using the procedure described in Example 3 and Scheme 1.

Example 46: 7-(cyclopropylmethoxy)-1-methyl-9H-pyrido[3,4-b]indole

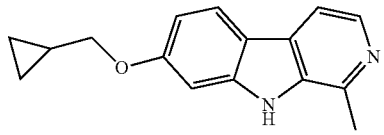 [SMILES: Cc1nccc2c1[nH]c1cc(OCC3CC3)ccc12]

1-methyl-9H-pyrido[3,4-b]indol-7-ol (0.1 g, 0.504 mmol) was dissolved in DMF (3 m and then placed in a 10 mL round bottomed flask equipped with a stir bar. Sodium hydride (0.020 g, 0.504 mmol) was added slowly and the reaction mixture was allowed to stir at room temperature for 30 minutes. Then, (bromomethyl)cyclopropane (0.047 ml, 0.504 mmol) was added slowly. The reaction was heated to 80° C. until completion. The reaction was quenched with water and then extracted with ethyl acetate. The organic phase was washed with water three times, brine once, dried with sodium sulfate and then concentrated en vacuo. The crude residue was purified via normal phase chromatography (ethyl acetate/hexanes) and then reverse phase chromatography to give 7-(cyclopropylmethoxy)-1-methyl-9H-pyrido[3,4-b]indole. NMR (DMSO-d$_6$, 400 MHz) δ11.37 (s, 1H), 8.13 (d, 1H, J=5.6 Hz), 8.03 (d, 1H, J=8.8 Hz), 7.78 (d, 1H, J=5.2 Hz), 6.96 (d, 1H, J=2.0 Hz), 6.83 (dd, 1H, J=8.8, 2.0 Hz), 3.93 (d, 2H, J=7.2 Hz), 2.71 (s, 3H), 1.27 (m, 1H), 0.60 (m, 2H), 0.38 (m, 2H).

The compound of Example 46 can be converted to compounds of Formula I or Formula II using the procedure described in Example 3 and Scheme 1.

Example 47: 4-(2-(7-(cyclopropylmethoxy)-1-(trifluoromethyl)-9H-pyrido[3,4-b]indol-9-yl)ethyl)morpholine

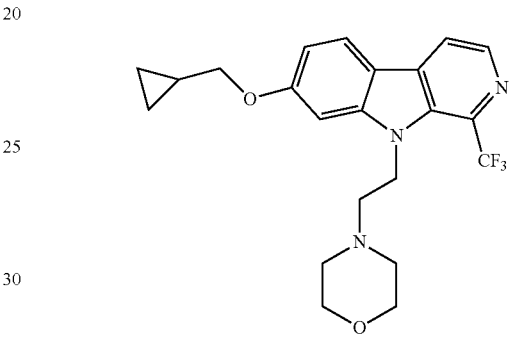

$^1$H NMR (DMSO-d$_6$, 400 MHz) δ8.44 (d, 2H, J=5.4 Hz), 8.40 (d, 2H, J=4.8 Hz), 8.23 (d, 1H, J=5.4 Hz), 7.24 (d, 1H, J=2.0 Hz), 7.00 (dd, 1H, J=8.4, 2.0 Hz), 4.58 (t, 2H, J=7.2 Hz), 4.01 (d, 2H, J=6.8 Hz), 3.53 (d, 4H, J=4.4 Hz), 2.59 (d, 2H, J=7.2 Hz), 2.44 (m, 4H), 1.33-1.28 (m, 1H), 0.65-0.60 (m, 2H), 0.41-0.37 (m, 2H).

Example 48: Modulation of Sclerostin/Wnt Activity

Compounds synthesized in accordance with the methods of Examples 1-46 were assayed for their ability to restore Wnt signaling in the presence of sclerostin consistent with a known sclerostin antagonist, sclerostin Mab. See, Ellies et al., J Bone Miner Res 21:1738-1749 (2006). As shown in Table 1 below, sclerostin antagonized Wnt3a signaling in human embryonic cells. The addition of a known sclerostin antagonist inhibited sclerostin inhibition of Wnt3a signaling, thus restoring Wnt3a signaling in the cell (IC100 at 10 μM) (data not shown). The compounds of Examples 1-46 also inhibited sclerostin inhibition of Wnt3a signaling and restored Wnt3a signaling in the cell.

Example 49: Bone Formation Assays

Mineralization (crystalline calcium phosphate formation) represents an in vitro model of bone formation. Using an assay in which the amount of mineralization is quantified by measuring total calcium after solubilization of deposited crystalline calcium phosphate, sclerostin was previously shown to inhibit mineralization in MC3T3-E1 (mouse calvarial) osteoblast cells. Li et al., *J Bone Miner Res* 24:578-588 (2008). Following the protocol described in Li et al., Compounds were assayed for their ability to rescue the inhibition of mineralization by sclerostin in MC3T3 osteoblast cells. Sclerostin treatment alone resulted in a significant decrease in mineralization, as measured by the calcium concentration (Table 1 and data not shown). Addition of a compound of Examples 1-46 neutralized sclerostin-mediated inhibition of mineralization, as reflected by the increase in calcium concentration.

Bone formation can also be assayed in vitro or in vivo using a serum marker for bone formation, osteocalcin (OCN), available from Biomedical Tecnhnologies, Inc. (Stoughton, Mass.). Following the manufacturer's protocol for the mouse osteocalcin EIA kit (described at the website www.btiinc.com/page/cata2.html#mouse_osteocalcin), bone formation in MC3T3 osteoblast cells was assayed by measuring the concentration of OCN. An ELISA assay, followed by spectrophotometer optical density (OD) readings to measure concentration of OCN, was used to detect the level of OCN secreted from cells treated with Sclerostin alone or with a combination of sclerostin and a compound of Examples 1-46. Treatment of the cells with sclerostin inhibited expression of OCN and resulted in nearly complete loss of OCN secretion (Table 1 and data not shown). In contrast, treatment with sclerostin and a compound of Examples 1-46 neutralized the inhibitory effects of sclerostin on OCN secretion, thus indicating that bone was formed.

TABLE 1

Compound activity on modulating sclerostin/Wnt activity, sclerostin inhibition of mineraliztion, and bone formation

| Patent Example | Sclerostin Inhibition Assay; improvement over sclerostin alone, | Sclerostin Inhibition of Mineralization; improvement over sclerostin alone. | OSTEOCALCIN (Bone Formation Marker) |
|---|---|---|---|
| sclerostin protein | − | − | − |
| 1 | + | + | + |
| 2 | + | + | + |
| 3 | ++ | ++ | ++ |
| 4 | ++ | ++ | ++ |
| 5 | ++ | ++ | ++ |
| 6 | ++ | ++ | ++ |
| 7 | ++ | ++ | ++ |
| 8 | ++ | ++ | ++ |
| 9 | ++ | ++ | ++ |
| 10 | ++ | ++ | ++ |
| 11 | ++ | ++ | ++ |
| 12 | ++ | ++ | ++ |
| 13 | ++ | ++ | ++ |
| 14 | ++ | ++ | ++ |
| 15 | ++ | ++ | ++ |
| 16 | ++ | ++ | ++ |
| 17 | ++ | ++ | ++ |
| 18 | ++ | ++ | ++ |
| 19 | ++ | ++ | ++ |
| 20 | + | + | + |
| 21 | + | + | + |
| 22 | ++ | ++ | ++ |
| 23 | ++ | ++ | ++ |
| 24 | ++ | ++ | ++ |
| 25 | ++ | ++ | ++ |
| 26 | ++ | ++ | ++ |
| 27 | ++ | ++ | ++ |
| 28 | ++ | ++ | ++ |
| 29 | ++ | ++ | ++ |
| 30 | ++ | ++ | ++ |
| 31 | ++ | ++ | ++ |
| 32 | ++ | ++ | ++ |
| 33 | ++ | ++ | ++ |
| 34 | ++ | ++ | ++ |
| 35 | ++ | ++ | ++ |
| 36 | + | + | + |
| 37 | ++ | ++ | ++ |
| 38 | ++ | ++ | ++ |
| 39 | ++ | ++ | ++ |
| 40 | ++ | ++ | ++ |
| 41 | + | + | + |
| 42 | + | + | + |
| 43 | ++ | ++ | ++ |
| 44 | ++ | ++ | ++ |
| 45 | ++ | ++ | ++ |
| 46 | ++ | ++ | ++ |

− indicates no improvement over sclerostin protein alone
+ indicates an IC100 > 10 µM
++ indicates an IC100 < 10 µM Example 50: hERG Assay One major type of cardiovascular toxicity associated with pharmaceutical drugs is caused by drug effects on cardiac ion channels like hERG. Drug-induced inhibition of hERG results in a prolonged QT interval, which can lead to a life-threatening ventricular arrhythmia.

Therefore, the inhibitory effect of compounds described in Examples 1-46 on the hERG potassium channel was evaluated using an automated patch clamp assay as described in Mathes, C. (2006) *Expert Opin. Ther. Targets*, 10 (2): 319-327. CHO-K1 cells stably expressing hERG channels were used. As shown in Table 2 below, cells were incubated with compounds from Examples 1-46 at a concentration of 1 µM for 5 minutes at room temperature, then inhibition of hERG tail current was measured. Table 2 demonstrates that a number of tested compounds exhibited less than 50% inhibition of hERG.

TABLE 2

| Patent Example | hERG (1 uM) |
|---|---|
| | hERG |
| 1 | + |
| 3 | + |
| 4 | + |
| 8 | + |
| 9 | + |
| 10 | + |
| 11 | + |
| 12 | + |
| 13 | + |
| 15 | ++ |
| 17 | + |
| 18 | + |
| 21 | + |
| 22 | + |
| 25 | + |
| 27 | + |
| 32 | + |
| 35 | + |
| 37 | + |
| 40 | + |

+ indicates less than 50% inhibition of hERG tail current
++ indicates more than 50% inhibition of hERG tail current Although the foregoing invention has been described in some detail by way of illustration and example for purposes of clarity of understanding, one of skill in the art will appreciate that certain changes and modifications can be practiced within the scope of the appended claims. In addition, each reference provided herein is incorporated by reference in its entirety to the same extent as if each reference was individually incorporated by reference.

What is claimed is:

1. A compound having the formula:

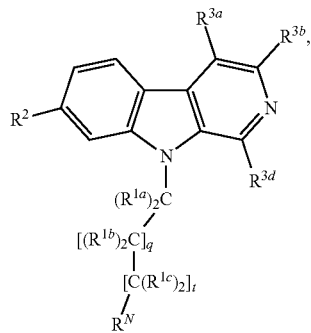

or a salt, or hydrate thereof; wherein
R$^2$ is selected from the group consisting of H, C$_{1-6}$ alkoxy, —OH, and C$_{1-6}$ alkyl-OH;
R$^{3a}$ and R$^{3b}$ are independently selected from the group consisting of H, halo, C$_{1-6}$ alkoxy, and —OH;
R$^{3d}$ is selected from the group consisting of H, C$_{1-6}$ alkyl and C$_{1-6}$ haloalkyl; and
the moiety

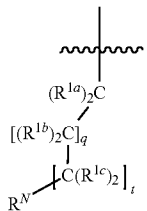

is selected from the group consisting of:

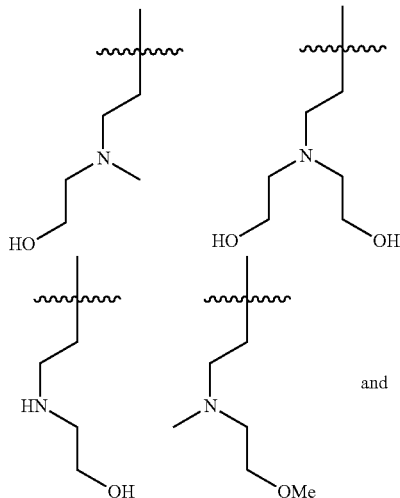

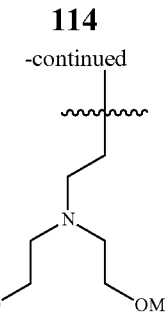

2. The compound of claim 1, wherein
R$^2$ is selected from the group consisting of —OH and methoxy; and
R$^{3a}$ and R$^{3b}$ are H.

3. The compound of claim 2, wherein R$^2$ is —OH.

4. The compound of claim 2, wherein R$^2$ is methoxy.

5. The compound of claim 2, wherein R$^{3d}$ is methyl or trifluoromethyl.

6. The compound of claim 2, wherein R$^{3d}$ is trifluoromethyl.

7. The compound of claim 2, wherein R$^{3d}$ is methyl.

8. The compound of claim 5, wherein

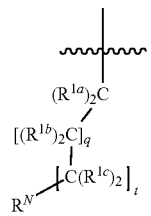

is selected from the group consisting of:

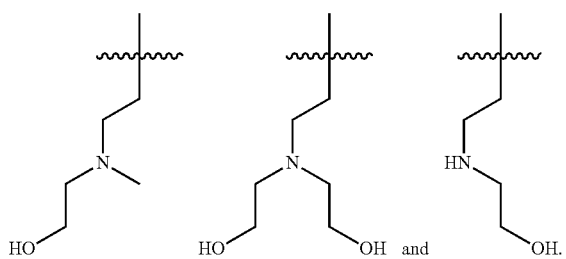

9. The compound of claim 5, wherein

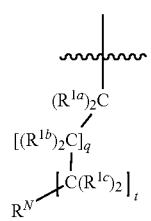

is selected from the group consisting of:

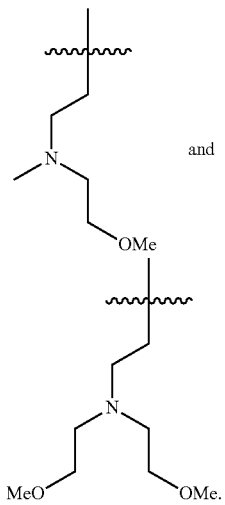 and

10. The compound of claim 1, wherein said compound is selected from the group consisting of
2-((2-(7-methoxy-1-methyl-9H-pyrido[3,4-b]indol-9-yl)ethyl)(methyl)amino)ethanol;
2-((2-(7-methoxy-1-(trifluoromethyl)-9H-pyrido[3,4-b]indol-9-yl)ethyl)amino)ethanol;
2,2'-((2-(7-methoxy-1-(trifluoromethyl)-9H-pyrido[3,4-b]indol-9-yl)ethyl)azanediyl)diethanol; and
2,2'-((2-(7-hydroxy-1-(trifluoromethyl)-9H-pyrido[3,4-b]indol-9-yl)ethyl)azanediyl)diethanol.

11. A formate salt of the compound of claim 1.

12. A citrate salt of the compound of claim 1.

13. A hydrochloride salt of the compound of claim 1.

14. A pharmaceutical composition comprising a compound of claim 1 and a pharmaceutically acceptable excipient.

* * * * *